"""

US005985275A

United States Patent [19]
Neurath et al.

[11] Patent Number: 5,985,275
[45] Date of Patent: Nov. 16, 1999

[54] β-LACTOGLOBULIN MODIFIED WITH AROMATIC ANHYDRIDE COMPOUND FOR PREVENTING HIV INFECTION

[75] Inventors: Alexander Robert Neurath; Asim Kumar Debnath, both of New York; Shibo Jiang, Jackson Heights, all of N.Y.

[73] Assignee: New York Blood Center, New York, N.Y.

[21] Appl. No.: 08/537,245

[22] Filed: Sep. 29, 1995

Related U.S. Application Data

[63] Continuation-in-part of application No. 08/492,940, Jun. 21, 1995, which is a continuation-in-part of application No. 08/420,573, Apr. 12, 1995, abandoned.

[51] Int. Cl.$^6$ .................................................. A61K 35/20
[52] U.S. Cl. .................................. 424/133.1; 424/157.1; 574/12; 574/21; 530/394; 530/402
[58] Field of Search .................... 514/12, 21; 424/157.1, 424/133.1; 530/394, 402

[56] References Cited

U.S. PATENT DOCUMENTS

| | | |
|---|---|---|
| 5,010,167 | 4/1991 | Ron et al. . |
| 5,164,486 | 11/1992 | Tsunoo et al. . |
| 5,256,412 | 10/1993 | Tsunoo et al. . |
| 5,290,571 | 3/1994 | Bounous et al. . |
| 5,456,924 | 10/1995 | Bounous et al. ........................ 424/535 |

FOREIGN PATENT DOCUMENTS

| | | |
|---|---|---|
| 327461 | 8/1989 | European Pat. Off. . |
| 568200 | 11/1993 | European Pat. Off. . |
| 584558 | 3/1994 | European Pat. Off. . |
| 8816302 | 7/1989 | France . |
| 92/15316 | 9/1992 | WIPO . |
| WO 92/15316 | 9/1992 | WIPO . |

OTHER PUBLICATIONS

Chemical Abstracts, vol. 105, No. 17, Oct. 27, 1986, Columbus, OH, abstract No. 148687, V. Siksnis et al., "Stabilization of Enzymes by their Chemical Modification with Cyclic Aromatic Acid Anhydrides", *Dokl. Akad. Nauk. SSSR*, vol. 288, No. 6, 1986 (1508–1512).

Chemical Abstracts, vol. 103, No. 23, Dec. 9, 1985, Columbus, OH, abstract No. 192648, R.J.M. Parker & R.S. Hodges, "Photoaffinity Probes Provide a General Method to Prepare Peptide Conjugates from Native Protein Fragments", *J. Prot. Chem.*, vol. 3, No. 5–6, 1984 (479–489).

Swart, P.J. and Meijer, D.K.F., *International Antiviral News*, "Negatively–Charged Albumins: A Novel Class of Polyanionic Proteins with a Potent Anti–HIV Activity", vol. 2, No. 5, Longmun Group Ltd., 69–71 (1994).

Harmsen, M.C., Swart, P.J., de Béthune, M.P., Pauwels, R., De Clercq, E., The, T.H. & Meijer, D.K.F., "Antiviral effects of plasma and milk proteins: Lactoferrin shows potent activity against both human immunodeficiency virus and human cytomegalovirus replication in vitro", *The Journal of Infectious Diseases*, 172, 380–388 (1995).

Gordon, L.M., Waring, A.J., Curtain, C.C., Kirkpatrick, A., Leung, C., Faull, K. & Mobley, P.W., "Antivirals that target the amino–terminal domain of HIV type 1 glycoprotein 41", *Aids Research and Human Retroviruses 11*, 6, 677–686 (1995).

Scofield et al, "Binding of Sperm to Somatic Cells Via HLA–DR Modulation by Sulfated Carbohydrates[1]", vol. 148, pp. 1718–1724, No. 6, (1992), *The Journal of Immunology*.

Phillips et al, "An Assay for HIV Infection of Cultured Human Cervix–Derived Cells", vol. 52, pp. 1–13 (1995), *Journal of Virological Methods*.

Ashida et al, "Lymphocyte Major Histocompatibility Complex–Encoded Class II Structures May Act as Sperm Receptors", vol. 84, pp. 3395–3399, (1987), *Immunology*.

Lundblad, R.L., *Chemical Reagents for Protein Modification*, 2nd Edition, CRC Press, Chapter 10, "The Modification of Lysine", 129–171 (1991).

Suzuki, T., Burlingame, R.W., Cavalot, F., Andres, G., Kashiwazaki, S. and Tan, E.M., "Antibodies in Rabbits Immunized with Cationized IgG React with Histones H3 and H4", *Arthritis and Rheumatism*, 35, 1218–1226 (1992).

Muckerheide, A., Apple, R.J., Pesce, A.J. and Michael, J.G., "Cationization of Protein Antigens", "I. Alteration of Immunogenic Properties", *The Journal of Immunology*, 138, 833–837 (1987).

Neurath, A. R., Strick, N., Haberfield, P., and Jiang, S., (1992), "Rapid Prescreening for Antiviral Agents Against HIV–1 Based on their Inhibitory Activity in Site–directed Immunoassays. II. Prophyrins Reacting with the V3 loop of gp120", *Antiviral Chem. Chemother.*, 3, 55–63.

Neurath, A. R., Haberfield, P., Joshi, B., Hewlett, I. K., Strick, N., and Jiang, S., (1991), "Rapid Prescreening for Antiviral Agents Against HIV–1 Based on their Inhibitory Activity in Site–directed Immunoassays I. The V3 loop of gp120 as Target", *Antiviral Chem. Chemother.*, 2, 303–312.

(List continued on next page.)

*Primary Examiner*—Cecillia J. Tsang
*Assistant Examiner*—Patrick Delaney
*Attorney, Agent, or Firm*—Frishauf, Holtz, Goodman, Langer & Chick, P.C.

[57] ABSTRACT

A composition is provided which comprises a protein or peptide containing lysines, wherein at least one of the lysines and/or the N-terminal amino group of the protein or peptide, such as casein, β-lactoglobulin, powdered milk or whey, is modified by contact with an aromatic acid anhydride compound, such as trimellitic anhydride, trimellitic anhydride chloride or 3-hydroxyphthalic anhydride. Additionally a composition is provided wherein a protein or peptide containing arginines is modified by an arginine modifying agent containing at least one carboxyl group, such as p-carboxyphenylglyoxal. The compositions are capable of binding to CD4 cell receptors, such as the HIV-1 or HIV-2 binding site on CD4 cell receptors. The compositions are thus useful for the prevention of HIV-1 or HIV-2 infection, especially by local administration.

17 Claims, 22 Drawing Sheets

OTHER PUBLICATIONS

Neurath, A.R. and Strick, N., (1980), "Antibodies as Immunological Probes for Studying the Denaturation of HBsAg", *J. Med. Virol. 6,* 309–322.

Jansen et al, R. W., Schols, D., Pauwels, R., DeClercq, E. and Meijer, D.K.F., "Novel Negatively Charged, Human Serum Albumins Display Potent and Selective in Vito Anti–Human Immunodeficiency Virus Type 1 Activity", 1993, vol. 44, pp. 1003–1007, Molecular Pharmacology.

Asim Kumar Debnath, Shibo Jiang, Nathan Strick, Kang Lin, Paul Haberfield and A. Robert Neurath, (1994), "Three–Dimensional Structure–Activity Analysis of a Series of Porphyrin Derivatives with Anti–HIV–1 Activity Targeted to the V3 Loop of the gp120 Envelope Glycoprotein of the Human Immunodeficiency Virus Type 1", *J. Med. Chem.,* 37, 1099–1108.

Neurath, A. R., Strick, N., Lin, K., Debnath, A. K., and Jiang, S. (1994), "Tin protoporphyrin IX Used in Control of Heme Metabolism in Humans Effectively Inhibits HIV–1 Infection", *Antiviral Chem. Chemother.,* 5, 322–330.

Jiang, S. and Neurath, A.R., (1992), "Potential Risks of Eliciting Antibodies Enhancing HIV–1 Infection of Monocytic Cells by Vaccination with V3 loops of Unmatched HIV–1 Isolates", *AIDS,* 6, 331–342).

Jiang, S., Lin, K., and Neurath, A.R., (1991), "Enhancement of Human Immunodeficiency Virus Type 1 Infection by Antisera to Peptides from the Envelope Glycoproteins gp120/gp41", *J. Exp. Med.,* 174, 1557–1563.

Fomsgaard, A., Hirsch, V.M., and Johnson, P.R., (1992), "Cloning and Sequences of Primate CD4 molecules: Diversity of the Cellular Receptor for Simian Immunodeficiency Virus/Human Immunodeficiency Virus", *Eur. J. Immunol.,* 22, 2973–2981.

Freed, E.O., Myers, D.J., and Risser, R., (1990), "Characterization of the Fusion Domain of the Human Immunodeficiency Virus Type 1 Envelope Glycoprotein gp41", *Proc Natl Acad Sci USA,* 87, 4650–4654.

Healey, D., Dianda, L., Moore, J.P., McDougal, J.S., Moore, M.J., Estess, P., Buck, D., Kwong, P.D., Beverley, P.C.L., and Sattentau, Q.J., (1990), "Novel anti–CD4 Monoclonal Antibodies Separate Human Immunodeficiency Virus Infection and Fusion of CD4+ Cells From Virus Binding", *J. Exp. Med.,* 172, 1233–1242.

Jansen, R.W., Molema, G., Pauwels, R., Schols, D., DeClercq, E. and Meijer, D.K.F., "Potent In Vitro Anti–Human Immunodeficiency Virus–1 Activity of Modified Human Serum Albumins", *Molecular Pharmacology,* 39, 818–823 (1991).

Marcon, L. and Sodroski. J. (1994), "gp120–Independent Fusion Mediated by the Human Immunodeficiency Virus Type 1 gp41 Envelope Glycoprotein: A Reassessment", *J. Virol.,* 68, 1977–1982.

McKenzie, H.A., (1971), "Whole casein: Isolation, Properties, and Zone Electrophoresis", In: *Milk Proteins Chemistry and Molecular Biology,* vol. II., H.A. McKenzie (ed.), pp. 87–116. Academic Press, New York.

Moore, J.P., (1993), "A Monoclonal Antibody to the CDR–3 Region of CD4 Inhibits Soluble CD4 Binding to Virions of Human Immunodeficiency Virus Type 1", *J. Virol.,* 67, 3656–3659.

Ostresh, J.M., Husar, G.M., Blondelle, S.E., Dörner, B., Weber, P.A., and Houghten, R.A., (1994), "Libraries from libraries: Chemical Transformation of Combinatorial Libraries to Extend the Range and Repertoire of Chemical Diversity," *Proc. Natl. Acad. Sci. USA,* 91, 11138–11142.

Ryu, S.–E., Truneh, A., Sweet, R.W., and Hendrickson, W.A., (1994), "Structures of an HIV and MHC Binding Fragment from Human CD4 as Refined in Two Crystal Lattices", *Structure,* 2, 59–74.

Parish, C.R., Low, L., Warren, H.S., and Cunningham, A.L., (1990), "A Polyanion Binding Site on the CD4 molecule. Proximity to the HIV–gp120 Binding Region," *J. Immunol.,* 145, 1188–1195.

Siegel, F., Kurth, R., and Norley, S., (1995), "Neither Whole Inactivated Virus Immunogen nor Passive Immunoglobulin Transfer Protects Against $SIV_{agm}$ Infection in the African Green Monkey Natural Host", *J. AIDS,* 8, 217–226.

Takami, M., Sone, T., Mizumoto, K., Kino, K., and Tsunoo, H. (1992), "Maleylated Human Serum Albumin Inhibits HIV–1 infection in Vitro", *Biochem. Biophys. Acta.,* 1180, 180–186.

Watanabe, M., Levine, C.G., Shen, L., Fisher, R.A., and Letvin, N.L. (1991), "Immunization of Simian Immunodeficiency Virus–Infected Rhesus Monkeys with Soluble Human CD4 Elicits and Antiviral Response," *Proc. Natl. Acad. Sci. USA,* 88, 4616–4620.

Watanabe, M., Chen, Z.W., Tsubota, H., Lord, C.I., Levine, C.G. and Letvin, N.L., (1991), "Soluble Human CD4 Elicits an Antibody Response in Rhesus Monkeys that Inhibits Simian Immunodeficiency Virus Replication", *Proc. Natl. Acad. Sci. USA,* 88, 120–124.

Watanabe, M., Boyson, J.E., Lord, C.I., and Letvin, N.L., (1992), "Chimpanzees Immunized with Recombinant Soluble CD4 Develop Anti–self CD4 Antibody Responses with Anti–human Immunodeficiency Virus Activity", *Proc. Natl. Acad. Sci. USA,* 89, 5103–5107.

Wilks, D., Walker, L., O'Brien, J., Habeshaw, J., and Dalgleish, A., (1990), "Differences in Affinity of Anti–CD4 Monoclonal Antibodies Predict their Effects on Syncytium Induction by Human Immunodeficiency Virus", *Immunol.,* 71, 10–15.

Peterson, A. and Seed, B., (1988), "Genetic Analysis of Monoclonal Antibody and HIV Binding Sites on the Human Lymphocyte Antigen CD4", *Cell,* 54, 65–72.

Sattentau, Q.J., Arthos, J., Deen, K., Hanna, N., Healey, D., Beverley, P.C.L., Sweet, R., and Truneh, A., (1989), "Structural Analysis of the Human Immunodeficiency Virus–binding Domain of CD4", *J. Exp. Med.,* 170, 1319–1334.

Houlgatte, R., Scarmato, P., El Marhomy, S., Martin, M., Ostankovitch, M., Lafosse, S., Vervisch, A., Auffray, C., and Platier–Tonneau, D., (1994), "HLA class II Antigens and the HIV Envelope Glycoprotein gp120 Bind to the Same Face of CD4", *J. Immunol.,* 152, 4475–4488.

Camerini, D. and Seed, B., (1990), "A CD4 Domain Important for HIV–Mediated Syncytium Formation Lies Outside the Virus Binding Site", *Cell,* 60, 747–754.

Nicholls, A., Sharp, K., and Honig, B. (1991), "Protein Folding and Association: Insights from the Interfacial and Thermodynamic Properties of Hydrocarbons," *Proteins,* 11, 281–296.

Bernstein, F.C., Koetz, T.F., Williams, G.J.B., Meyer, E.F., Jr., Brice, M.D., Rodgers, J.R., Kennard, O., Shimanouchi, T., Tasumi, M., (1977), "The Protein Data Bank: A computer–based Archival File for Macromolecular Structure", *J. Mol. Biol.,* 112, 535–542.

Lundblad, R. C., (1991), *Chemical Reagents For Protein Modification*, CRC Press, Boca Raton, Florida.

In: *Methods in Enzymology.*, vol. 92. Immunochemical Techniques, Langone, J.J. and Van Vunakis, H. (eds.), pp. 577–588, Academic Press, New York.

Modern Approaches to New Vaccines Including Prevention of AIDS, H.S. Ginsberg, F. Brown, R.M. Chanock, and R.A. Lerner (eds.), pp. 203–208, Cold Spring Harbor Laboratory Press, New York.

Abraham, R., Singh, N., Mukhopadhyay, A., Basu, S.K., Bal, V., and Rath, S., (1994), "Modulation of Immunogenicity and Antigenicity of Proteins by Maleylation to Target Scavenger Receptors on Macrophages," *J. Immunol.*, 154, 1–8.

George, D.G., Barker, W.C., Mewes, H.–W., Pfeiffer, F., and Tsugita, A., (1994), "The PIR–International Protein Sequence Database", *Nucl. Acids Res.*, 22, 3569–3573.

Lederman, S., Gulick, R., and Chess, L., (1989), "Dextran Sulfate and Heparin Interact with CD4 Molecules to Inhibit the Binding of Coat Protein (gp120) of HIV", *J. Immunol.*, 143, 1149–1154.

Yahi, N., Sabatier, J.–M., Baghdiguian, S., Gonzalez–Scarano, F. and Fantini, J., "Synthetic Multimeric Peptides Derived from the Principal Neutralization Domain (V3 loop) of Human Immunodeficiency Virus Type 1 (HIV–1) gp120 Bind to Galactosylceramide and Block HIV–1 Infection in a Human CD4–negative Mucosal Epithelial Cell Line", *J. Virol.*, 69, 320–325 (1995).

Lo, T.W.C., Westwood, M.E., McLellan, A.C., Selwood, T. and Thornalley, P.J., "Binding and Modification of Proteins by Methylglyoxal Under Physiological Conditions. A kinetic and Mechanistic Study with Nα–Acetylarginine, Nα–Acetylcysteine, and Nα–Acetyllysine, and Bovine serum albumin", (1994), *J. Biol. Chem.*, 269, 32299–32305.

Westwood, M.E., McLellan, A.C., and Thornalley, P.J., (1994), "Receptor–mediated Endocytic Uptake of Methylglyoxal–modified Serum Albumin. Competition with Advanced Glycation End Product–modified Serum Albumin at the Advanced Glycation End Product Receptor", *J. Biol. Chem.*, 269, 32293–32298.

Yahi, N., Baghdiguian, S., Moreau, H. and Fantini, J., "Galactosyl Ceramide (or a Closely Related Molecule) is the Receptor for Human Immunodeficiency Virus Type 1 on Human Colon Epithelial HT29 Cells", *J. Virol.*, 66, 4848–4854 (1992).

Yahi, N. et al., "Suramin Inhibits Binding of the V3 Region of HIV–1 Envelope Glycoprotein gp120 to Galactosylceramide, the Receptor for HIV–1 gp 120 on Human Colon Epithelial Cells", *J. Biol. Chem.* 269, 24349–24353 (1994).

Long, D., Berson, J.F., Cook, D.G. and Doms, R.W., "Characterization of Human Immunodeficiency Virus Type 1 gp120 Binding to Liposomes Containing Galactosylceramide", *J. Virol.*, 68, 5890–5898 (1994).

Furuta, Y. et al., "Infection of Vaginal and Colonic Epithelial Cells by the Human Immunodeficiency Virus Type 1 is Neutralized by Antibodies Raised Against Conserved Epitopes in the Envelope Glycoprotein gp120", *Proc. Natl. Acad. Sci U.S.A.*, 91, 12559–12563 (1994).

Fantini, J., Cook, D.G., Nathanson, N., Spitalnik, S.L. and Gonzalez–Scarano, F., "Infection of Colonic Epithelial Cell Lines by Type 1 Human Immunodeficiency Virus is Associated with Cell Surface Expression of Galactosylceramide, a Potential Alternative gp120 Receptor", *Proc. Natl. Aca. Sci. U.S.A.*, 90, 2700–2704 (1993).

Cook, D.G., Fantini, J., Spitalnik, S.L. and Gonzalez–Scarano, F., "Binding of Human Immunodeficiency Virus Type 1 (HIV–1) gp120 to Galactosylceramide (GalCer): Relationship to the V3 Loop", *Virology*, 201, 206–214 (1994).

Webster II University Dictionary Defining "Plasma", (1988).

Delgado, "Uses & Properties of Peg–Linked Proteins" Embase 92348412, (1992).

"Advances in Food & Nutrition Research" #33 John Kinsella, Academic Press, (1989).

Baruchel et al, "Anti–HIV Activity of Whey Protein" AIDS Conf., Yokohama, (Aug. 7, 1994) p. 404.

FIG. 6

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 22 amino acids
      (B) TYPE: amino acid
      (C) STRANDEDNESS: single stranded
      (D) TOPOLOGY: linear (ii) MOLECULE TYPE: cDNA to genomic RNA (xi) SEQUENCE DESCRIPTION: SEQ ID NO:1:

```
Asn Asn Thr Arg Lys Lys Ile Arg Ile Gln Arg Gly Pro Gly Arg Ala
 1               5                  10                  15
Phe Val Thr Ile Gly Lys
            20
```

β-LACTOGLOBULIN MODIFIED WITH AROMATIC ANHYDRIDE COMPOUND FOR PREVENTING HIV INFECTION

CROSS REFERENCE TO RELATED APPLICATION

This is a continuation-in-part application of application Ser. No. 08/492,940, filed Jun. 21, 1995, which is a continuation-in-part application of application Ser. No. 08/420,573, filed Apr. 12, 1995 now abandoned.

GOVERNMENT RIGHTS

This invention was made with United States Government support under Grants CA 43315 and AI 29373 from the National Institutes of Health. Accordingly, the United States Government has certain rights in this invention.

BACKGROUND OF THE INVENTION

1. Field of the Invention

The present invention concerns lysine-containing proteins or peptides modified by a lysine modifying agent such as an aromatic acid anhydride compound, and arginine-containing proteins or peptides modified by an arginine modifying agent, which modified proteins or peptides are useful for preventing HIV-1 or HIV-2 infection by binding to the cellular CD4 receptors for these viruses.

2. Background Information

Human immunodeficiency viruses ("HIV") have been known as the causative virus for AIDS (Acquired Immunodeficiency Syndrome). The prevalence of AIDS cases is presently increasing at an alarming rate.

Two related retroviruses that can cause AIDS are human immunodeficiency virus type 1 (HIV-1) and type 2 (HIV-2). The genomes of these two viruses are about 50% homologous at the nucleotide level, contain the same complement of genes, and appear to attack and kill the same human cells by the same mechanism.

HIV-1 was identified in 1983. Virtually all AIDS cases in the United States are associated with HIV-1 infection. HIV-2 was isolated in 1986 from West African AIDS patients.

HIV-1 and HIV-2 are retroviruses in which the genetic material is RNA, rather than DNA. The HIV-1 and HIV-2 viruses carry with them a polymerase (reverse transcriptase) that catalyzes transcription of viral RNA into double-helical DNA.

The viral DNA can exist as an unintegrated form in the infected cell or be integrated into the genome of the host cell. As presently understood, the HIV enters the T4 lymphocyte where it loses its outer envelope, releasing viral RNA and reverse transcriptase.

The reverse transcriptase catalyzes synthesis of a complementary DNA strand from the viral RNA template. The DNA helix then inserts into the host genome where it is known as the provirus. The integrated DNA may persist as a latent infection characterized by little or no production of virus or helper/inducer cell death for an indefinite period of time. When the viral DNA is transcribed and translated by the infected lymphocyte, new viral RNA and proteins are produced to form new viruses that bud from the cell membrane and infect other cells.

Attempts to treat AIDS with drugs which inhibit reverse transcriptase such as 3'-azido-3'-deoxythymidine (AZT) have not been met with a desirable degree of success. Moreover, there is a potential for toxicity with the use of anti-viral drugs. Thus there is a need for an effective and safe means to prevent and treat AIDS.

HIV infections are transmitted by means such as contaminated intravenous drug needles and through sexual contact. Sexual transmission is the most frequent (86%) route of adult HIV-1 infections worldwide (AIDS in the World, Harvard University Press, Cambridge, Mass., (1992)).

The transmission of HIV by heterosexual sex poses an especially severe problem for women. By the year 2,000, it is estimated that 90% of HIV infection will be acquired via heterosexual intercourse.

The utilization of condoms provides a substantial degree of protection against transmission of HIV infections during sexual intercourse, but a difficulty arises when condoms are not employed. Moreover, the use of condoms appears to be a culturally and socially unacceptable practice in many countries.

Although men can protect themselves from HIV infection by using condoms, women who are sexually active have no similar means. Women can encourage their male sex partners to use a condom, but may not succeed. The female condom, which is just becoming available, is expensive and there is presently no evidence that it prevents transmission of HIV.

Even maintaining a monogamous sexual relationship is no guarantee of safety, for if a woman's male partner becomes infected, he can pass the virus to her. And as more women are infected, so are more babies.

There is presently frustration in the medical field by the bleak prospect for an effective AIDS vaccine in the near future and the severe limitations of drugs that effectively and safely combat HIV.

Due to the present absence of a prophylactic anti-HIV vaccine and because of limitations of educational programs, other preventive methods have been sought. Spermicides with virucidal properties have been considered for this purpose, but their application is contraindicated by adverse effects (Bird, K. D., "The Use of Spermicide Containing Nonoxynol-9 in the Prevention of HIV Infection", AIDS, 5, 791–796 (1991)).

Anti-HIV drugs currently in use or expected to be clinically. applied in the near future (Steele, F., "AIDS Drugs Lurch Towards Market", *Nature Medicine*, 1, 285–286 (1995)) are mostly not targeted emergence of drug resistant mutants, and are expensive, suggesting that their application for wide use in topical chemoprophylaxis is unlikely.

Cells which are the primary targets for sexual and mucosal transmission of HIV, either in the form of free virus or virus-infected cells, have not been fully defined and may be diverse (Miller, C. J. et al., "Genital Mucosal Transmission of Simian Immunodeficiency Virus: Animal Model for Heterosexual Transmission of Human Immunodeficiency Virus", *J Virol*, 63, 4277–4284 (1989); Phillips, D. M. and Bourinbaiar, A. S., "Mechanism of HIV Spread from Lymphocytes to Epithelia", *Virology*, 186, 261–273 (1992); Phillips, D. M., Tan, X., Pearce-Pratt, R. and Zacharopoulos, V. R., "An Assay for HIV Infection of Cultured Human Cervix-derived Cells", *J. Virol. Methods*, 52, 1–13 (1995); Ho, J. L. et al., "Neutrophils from Human Immununodeficiency Virus (HIV)-Seronegative Donors Induce HIV Replication from HIV-infected Patients Mononuclear Cells and Cell lines": An In Vitro Model of HIV Transmission Facilitated by *Chlamydia Trachomatis., J. Exp. Med.*, 181, 1493–1505 (1995); and Braathen, L. R. & Mork, C. in "HIV infection of Skin Langerhans Cells", In: *Skin Langerhans (dendritic) cells in virus infections and AIDS* (ed. Becker, Y.)

131–139 (Kluwer Academic Publishers, Boston, (1991)). Such cells include T lymphocytes, monocytes/macrophages and dendritic cells, suggesting that CD4 cell receptors are engaged in the process of virus transmission (Parr, M. B. and Parr, E. L., "Langerhans Cells and T lymphocyte Subsets in the Murine Vagina and Cervix", *Biology of Reproduction*, 44, 491–498 (1991); Pope, M. et al., "Conjugates of Dendritic Cells and Memory T Lymphocytes from Skin Facilitate Productive Infection With HIV-1", *Cell*, 78, 389–398 (1994); and Wira, C. R. and Rossoll, R. M., "Antigen-presenting Cells in the Female Reproductive Tract: Influence of Sex Hormones on Antigen Presentation in the Vagina", *Immunology*, 84, 505–508 (1995)).

Therefore agents blocking HIV-CD4 binding are expected to diminish or prevent virus transmission. Soluble recombinant CD4 cannot be considered for this purpose since high concentrations are required to neutralize the infectivity of primary HIV isolates (Daar, E. S., Li, X. L., Moudgil, T. and Ho, D. D., "High Concentrations of Recombinant Soluble CD4 are Required to Neutralize Primary Human Immunodeficiency Virus Type 1 Isolates", *Proc. Natl. Acad. Sci. U.S.A.*, 87, 6574–6578 (1990)), and in the case of SIV, the infectivity is enhanced by CD4 (Werner, A., Winskowsky, G. and Kurth, R., "Soluble CD4 Enhances Simian Immunodeficiency Virus SIVagm Infection", *J. Virol.*, 64, 6252–6256 (1990). However, anti-CD4 antibodies are expected to prevent virus transmission independently of subtype and variability, but their application would be too costly (Daar et al, supra, Watanabe, M., Boyson, J. E., Lord, C. I. and Letvin, N. L. "Chimpanzees Immunized with Recombinant Soluble CD4 Develop Anti-self CD4 Antibody Responses with Anti-human Immunodeficiency Virus Activity", *Proc. Natl. Acad. Sci. USA.*, 89, 5103–5107 (1992); and Perno, C.-F., Baseler, M. W., Broder, S. and Yarchoan, R., "Infection of Monocytes by Human Immunodeficiency Virus Type 1 Blocked by Inhibitors of CD4-gp120 Binding, Even in the Presence of Enhancing Antibodies", *J. Exp. Med.*, 171, 1043–1056 (1990)).

There is a need for a safe and effective substance that can be inserted into the vagina by a foam, gel, sponge or other form to prevent HIV-1 or HIV-2 from infecting cells in the body. It is hoped that such substance be used by a woman without her partner's knowledge.

Prospects for the near and possibly not so near future to prevent HIV-1 transmission by vaccination do not seem good. A recent report that vaccination with inactivated SIV did not protect African Green monkeys against infection with the homologous virus notwithstanding a strong immune response to SIV does not appear to be encouraging in this respect (Siegel, F., Kurth, R., and Norley, S., (1995), "Neither Whole Inactivated Virus Immunogen nor Passive Immunoglobulin Transfer Protects Against $SIV_{agm}$ Infection in the African Green Monkey Natural Host", *J. AIDS*, 8, 217–226) Considering this problem, emphasis has been put on attempts to build a chemical barrier to HIV-1 transmission (Taylor, (1994), "Building a Chemical Barrier to HIV-1 Transmission", *J. NIH Res.*, 6, 26–27).

The development of topically applied microbicides, expected to prevent sexual (mucosal) transmission of HIV-1, was suggested to need to be "effective against all sexually transmitted diseases and should not be seen, smelled, or felt while in use." It should also be inexpensive and widely available, and $25 million was expected to be devoted to its development in the United States in 1995 (Taylor, (1994) supra). Detergents (nonoxynol-9) as a universal pathogen killer have been selected for clinical trials. However, not surprisingly, this compound proved to be deleterious to the host.

Targeting the chemical barrier to transmission of individual pathogens and abandoning the requirement for microbicidal activity or combining it with other approaches would perhaps facilitate the development of compounds preventing the transmission of human immunodeficiency viruses. For example, effective blockade of receptors for the viruses might accomplish this goal. This concept may be supported by the finding that immunization of chimpanzees and rhesus monkeys, respectively, with human CD4 which has several amino acid point mutations in comparison with non-human primate CD4 sequences (Fomsgaard, A., Hirsch, V. M., and Johnson, P. R., (1992), "Cloning and Sequences of Primate CD4 molecules: Diversity of the Cellular Receptor for Simian Immunodeficiency Virus/Human Immunodeficiency Virus", *Eur. J. Immunol.*, 22, 2973–2981), developed anti-CD4 antibodies which inhibited HIV-1 and SIV replication (Watanabe, M., Levine, C. G., Shen, L., Fisher, R. A., and Letvin, N. L. (1991), "Immunization of Simian Immunodeficiency Virus-Infected Rhesus Monkeys with Soluble Human CD4 Elicits an Antiviral Response," *Proc. Natl. Acad. Sci. USA*, 88, 4616–4620. Watanabe, M., Chen, Z. W., Tsubota, H., Lord, C. I., Levine, C. G., and Letvin, N. L., (1991), "Soluble Human CD4 Elicits an Antibody Response in Rhesus Monkeys that Inhibits Simian Immunodeficiency Virus Replication", *Proc. Natl. Acad. Sci. USA*, 88, 120–124; and Watanabe, M., Boyson, J. E., Lord, C. I., and Letvin, N. L., (1992), "Chimpanzees Immunized with Recombinant Soluble CD4 Develop Anti-self CD4 Antibody Responses with Anti-human Immunodeficiency Virus Activity", *Proc. Natl. Acad. Sci. USA*, 89, 5103–5107).

In an effort to expand the diversity of compounds with medically useful biological activities, the chemical transformation of synthetic peptide-based or other combinatorial Libraries of organic compounds has been recently conceived (Ostresh, J. M., Husar, G. M., Blondelle, S. E., Dorner, B., Weber, P. A., and Houghten, R. A., (1994), "Libraries from Libraries: Chemical Transformation of Combinatorial Libraries to Extend the Range and Repertoire of Chemical Diversity," *Proc. Natl. Acad. Sci. USA*, 91, 11138–11142). Such transformations can be accomplished with reagents which alter chemical moieties of library constituents in a defined manner and high yield. The diversity of compounds of interest to medicinal chemistry can be also increased by applying the concept of chemical modification to natural products, either in the form of mixtures of compounds or in the form of isolated individual components.

Site-specific chemical modification of amino acid residues in proteins has been widely used in structure/function studies in which a loss or decrease of biological activity was related to chemical modification of specific amino acid residues. Methods for covalent chemical modification of C, M, H, K, R, W, Y residues and carboxyl groups were described and applied to many proteins (Lundblad, R. C., (1991), *Chemical Reagents For Protein Modification*, CRC Press, Boca Raton, Fla.). In a few cases, it was reported that changes in net electric charge caused by chemical modification of proteins increased their activity ["cationized" protein antigens were reported to have increased or altered immunogenicity (Muckerheide et al., 1987; Suzuki et al., 1992)] or mimicked changes occurring during in vivo protein turnover, causing binding of the chemically modified proteins to scavenger receptors on cells, (Westwood, M. E., McLellan, A. C., and Thornalley, P. J., (1994), "Receptor-mediated Endocytic Uptake of Methylglyoxal-modified Serum Albumin. Competition with Advanced Glycation End Product-modified Serum Albumin at the Advanced Glycation End Product Receptor", *J. Biol. Chem.*, 269, 32293–32298; Lo, T. W. C., Westwood, M. E., McLellan, A. C., Selwood, T., and Thornalley, P. J., (1994), "Binding and Modification of Proteins by Methylglyoxal Under Physiological Conditions. A kinetic and Mechanistic Study with Nα-Acetylarginine, Nα-Acetylcysteine, and Nα-Acetyllysine, and Bovine Serum Albumin", *J. Biol. Chem.*, 269, 32299–32305; Abraham, R., Singh, N., Mukhopadhyay, A., Basu, S. K., Bal, V., and Rath, S., (1994), "Modulation of Immunogenicity and Antigenicity of Proteins by Maleylation to Target Scavenger Receptors on Macrophages," *J. Immunol.*, 154, 1–8).

Heretofore U.S. Pat. Nos. 5,164,486 and U.S. Pat. No. 5,256,412 (hereinafter collectively referred to as "Tsunoo et al") disclosed an anti-HIV agent comprising a plasma protein of which the polarity of at least one amino group was chemically modified into a negatively charged moiety by using aliphatic acid anhydrides. Tsunoo et al discussed treatment, not prevention of HIV infection, preferably by intravenous administration. Tsunoo et al mentioned maleic anhydride and succinic anhydride, but did not discuss aromatic acid anhydrides. The treated proteins blocked fusion of infected cells with uninfected cells by blocking HIV-1 mediated fusion. Tsunoo et al described plasma proteins such as human serum albumin, human immunoglobulin, human transferrin and human fibrinogen, but did not discuss milk, casein or whey.

Jansen et al (WO 92/15316) and "Potent In Vitro Anti-Human Immunodeficiency Virus-1 Activity of Modified Human Serum Albumins", *Molecular Pharmacology*, 39, 818–823 (1991) ) described the use of cis-aconitic anhydride, propane-1,2,3-tricarboxylic acid anhydride, acetic anhydride, propionic anhydride, butyric anhydride, glutaric anhydride phthalic anhydride, and maleic anhydride to modify protein and polypeptides from proteins such as serum albumin to prepare anti-viral pharmaceuticals, by imparting a negative charge to the proteins or polypeptides. The examples in WO 92/15316 were carried out only with aliphatic acid anhydrides.

The antiviral activity of the compounds discussed in the two preceding paragraphs is considered to be ascribed to their interference with virus-induced fusion and to the possible binding of the compounds to the HIV-1 fusion domain.

However, to the best of applicants' knowledge, there have not been reported attempts to systematically modify protein amino acid residues of one or more kinds in order to (1) generate compounds with medically important biological properties, of which the original protein was totally devoid; (2) produce at the same time a compound(s) having the particular biological activity optimized and (3) generate compounds for binding to cell receptors for viruses which interfere with the initial binding of viruses to cells, thereby preventing infection.

SUMMARY OF THE INVENTION

It is an object of the present invention to provide a composition comprising a modified protein or peptide which is capable of binding to the HIV-1 or HIV-2 binding site on CD4 cell receptors.

It is another object of the present invention to provide a method to prevent HIV-1 or HIV-2 infection and more particularly to prevent vaginal and anal transmission of HIV-1 or HIV-2 during sexual intercourse or vaginal transmission during childbirth.

The aforesaid objects, as well as other objects, aims and advantages are satisfied by the present invention.

The present invention concerns a composition comprising a protein or peptide containing lysines, wherein at least one, such as all or some, of the lysines and/or the N-terminal amino group of the protein or peptide is modified by contact with an aromatic acid anhydride compound, the composition being capable of binding to a CD4 cell receptor.

The present invention also relates to a method of modifying a protein or a peptide to make the protein or peptide capable of binding to a CD4 cell receptor. The method comprises contacting a protein or peptide containing lysine groups with an aromatic acid anhydride compound to modify at least one, such as all or some, of the lysine groups and/or the N-terminal amino acid group of the protein or peptide.

The present invention is also directed to a composition comprising a protein or peptide containing arginines, wherein at least one arginine is modified by contact with an arginine modifying agent containing at least one carboxyl group, for example, p-carboxyphenylglyoxal to make the composition capable of binding to a CD4 cell receptor.

The present invention additionally relates to a method of modifying a protein or a peptide containing arginines comprising contacting the protein or peptide with an arginine modifying agent containing at least one carboxyl group, for example, p-carboxyphenylglyoxal, to make the protein or peptide capable of binding to a CD4 cell receptor.

The modified protein or peptide containing lysine, arginine or both, described above, can be further treated with polyethylene glycol (PEG) ("PEGylation"). Since lysines and/or arginines are utilized in chemical modifications in the present invention, the PEG is linked to cysteine residues. Therefore the amount of PEG to be used depends on the amount of cysteine residues in the protein or peptides. The "PEGylated" modified proteins or peptides are candidates for anti-HIV-1 agents for intravenous administration. The treatment with PEG can be carried out before or after the protein or peptide is modified.

The present invention is further directed to a method of preventing HIV-1 or HIV-2 infection in a human by administering to a human a pharmaceutically effective amount of a composition containing a modified protein or peptide (containing lysine, arginine or both) as described hereinabove.

BRIEF DESCRIPTION OF THE DRAWINGS

The file of this patent contains at least one drawing executed in color. Copies of this patent with the color drawing will be provided by the Patent and Trademark Office upon request and payment of the necessary fee.

FIG. 6 is a graph of antiviral activities (expressed as $ED_{50}$ for inhibition of CPE) versus inhibitory effects on gp120-CD4 association for chemically modified proteins and polymers listed in Table 1 herein. The corresponding numbers are indicated near each experimental point. Points in the lower left portion of the graph correspond to compounds with the highest activities.

FIG. 17a shows HIV-IIIB gp120-CD4 binding as determined by the NENQUEST test. FIG. 17b shows binding of horseradish peroxidase (HRP)-labeled CD4 (500 ng) to wells coated with surface envelope glycoproteins of distinct primate immunodeficiency viruses. The apparent discrepancy between $IC_{50}$ values calculated from results shown in FIG. 17a and FIG. 17b is due to distinct assay formats and concentrations of reagents. FIG. 17c shows binding to CD4-coated wells of mAbs Q4120 (1 μg) and OKT4a (100 ng), respectively, each known to block the gp120 binding site on CD4. FIG. 17d shows binding of HRP-labeled CD4 (500 ng) to wells coated with trimellitic anhydride treated BSA. Absorbance readings at 450 nm ($OD_{450}$) corresponding to binding reactions a–d in the absence of 3HP-β-LG were in the range of 0.58 to 1.63. The percentages of inhibition for each 3HP-β-LG concentration were calculated and plotted after logit transformation against log [3HP-β-LG (nM)] (Ritchie, D. G., Nickerson, J. M. and Fuller, G. M., "Two Simple Programs for the Analysis of Data from Enzyme-linked Immunosorbent Assays (ELISA) on a Programmable Desk-top Calculator", *Methods Enzymol.*, 92, 577–588 (1983)). The corresponding linear regressions [correlation coefficients (r) were 0.97 to 0.996] are presented.

DETAILED DESCRIPTION OF THE INVENTION

Figure 1:
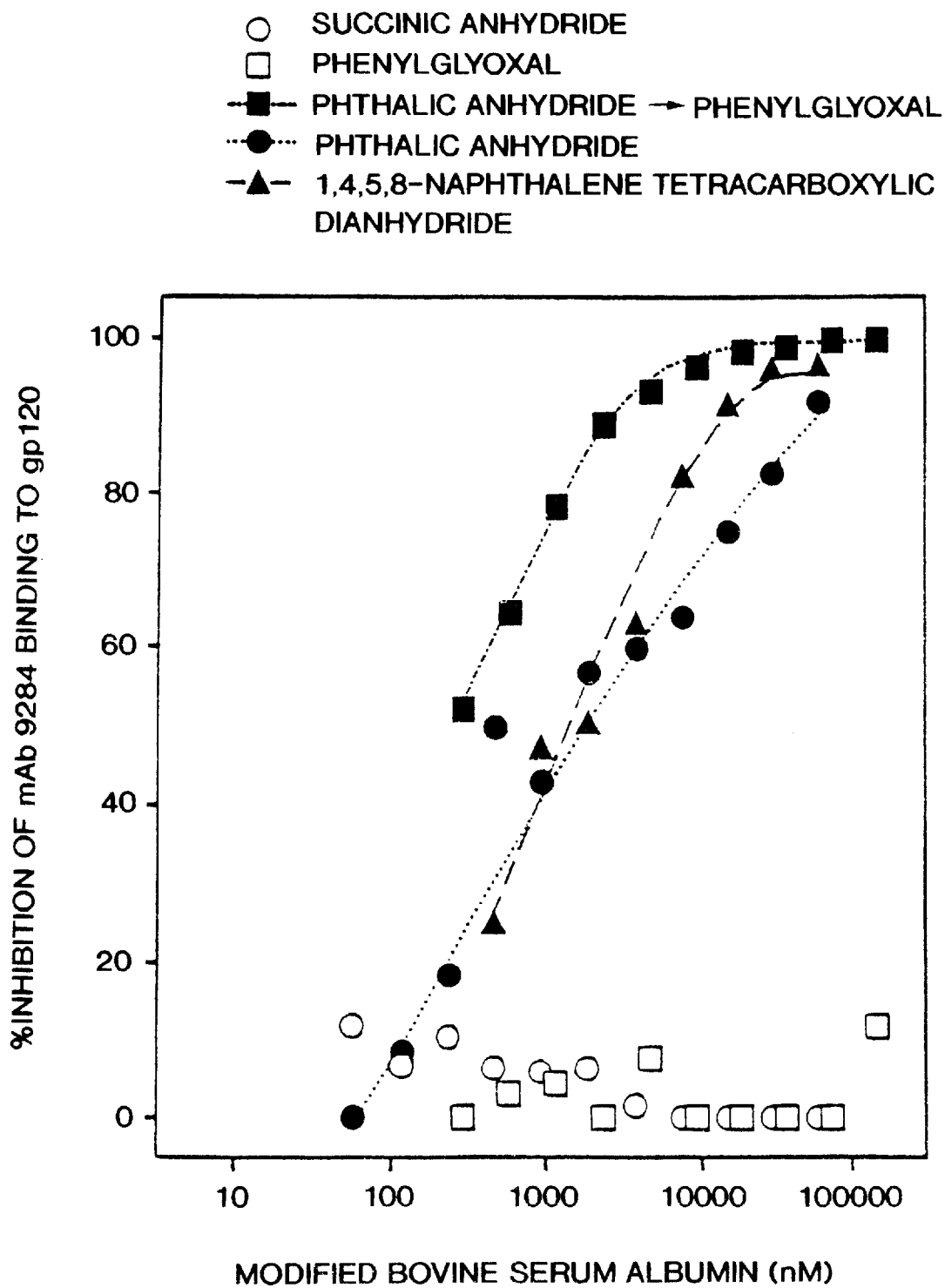
FIG. 1 is a graph showing the inhibitory effect of bovine serum albumin (BSA) treated with distinct acid anhydrides on binding to gp120 of mAb 9284 (125 ng/ml) specific for the gp120 V3 loop. The absorbance ($OD_{450}$) corresponding to bound mAb 9284 in the absence of inhibitors was 1.328.

In the present invention, several proteins, including caseins and unfractionated bovine milk, are transformed into inhibitors of HIV surface (SU) glycoprotein binding to CD4 and of HIV infection. The modified proteins bind to CD4 and block the CD4 binding site for the HIV SU glycoprotein, as suggested by their inhibitory effect on binding to CD4 of monovalent Fab fragments from mAbs specific for this site. Binding of the corresponding IgG is not blocked, suggesting a relatively low binding affinity of the modified proteins for CD4.

A protein or peptide which can be modified according to the present invention contains lysine groups. Non-limiting examples of proteins or peptides which can be utilized in the present invention include proteins and peptides from animal or human sources, such as milk (such as powdered milk), whey, casein, egg albumin, egg white, ovomucoid, human serum albumin, bovine serum albumin, rabbit serum albumin, hemoglobin, poly-D-lysine, polyamidoamine dendrimers and lactoglobulin, preferably beta-lactoglobulin, whey, casein and powdered milk.

Beta-lactoglobulin ("β-LG") is the most abundant globular protein of milk and the major protein component of whey (2–4 g/l) (Phillips, L. G. Whitehead, D. M. and Kinsella, *J. Structure-function Properties of Food Proteins*, Academic Press, San Diego, (1994)). As discussed hereinafter, beta-lactoglobulin treated with 3-hydroxyphthalic anhydride, for example, blocks the binding site on CD4 for HIV and SIV, and functions as a surrogate anti-CD4 antibody. Its safety is implicit since β-LG is consumed worldwide as a component of milk products (the worldwide production of whey is approximately 86 billion kg annually) (Morr, C. V. and Ha, E. Y. W., "Whey Protein Concentrates and Isolates: Processing and Functional Properties", *Critical Reviews in Food Science and Nutrition*, 33, 431–476 (1993)) and chemical modification does not substantially alter its antigenicity. Its effectiveness in preventing not only sexual, but also perinatal transmission of HIV at birth (Levy, J. A., "The Transmission of HIV and Factors Influencing Progression to AIDS", *Am. J. Med.*, 95, 86–99 (1993) and Siena Consensus Workshop II, "Strategies for Prevention of Perinatal Transmission of HIV Infection", *Journal of Acquired Immune Deficiency Syndromes and Human Retrovirology*, 8, 161–175 (1995)), (by topical application to the mother before delivery and to the baby topically and perhaps orally) is amenable to evaluation in invivo models (Miller, C. J. et al., "Genital Mucosal Transmission of Simian Immunodeficiency Virus: Animal Model for Heterosexual Transmission of Human Immunodeficiency Virus", *J. Virol*, 63, 4277–4284 (1989); Fazely, F. et al, "Simian Immunodeficiency Virus Infection via Amniotic Fluid: A Model to Study Fetal Immunopathogenesis and Prophylaxis", *J. AIDS*, 6, 107–114 (1993); Baba, T. W. et al., "Mucosal Infection of Neonatal Rhesus Monkeys with Cell-free SIV. AIDS", *Res. Hum. Retroviruses*, 10, 351–357 (1994) and Baba, T. W. et al., "Pathogenicity of Live, Attenuated SIV After Mucosal Infection of Neonatal Macaques", *Science*, 267, 1820–1825 (1995)) and in human clinical trials.

The protein or peptide for use in the present invention does not include collagen derived proteins or peptides, such as gelatin and does not include natural or untreated soy proteins (soy protein is a vegetable protein) However, soy protein treated with a detergent (for example, sodium dodecyl sulfate (SDS); 10 mg/ml) can be converted into an antiviral compound ($ID_{50}=0.5$ μg/ml). Other detergents for treating soy protein are listed in Table 4 hereinbelow. Results of treating a soy protein with some detergents are set forth in Table 5 hereinbelow.

The aromatic acid anhydride compound which modifies the protein or peptides according to the present invention includes compounds of the formula

[structure shown: benzene ring with substituents R², R³, R², R¹ and anhydride group]

wherein R¹, R², R³ and R⁴ are independently H, —OH, —COOH, halogen or the group $$R^5-\overset{O}{\underset{\|}{C}}-,$$

wherein $R^5$ is a halogen, and wherein at least one of $R^1$, $R^2$, $R^3$ and $R^4$ is not hydrogen.

The aromatic acid anhydride compound is preferably selected from the group consisting of trimellitic anhydride (1,2,4-benzenetricarboxylic anhydride), trimellitic anhydride chloride and 3-hydroxyphthalic anhydride.

The composition of the present invention binds to CD4 cell receptors and preferably binds to the HIV-1 or HIV-2 binding sites on CD4 cell receptors.

It is preferred to add 0.1 to 100 grams and preferably 1 to 10 grams of the aromatic acid anhydride compound per gram of the protein or peptide dissolved in an appropriate buffer, e.g., a phosphate buffer or a carbonate buffer.

The contacting of the protein or peptide and the aromatic acid anhydride compound is preferably carried out at a temperature of 0° C. to 50° C., more preferably 15° C. to 30° C. for 15 to 720 minutes, more preferably for 30 to 180 minutes at a pH of 5 to 11, more preferably 6 to 9.

The contacting of the protein or peptide and the arginine modifying agent is preferably carried out at a temperature of 37° C. for 2 hours at a pH of 8.5.

The results presented herein show the use of the present invention for the production of anti-HIV-1 and anti-HIV-2 agents for blocking the CD4 binding site for the virus, inexpensively and on a large scale from a commonly available source, such as powdered non-fat bovine milk—a pasteurized product with a well established safety record and from milk-derived proteins such as casein and lactoglobulins.

The development of CD4 binding compounds which effectively inhibit HIV-1 (or HIV-2) replication was the result of serendipity. Attempts to develop modified proteins preferentially binding to the gp120 V3 loop by dual modification of lysine residues, i.e., by introduction of both acidic and hydrophobic groups, proved to have limited success.

After synthesizing the first CD4 blocking anti-HIV-1 agents, using BSA as protein and phthalic anhydride as a lysine modifying reagent, a series of 27 additional commercially available reagents was used by applicants to modify BSA and the biological properties of the resulting compounds were investigated. The corresponding results established that three derivatives of phthalic anhydride (compounds 6, 7 and 8 in Table 1 herein) were the most effective in converting BSA into an inhibitor of gp120-CD4 association.

The blocking of CD4 by the modified proteins prevented not only gp120, but also HIV-1 binding to this receptor molecule. It is seen in Table 1 herein that the structurally related compounds 9, 11 and 12, as well compound 13, in which the benzene ring was replaced by a cyclohexane ring, were all less effective in this respect. Similarly, other aromatic anhydrides and a number of aliphatic anhydrides, as well as other compounds listed in Table 1, were also much less effective. After establishing this structure-activity relationship, proteins other than BSA were treated by selected lysine modifying reagents. Similar results to those reported for BSA were obtained with HSA.

In additional experiments, bovine casein and β-lactoglobulin were modified and shown to be convertible into potent inhibitors of gp120-CD4 binding. Considering the possibility of a wide application of modified casein for anti-HIV-1 prophylaxis, additional experiments were carried out with an even more accessible source, namely low fat powdered milk containing about 80% casein (McKenzie, H. A., (1971), "Whole casein: Isolation, Properties, and Zone Electrophoresis", In: *Milk Proteins Chemistry and Molecular Biology*, Vol. II., H. A. McKenzie (ed.), pp 87–116. Academic Press, New York). The use of milk for this purpose had several additional advantages: (1) preparations of chemically modified casein were difficult to sterilize by filtration (this problem did not occur with modified milk); (2) powdered milk is less expensive and more accessible than either BSA, HSA or casein; (3) both HSA and BSA would have to undergo virus inactivation processes in order to become licensed for human use. This problem does not arise with bovine milk and with milk-derived proteins such as casein and lactoglobulins.

Two additional commonly available food proteins, gelatin and soy protein, were also chemically modified [gelatin contains lysine and hydroxylysine (Alberts, B., Bray, D., Lewis, J., Raff, M., Roberts, K., Watson, J. D., (1983), *The Molecular Biology of the Cell*, Garland Publishing, Inc., New York, pp. 693–701)], but the resulting products did not have any detectable anti-HIV-1 activity. However, when a soy protein was treated in the presence of a detergent (emulsifier), a compound with anti-HIV-1 activity was generated.

Human IgG and transferrin appeared to be less suitable for the development of anti-HIV agents in comparison with serum albumins and milk proteins.

Thus, the development of modified proteins blocking the CD4 cell receptor for HIV depends on the appropriate selection of both the protein (or peptide) source and of the modifying reagent. In this respect, it is noted that acylation of milk proteins has been already applied by the food industry to prepare proteins with desirable physical properties (Phillips, L. G., Whitehead, D. M., and Kinsella J., (1994), *Structure Function Properties of Food Proteins*, Academic Press, San Diego).

Targeting antiviral agents to cell receptors rather than to the virus itself, appears to offer advantages, especially in the case of HIV-1, known to undergo rapid mutations reflected in the hypervariability of the envelope glycoproteins, resulting in changes of antigenicity. Targeting of the antiviral compounds to CD4 also widens the potential application to HIV-2 and SIV, assuming in the latter case that the modified proteins will bind to monkey CD4 as well as they do to human CD4 having an approximately 90% sequence homology with non-human primate CD4 molecules (Fomsgaard et al., (1992), supra).

Binding to CD4 of polyanions, including dextran sulfate (DS) and heparin (HP), and their inhibitory activity on infection by HIV-1 has been reported (Lederman, S., Gulick, R., and Chess, L., (1989), "Dextran Sulfate and Heparin Interact with CD4 Molecules to Inhibit the Binding of Coat Protein (gp120) of HIV", *J. immunol.*, 143, 1149–1154); Parish, C. R., Low, L., Warren, H. S., and Cunningham, A.

L., (1990), "A Polyanion Binding Site on the CD4 molecule. Proximity to the HIV-gp120 Binding Region," *J. Immunol*, 145, 1188–1195). Neither DS nor HP, used at a 250-fold weight excess over trimellitic anhydride chloride-treated BSA, failed to inhibit the binding of the latter to CD4, suggesting that the affinity of the polyanions to CD4 is much lower than that of the proteins modified by appropriate aromatic acid anhydrides. Yet these sulfated polysaccharides, despite their toxicity when taken internally, have been contemplated for clinical trials for prevention of HIV-1 sexual transmission (Taylor, (1994), supra).

Milk proteins modified by appropriate aromatic acid anhydrides which are much more effective inhibitors of gp120-CD4 binding, have low in vitro cytotoxicity (>1000 μg/ml) and would be much less expensive, appear to be superior candidates for consideration in clinical trials. The anti-HIV-1 activity of HSA modified by formaldehyde or aliphatic acid anhydrides has also been described (Jansen, R. W., Molema, G., Pauwels, R., Schols, D., De Clerq, E., and Meijer, D. K. F. (1991), "Potent in vitro anti-human immunodeficiency Virus-1 activity of Modified Human Serum Albumins", *Molec. Pharmacol*, 39, 818–823: Takami, M., Sone, T., Mizumoto, K., Kino, K., and Tsunoo, H. (1992), "Maleylated Human Serum Albumin Inhibits HIV-1 infection in Vitro", *Biochem. Biophys. Acta.*, 1180, 180–186). These modified proteins only partly inhibited HIV-1 binding to cells at concentrations that were 100× higher than the $ED_{50}$ values for inhibition of CPE. Their mechanism of action was ascribed to inhibition of syncytium formation (fusion). Thus, the properties of the modified albumins differ from proteins treated by aromatic acid anhydrides described herein which inhibit HIV-1 mediated fusion at considerably higher concentrations than gp120-CD4 binding (see Table 2 herein).

A particularly preferred modified protein according to the present invention is bovine beta-lactoglobulin treated with 3-hydroxyphthalic anhydride (3HP-β-LG) or bovine beta-lactoglobulin treated with 1,2,4-benzenetricarboxylic anhydride (=trimellitic anhydride) or with trimellitic anhydride chloride. Bovine beta-lactoglobulin treated with aliphatic cis-aconitic anhydride had only 1/120 of the activity of 3HP-β-LG in assays measuring the inhibition of HIV-1 gp120 binding to CD4.

In the method of the present invention for preventing HIV-1 infection or HIV-2 infection in a human, a pharmaceutically effective amount of the modified protein or peptide described hereinabove is administered to a human. It is preferred that the composition be administered to an appropriate region of the human body and local administration is most preferred.

The phrase "administration to an appropriate region of the human body" includes, for example, application of the composition of the present invention to regions of the human body which come into close contact with another human body, for example, application to the male or female genitalia if the method is intended to prevent transmission of HIV-1 or HIV-2 during sexual intercourse, and application to the vagina or to a baby's epidermis if the method is intended to prevent transmission of HIV-1 or HIV-2 during childbirth.

The term "local administration" includes any method of administration in which the activity of the composition of the present invention is substantially confined to the region of the human body to which it is applied, i.e., vaginal, rectal or topical administration.

The present invention thus provides a method of preventing vaginal transmission of HIV-1 or HIV-2, either during sexual intercourse or during childbirth (vaginal delivery), by vaginal administration, such as by administering a cream, ointment, lotion, jelly, solution, emulsion or foam formulation containing a pharmaceutically effective anti-HIV-1 or anti-HIV-2 amount of the composition of the present invention, either alone or in combination with a pharmaceutically acceptable carrier, excipient or diluent.

The present invention also therefore relates to a method of preventing transmission of HIV-1 or HIV-2 to a newborn baby by topically administering to the mother before childbirth and to the baby soon after childbirth a pharmaceutically effective anti-HIV-1 or anti-HIV-2 amount the composition of the present invention, either alone or in combination with a pharmaceutically acceptable carrier, excipient or diluent.

The present invention is also directed to a contraceptive device (for example, a male or female condom, a contraceptive diaphragm or a contraceptive sponge, for example, a polyurethane foam sponge), for the prevention of pregnancy, the improvement comprises said device having applied thereto an anti-HIV-1 or anti-HIV-2 effective amount of the composition of the present invention.

The present invention also relates to a pharmaceutical composition comprising, as active ingredients: (i) a pharmaceutically effective anti-HIV-1 or anti-HIV-2 amount of the composition of the present invention and (ii) an effective spermicidal amount of one or more spermicidal agents, for example, nonoxynol-9, benzalkonium chloride, menfegol, gossypol, chlorohexidine and "BETADINE" (povidone-iodine), alone or in association with at least one pharmaceutically acceptable carrier, excipient or diluent.

The present invention is further directed to a pessary or tampon for vaginal administration, wherein the tampon or pessary comprises, as an active ingredient, a pharmaceutically effective anti-HIV-1 or anti-HIV-2 amount of the composition of the present invention, alone or in combination with one or more pharmaceutically acceptable carriers, excipients or diluents.

The composition of the present invention, especially involving a bovine beta-lactoglobulin treated with an aromatic acid anhydride compound, preferably in the form of a conjugate with polyethylene glycol, can be administered to a human patient (preferably parentally administered) to (1) suppress programmed cell death (apoptosis) resulting from cell-to-cell transmission of HIV which leads to apoptosis of bystander T cells. (Maldarelli, F., Sato, H., Berthold, E., Orenstein, J., and Martin, M. A., "Rapid induction of apoptosis by cell-to-cell transmission of human immunodeficiency virus type 1", *J. Virol.*, 69, 6457–6465 (1995)); (2) suppress allogeneic organ transplant rejection and to suppress autoimmune diseases. (Chace, J. H., Cowdery, J. S., and Field, E. H., "Effect of anti-CD4 on CD4 subsets. I. Anti-CD4 preferentially deletes resting, naive CD4 cells and spares activated CD4 cells", *J. Immunol.*, 152, 405–412 (1994); Finck, B. K., Chan, B., and Wofsy, D., "Interleukin 6 promotes murine lupus in NZB/NZW F1 mice", *J. Clin. Invest.*, 94, 585–591 (1994); Hayashi, Y., Haneji, N., Hamano, H., and Yanagi, K., "Transfer of Sjogren's syndrome-like autoimmune lesions into SCID mice and prevention of lesions by anti-CD4 and anti-T cell receptor antibody treatment", *Eur. J. Immunol.*, 24, 2826–2831 (1994); Hutchings, P., Parish, N., O'Reilly, L., Dawe, K., Roitt, I. M., and Cooke, A., "The regulation of autoimmunity through CD4+T cells", *Autoimmunity*, 15 (suppl), 21–23 (1993); Connolly, K., Roubinian, J. R, and Wofsy, D., "Development of murine lupus in CD4-depleted NZB/NZW mice. Sustained inhibition of residual CD4+T cells is required to suppress autoimmunity", *J. Immunol.*, 149, 3083–3088 (1992); Gilkeson, G. S., Spurney, R., Coffman, T. M., Kurlander, R., Ruiz, P., and Pisetsky, D. S., "Effect of anti-CD4 antibody treatment on inflammatory arthritis in MRL-lpr/lpr mice", *Clin. Immunol. Immunopathol.*, 64, 166–172 (1992); Roitt, I. M., Hutchings, P. R., Dawe, K. I., Sumar, N., Bodman, K. B., and Cooke, A., "The forces driving autoimmune disease", *J. Autoimmunity*, 5 (suppl A), 11–26 (1992); Hutchings, P., O'Reilly, L., Parish, N. M., Waldmann, H., and Cooke, A., "The use of a non-depleting anti-CD4 monoclonal antibody to re-establish tolerance to beta cells in NOD mice", *Eur. J. Immunol.*, 22, 1913–1918 (1992); dos Santos, R. R., Rossi, M. A., Laus, J. L., Silva, J. S., Savino, W., and Mengel, J., "Anti-CD4 abrogates rejection and reestablishes long-term tolerance to syngeneic newborn hearts grafted in mice chronically infected with Trypanosoma cruzi", *J. Exp. Med.*, 175, 29–39 (1992); Hafler, D. A., Ritz, J., Schlossman, S. F., and Weiner, H. L., "Anti-CD4 and anti-CD2 monoclonal antibody infusions in subjects with multiple sclerosis: immunosuppressive effects and human anti-mouse responses", *J. Immunol.*, 141, 131 (1988); Herzog, C., Walker, C., Pichler, W., Aeschilmann, A., Wassmer, P., Stockinger, H., Knapp, W., Riber, R., and Muller, W., "Monoclonal anti-CD4 in arthritis", *Lancet.*, 2, 1461 (1987); Herzog, C., Walker, C., Muller, W., Reiber, P., Reiter, C., Riethmuller, G., Wassman, P., Stockinger, H., Madic, 0., and Pichler, W. J., "Anti-CD4 antibody treatment of patients with rheumatoid arthritis: I. Effect on clinical course and circulating T cells", *J. Autoimmun.*, 2, 627 (1989); Walker, C., Herzog, C., Rieber, P., Riethmuller, G., Muller, W., and Pichler, J., "Anti-CD4 antibody treatment of patients with rheumatoid arthritis: II. Effect of in vivo treatment on in vitro proliferative response of CD4 cells", *J. Autoimmun.*, 2, 643 (1989); Horneff, G., Burmester, G., Emmrich, F., and Kalden, J. R., "Treatment of rheumatoid arthritis with an anti-CD4 monoclonal antibody", *Arthritis Rheum.*, 34, 129 (1991); Reiter, C., Kakavand, B., Rieber, E. P., Schattenkirchner, M., Riethmuller, G., Kruger, K., "Treatment of rheumatoid arthritis with monoclonal antibody M-T151", *Arthritis Rheum.*, 34, 525 (1991); Benjamin, R. J., and Waldmann, H., "Induction of tolerance by monoclonal antibody therapy", *Nature*, 320, 449 (1986); Mathieson, P. W., Cobbold, S. P., Hale, G., Clark, M. R., Oliveira, D. B. G., Lockwood, C. M., and Waldmann, H., "Monoclonal-antibody therapy in systemic vasculitis", *N. Engl. J. Med.*, 323, 250 (1990); Cobbold, S. P., Martin, G., Qin, S., and Waldmann, H., "Monoclonal antibodies to promote marrow engraftment and tissue graft tolerance", Nature, 323, 164 (1986); Cosimi, A. B., Burton, R. C., Kung, P. C., Colvin, R., Goldstein, G., Lifter, J., Rhodes, W., and Russell, P. S., "Evaluation in primate renal allograft recipients of monoclonal antibody to human T cell subclasses", *Transplant. Proc.*, 13, 499 (1981); Pearson, T. C., Madsen, J. C., Larsen, C. P., Morris, P. J., and Wood, K. J., "Induction of transplantation tolerance in adults using donor antigen and anti-CD4 monoclonal antibody", *Transplantation*, 54, 475 (1992); Sablinski, T., Hancock, W. W., Tilney, N. L., and Kupiec-Weglinski, J. W., "CD4 monoclonal antibodies in organ transplantation—a review in progress", *Transplantation*, 52, 579 (1991); Morel, P., Vincent, C., Cordier, G., Panaye, G., Carosella, E., and Revillard, J. P., "Anti-CD4 monoclonal antibody administration in renal transplanted patients", *Clin. Immunol. Immunopathol.*, 56, 311 (1990); Norman, D. J., Bennett, W. M., Cobanoglu, A., Hershberger, R., Hosenpud, J. D., Meyer, M. M., Misiti, J., Ott, G., Ratkovec, R., Shihad, F., Vitow, C., and Barry, J. M., "Use of OKT4A (a murine monoclonal anti-CD4 antibody) in human organ transplantation: initial clinical experience", *Transplant. Proc.*, 25, 802 (1993); Reinke, P., Miller, H., Fietze, E., Herberger, D., Volk, H.-D., Neuhaus, K., Herberger, J., v. Baehr, R., and Emmrich, F., "Anti-CD4 therapy of acute rejection in long-term renal allograft recipients", *Lancet*, 338, 702 (1991); and Jonker, M., Neuhaus, P., Zurcher, C., Fucello, A., and Goldstein, G., "OKT4 and OKT4A antibody treatment as immunosuppression for kidney transplantation in rhesus monkeys", *Transplantation*, 39, 247 (1985)).

Autoimmune diseases which may be treated by the present invention include the following: Hashimoto's thyroiditis, systemic lupus erythematosus, Goodpasture's syndrome, pemphigus, Graves' disease, myasthenia gravis, insulin resistance, autoimmune hemolytic anemia, and autoimmune thrombocytopenic purpura.

Other autoimmune conditions which may be treated by the present invention include the following: rheumatoid arthritis, scleroderma, polymyositis, pernicious anemia, idiopathic Addison's disease, glomerulonephritis, bullous pemphigoid, Sjogren's syndrome, diabetes mellitus, and adrenergic drug resistance.

The present invention further concerns a pharmaceutical composition for topical administration comprising a pharmaceutically effective anti-HIV-1 or anti-HIV-2 amount of the composition of the present invention and at least one pharmaceutically acceptable topical carrier, excipient or diluent, to form an ointment, cream, gel, lotion, paste, jelly, spray or foam.

The amount of the active ingredient (composition of the present invention) for use in the present invention will vary, not only with the particular modified proteins or peptides, but also with the route of administration, and the age and condition of the human to which the composition is administered and will be ultimately determined by the discretion of the attendant physician. In general, however, a suitable concentration of the composition in a topical dosage form is up to 2,000 micrograms per milliliter, preferably between 200 and 1000, and more preferably 200 to 400, micrograms per milliliter.

While it is possible that the active ingredient may be administered as the raw composition, it is preferable to present the active ingredient in conjunction with a pharmaceutically acceptable excipient, diluent or carrier, as a pharmaceutical formulation.

The invention thus further provides for the use of a pharmaceutical formulation comprising the active ingredient together with one or more pharmaceutically acceptable carriers, excipients or diluents therefor and, optionally, other prophylactic ingredients. The carrier(s), excipient(s) or diluent(s) must be "acceptable" in the sense of being compatible with the other ingredients of the formulation and not deleterious to the recipient therefor.

Pharmaceutical formulations include those suitable for vaginal, oral, rectal, nasal or topical (including buccal and sub-lingual) administration. The formulations may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions, solutions or emulsions (liquid formulations) containing in addition to the active ingredient, such carriers as are known in the art to be appropriate. These formulations are useful to protect not only against sexual transmission of HIV, but also to prevent infection of a baby during passage through the birth canal. Thus the vaginal administration can take place prior to sexual intercourse, during sexual intercourse, immediately prior to childbirth or during childbirth.

As a vaginal formulation, the active ingredient may be used in conjunction with a spermicide and may be employed with condoms, diaphragms, sponges or other contraceptive devices.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspension, solutions, emulsions, syrups or elixirs, or may be presented as a dry product for constitution with water or other suitable vehicle before use.

Depending on the protein employed in the composition which is administered, the composition according to the present invention may be administered intravenously, for example, when a treated hemoglobin is employed.

Although the dosage may vary depending on several factors, such as the age of the patient and the route of administration, in the case of oral administration to an adult human patient, the composition of the present invention may normally be administered at a total daily dose of 1 to 5000 mg, preferably from 5 to 300 mg, in a single dose or in divided doses. In the case of intravenous administration, the dose may be 0.1 to 100 mg and preferably 0.5 to 30 mg, with the dose being administered one to three times a day.

The composition of the present invention can also be employed as a food additive to inhibit the spread of the virus in the intestinal tract and possibly at other sites.

Liquid preparations for oral or vaginal administration may contain conventional additives such as suspending agents, emulsifying agents, non-aqueous vehicles (which may include edible oils) or preservatives.

For topical administration to the epidermis, the active ingredient may be formulated as an ointment, cream, paste, jelly, foam, gel or lotion, or as a transdermal patch for topical administration. Ointments, pastes, jellies, liquids, foams, gels and creams may, for example, be formulated with an aqueous or oil base with the addition of suitable thickening and/or gelling agents. Lotions may be formulated with an aqueous or oil base and will in general also contain one or more emulsifying agents, stabilizing agents, suspending agents, thickening agents, or coloring agents. Such topical dosage forms may be particularly useful when applied to a newborn baby of an HIV-infected mother.

Formulations suitable for topical administration in the mouth include lozenges comprising an active ingredient in a flavored base, usually sucrose and acacia or tragacanth; or pastilles comprising the active ingredient in a suitable liquid carrier.

Pharmaceutical formulations suitable for rectal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Drops may be formulated with an aqueous or non-aqueous base comprising one or more dispersing agents, solubilizing agents or suspending agents. Liquid sprays are conveniently delivered from pressurized packs.

When desired, the above described formulations adapted to give sustained release of the active ingredient may be employed.

The pharmaceutical compositions for use according to the invention may also contain other active ingredients such as spermicides as discussed above, or antimicrobial agents or preservatives.

The active ingredient may also be used in combination with therapeutic agents, for example, anti-infective agents.

EXAMPLES

The present invention will now be described with reference to the following non-limiting examples.

Reagents

The following macromolecular compounds were used for chemical modifications (sources are given in parentheses): Bovine serum albumin ("BSA"), human transferrin, casein and poly-D-lysine (M.W. 60,000) (Sigma, St. Louis, Mo.); beta-lactoglobulin (3× crystallized) from bovine whey (Sigma); human serum albumin (HSA) and IgG (The New York Blood Center, New York); gelatin (Bio-Rad Laboratories, Richmond, Calif.); polyamidoamine dendrimers (72 Å diameter, M.W. 58,000; Polysciences Inc., Warrington, Pa.); and Carnation non-fat dry milk powder (34.8% protein; local supermarket). Fluorescein isothiocyanate (FITC) and rhodamine B isothiocyanate modified BSA, respectively, were also obtained from Sigma.

Reagents for modification of lysine and arginine residues, such as 3-hydroxyphthalic anhydride, listed in Table 1 herein, were obtained from Aldrich, Milwaukee, Wis., except for FITC which was obtained from Molecular Probes, Eugene, Oreg.

The following recombinant proteins were used in ELISA assays: CD4 (Genentech, South San Francisco, Calif.); HIV-1 gp120 IIIB, HIV-2 gp105, $SIV_{mac251}$ gp120 and horseradish peroxidase (HRP)-labeled CD4 (all from Intracel, Cambridge, Mass.); HIV-1 gp120 MN and biotin-labeled CD4 (both from Agmed, Bedford, Mass.).

Monoclonal antibodies (mAbs) specific for the V3 loop of gp120 IIIB (9305), gp120 IIIB (9284) and gp120 MN (50.1) were obtained from: DuPont NEN, Boston, Mass.; Cambridge Biotech, Worcester, Mass.; and Repligen, Cambridge, Mass., respectively. MAb 588D specific for the CD4 binding site on gp120 was provided by Drs. M. K. Gorny and S. Zolla-Pazner (New York University Medical Center). The following anti-CD4 mAbs were used: anti-Leu3a, L120, L83 (Becton-Dickinson Immunocytometry Systems, San Jose, Calif.); OKT4 (OKT4a) (Ortho Diagnostics, Raritan, N.J.); ADP310, 311, 356, 357, 364 and 372 (MRC AIDS Directed Program Reagent Repository, London); 13B 8.2 and BL4 (Immunotech, Inc., Westbrook, Me.); CLB-T4 clone 159 (Research Diagnostics, Flanders, N.J.); VIT4 (Oncogene Science, Inc., San Diego, Calif.); and Q4120 (Sigma). Normal mouse IgG isotypes were from Cappel-organon Teknika, Durham, N.C.

Additional reagents were as follows: rabbit anti-BSA antiserum (Cappel); HRP-labeled streptavidin (Amersham, Arlington Heights, Ill.) and HRP-labeled second antibodies against mouse, rabbit and sheep IgG, and against the Fab fragment from mouse IgG, respectively (Sigma).

Fab fragments from mAb Q4120 were prepared using a kit from Pierce, Rockford, Ill.

Purified HIV-1 IIIB virus was obtained from Advanced Biotechnologies, Inc., Columbia, Md.

Antisera against bovine whey proteins were obtained from Accurate Chemical and Scientific Corporation, Westbury, N.Y.

Example 1
Chemical Modification of Proteins and other Macromolecules

The compounds such as beta-lactoglobulin were dissolved in 0.1 M phosphate pH 8.5 at a final concentration of 20 mg/ml. Acid anhydrides (Table 1) were dissolved in dimethylformamide at the highest possible concentration, for example, 200 mg/ml for beta-lactoglobulin. Aliquots (5) of the anhydride solutions were added in five 12 minutes intervals to th e dissolved macromolecular compounds while the pH was maintained at 8.5. The final concentration of the acid anhydrides in the mixtures was 10 mg/ml. The mixtures were kept for another 1 hour at 25° C. and then extensively dialyzed against phosphate buffered saline (PBS) (0.15M NaCl, 10 mM phosphate, pH 7.4). The dialyzed solutions were sterilized by filtration through 0.45 µm syringe filters (Acrodisc; Gelman Sciences, Ann Arbor, Mich.). In some cases, the modification procedure had to be modified because of problems with solubility of the reagents and/or the reaction products (reagents 10, 23, Table 1). In those cases, the reagents were dissolved in dimethyl sulfoxide (DMSO) and the reaction was carried out in 50% DMSO. Casein was first dissolved in 0.1 N NaOH and the pH was subsequently adjusted to pH 8.5. The modification of gelatin was carried out at pH 9.0 at final protein and reagent concentrations of 2.5 mg/ml, respectively. Treatment with 4-carboxybenzaldehyde was done in 0.1 M $NaHCO_3$ adjusted to pH 9.0. Treatment with 2,4,6-trinitrobenzenesulfonic acid (TNBS) was carried out at pH 9.0 in phosphate buffer for 3 hours at 25° C. and the reagent was originally dissolved in $H_2O$.

Some of the proteins treated to modify lysine residues were subsequently treated with phenylglyoxal specific for arginine (Lundblad, (1991)), *Chemical Reagents For Protein Modification*, CRC Press, Boca Raton, Fla. $NaHCO_3$ (8.4 mg/ml) was added to the modified proteins in PBS and the pH was adjusted to and maintained at 8.5. Phenylglyoxal (20 mg/ml) was added and the temperature was maintained at 37° C. for 2 hours. Subsequently, the mixture was dialyzed against PBS. In control examples, proteins whose lysines had not been modified were treated in the same way. In some experiments, treatments with acid anhydrides and phenylglyoxal were consecutive, omitting the intermediate dialysis step and addition of .$NaHCO_3$.

BSA was reduced and alkylated as described in Neurath, A. R. and Strick, N., (1980), "Antibodies as Immunological Probes for Studying the Denaturation of HBsAg", *J. Med. Virol.* 6, 309–322. BSA (20 mg/ml) was treated with trypsin (400 µg/ml) in 0.1 M phosphate pH 8.0 for 4 hours at 37° C. After addition of soybean trypsin inhibitor, the cleavage products were treated with trimellitic anhydride as described above and dialyzed using 500 M.W. cut off membranes (Spectra/Por, Los Angeles, Calif.).

Protein concentrations were determined using the BCA Protein Assay Reagent Kit (Pierce). To quantitate lysine (terminal $NH_2$ groups) in the original and the chemically modified preparations, they were treated with TNBS as described above and dialyzed against 0.1 M $NaHSO_3$. The absorbances at 420 nm ($OD_{420}$) of the dialyzed preparations and their appropriate dilutions in 0.1 M $NaHSO_3$ were measured. The concentration of lysine was determined from calibration curves relating $OD_{420}$ values to lysine concentrations in standards. Such quantitative amount of lysine revealed that 73.2% of beta-lactoglobulin lysines were modified.

Amino acid sequences of the proteins used were obtained from the PIR-International Protein Sequence Database (George, D. G., Barker, W. C., Mewes, H.-W., Pfeiffer, F., and Tsugita, A., (1994), "The-PIR-International Protein Sequence Database", *Nucl. Acids Res.* 22, 3569–3573). The net negative electric charges of the original and modified proteins were calculated by subtracting the sum of D+E residues from the sum of K+R residues present in each sequence, considering the extent of lysine modification and the introduction of additional negative charges by the respective chemical reagents (see Table 1 herein). In the case of casein, phosphorylation of serines was considered in calculating the charges, and the mean charge of casein was calculated considering a composition of 65.7% α-, 19.3% β-, and 15% K-casein. The mean charge of milk proteins was calculated similarly, and is likely to be imprecise (casein represents ~80% of milk proteins) with an error of <±20%.

Product 63 in Table 2 herein was prepared by treatment with 3-hydroxyphthalic anhydride.

Product 64 in Table 2 was prepared in a similar way as Product 63, except that the final concentration of the protein was 1 mg/ml and that of the reagent was also 1 mg/ml.

Product 65 in Table 2 was prepared in a similar fashion as Product 63, except that the protein concentration was 2 mg/ml an that of the reagent was 10 mg/ml.

To prepare pyridoxal phosphate-treated β-lactoglobulin (Product 78), 200 mg of β-lactoglobulin were dissolved in 8 ml of 0.1 M sodium borate pH 8. Separately, 62 mg of pyridoxal phosphate and 62.8 mg of sodium cyanoborohydride and 4.8 mg of $NiCl_2$ were dissolved in 2 ml of 0.1 M sodium borate pH 8. The two solutions were mixed and kept for 4 hours at 25° C. and, subsequently, extensively dialyzed against phosphate-buffered saline (PBS).

To prepare p-carboxyphenylglyoxal-treated bovine serum albumin (BSA; Product 72), BSA at a final concentration of 20 mg/ml was dissolved in 0.1 M sodium carbonate buffer pH 8.5. The solution was warmed to 37° C. and 20 mg/ml of p-Carboxyphenylglyoxal were added. After incubation for 2 hours at 37° C., the solution was dialyzed against PBS.

To prepare polyethyleneglycol (PEG)-conjugated 3-hydroxyphthalic anhydride-treated β-lactoglobulin (3HP-β-LG), 50 mg of an amino derivative of PEG(MW 3350; Sigma, St. Louis, Mo.) were activated using a 5-fold molar excess (=32.7 mg) of sulfosuccinimidyl 4-[N-maleimidomethyl]cyclohexane-1-carboxylate (SMCC; Pierce, Rockford, Ill.) at a pH 9 using the protocol provided by the manufacturer. The activated derivative containing thiol-reactive groups was separated from the excess of reagents by molecular exclusion chromatography on Sephadex G-10. The activated PEG collected in the void volume fractions was reacted with an equal amount (=mass) of 3HP-β-LG in the presence of 10 mM Tris(2-carboxyethyl)-phosphine for 3 hours at 25° C. By these procedures, the three cysteines present in 3HP-β-LG were expected to be modified by PEG. The final product was dialyzed against PBS.

Example 2
Measurement of Anti-HIV Activity

MT-2 cells were infected with distinct strains of HIV-1, such as HIV-1-IIIB, (multiplicity of infection=0.0045) in the presence or absence of modified proteins. The percentage of inhibition of the nucleocapsid P24 antigen production and of the cytopathic effect (CPE) was determined as described in Jiang, S., Lin, K., and Neurath, A. R., (1991), "Enhancement of Human Immunodeficiency Virus Type 1 Infection by Antisera to Peptides from the Envelope Glycoproteins gp120/gp41", *J. Exp. Med.*, 174, 1557–1563; Jiang, S. and Neurath, A. R., (1992), "Potential Risks of Eliciting Antibodies Enhancing HIV-1 Infection of Monocytic Cells by Vaccination with V3 loops of Unmatched HIV-1 Isolates", *AIDS*, 6, 331–342). Cell fusion was measured as follows: HIV-1-IIIB infected H9 cells were labeled by 2',7'-bis-(2-carboxyethyl)-5-(and-6)-carboxyfluorescein acetoxymethyl ester (BCECF-AM; Molecular Probes, Inc., Eugene, OR) according to the manufacturer's instructions. BCECF-labeled H9/HIV-1-IIIB cells ($10^4$) were mixed with $2 \times 10^5$ uninfected MT-2 cells. After incubation in a 96 well plate at 37° C. for 1 hour, the fused and unfused labeled H9/HIV-1-IIIB cells were counted under an inverted fluorescent microscope at a 160× magnification. At least 200 BCECF-labeled cells were counted and the proportion of fused cells was determined. All experiments with HIV-1 were carried out under P2 biohazard containment levels.

Example 3
Enzyme-linked Immunosorbent Assays (ELISA)

The inhibition of gp120 -CD4 binding by graded quantities of the modified macromolecular compounds was measured by the Nenquest HIV gp120/CD4 Receptor-Drug Discovery System (DuPont NEN) using 1 ng of gp120 per test. The concentration of compounds at which gp120-CD4 binding was 50% of that observed in the absence of inhibitors ($ED_{50}$) was determined from linear regressions of logit-log (dilution) plots (Ritchie, D. G., Nickerson, J. M., and Fuller, G. M., (1983), "Two simple Programs for the Analysis of Data from Enzyme-linked Immunosorbent Assays (ELISA) on a Programmable Fesk-Top Calculator", In: *Methods in Enzymology*., Vol. 92. Immunochemical Techniques, Langone, J. J. and Van Vunakis, H. (eds.), pp. 577–588, Academic Press, New York).

For all other ELISA tests, wells of 96-well polystyrene plates (Immulon II; Dynatech Laboratories, Inc., Chantilly, Va.) were coated with recombinant proteins (CD4 or envelope glycoproteins from distinct primate immunodeficiency viruses; 100 ng protein/well) or with chemically modified proteins (3 μg/well) in 0.1 M Tris HCl, pH 8.8 overnight at 4° C.

The wells were washed with 0.14 M NaCl, 0.01 M Tris, 0.01% sodium merthiolate, pH 7.2 (TS) and postcoated with TS-BG [a mixture of BSA and gelatin (10 and 2.5 mg/ml, respectively) in TS]. The postcoating solution was removed after 2 hours at 25° C. and the plates were stored at 4° C.

Reagents specifically binding to the respective proteins (mAbs, antisera, biotinylated CD4) were usually added to the wells overnight at 25° C. The antibodies were diluted in a mixture of fetal bovine serum and goat serum (9:1) containing 0.1% Tween 20 and adjusted to pH 8 (FG-T). Other reagents were diluted in TS-BG. When wells coated with modified BSA were used, BSA was omitted from the diluents. Excess of the reagents was removed and the plates were washed with TS. Subsequently, HRP-labeled probes (second antibodies in TS containing 0.1% Tween 20 and 10% serum of the same species as were the second antibodies, or streptavidin in TS containing 0.25% gelatin), diluted 1:1000 from the commercial stock solutions, were added to the wells. After incubation for 2 hours at 37° C., the wells were washed with TS, and bound HRP was quantitated using a kit from Kirkegaard & Perry Laboratories, Inc. (Gaithersburg, Md.). Absorbance at 450 nm ($OD_{450}$) was measured using an MR600 microplate reader (Dynatech).

Example 4
Binding of Cells to Magnetic Beads Coated with β-LG and 3HP-β-LG, Respectively.

β-LG and 3HP-β-LG (10 mg/ml), respectively, were reduced in 10 mM phosphate, 1 mM EDTA, pH 5.0 containing 1 mM Tris(2-carboxyethyl)phosphine (Pierce, Rockford, Ill.) for 45 minutes at 25° C., followed by pH adjustment to 7.5 by 1 N NaOH. Subsequently, 1 mg/ml of N-iodoacetyl-N'-biotinyl hexylenediamine (Pierce) was added. After 2 hours at 25° C., the biotinylated proteins were dialyzed against PBS.

Magnetic beads [5 mg in 1 ml PBS containing 1 mg/ml BSA (PBS-BSA); BioMag Streptavidin, PerSeptive Diagnostics, Cambridge, Mass.] were mixed with 200 μg of biotinylated β-LG and 3HP-β-LG, respectively, overnight at 25° C. The beads were washed 10 times with PBS-BSA and stored at 4° C. (concentration 5 mg/ml). Binding of cells ($5 \times 10^5$) to magnetic beads (250 μg) was studied as described in Neurath, A. R., Strick, N. and Sproul, P., "Search for Hepatitis B Virus Cell Receptors Reveals Binding Sites for Interleukin 6 on the Virus Envelope Protein", *J. Exp. Med.*, 175, 461–469 (1992), except that chicken serum (10%) instead of BSA was added to the diluent for the assays. HeLa and CD4+ HeLa cells were grown in MEM and DMEM medium+500 μg/ml Geneticin (GIBCO BRL, Gaithersburg, Md.), respectively, each supplemented with 10% fetal bovine serum.

Example 5
Inhibition of Sperm Binding to PBMC By 3HP-β-LG

It has been reported that HLA-II DR molecules act as sperm receptors, and suggested that sperm binding and penetration into PBMC may contribute to sexual transmission of HIV-1 (Ashida, E. and Scofield, V. L., "Lymphocyte Major Histocompatibility Complex Encoded Class II Structures May Act as Sperm Receptors", *Proc. Natl. Acad. Sci. U.S.A.*, 84, 3395–3399 (1987) and Scofield, V. L. et al., "Binding of Sperm to Somatic Cells Via HLA-DR. Modulation by Sulfated carbohydrates", *J. Immunology*, 148, 1718–1724 (1992)). 3HP-β-LG inhibited sperm binding to PBMC, in agreement with the reported inhibitory effect of anti-CD4 mAb OKT4a (Ashida and Scofield, supra).

Binding of sperm to PBMC was determined as described by Ashida and Scofield, supra. $2 \times 10^5$ PBMC were cocultured with $2 \times 10^6$ washed sperm in 96-well round bottom plates at 37° C. for 2 hours in the presence or absence of 3HP-β-LG. The cell and sperm mixture was fixed with 0.1% glutaraldehyde and stained with a blue fluorescent DNA-binding dye, DAPI (Sigma, St. Louis, Mo.). Aliquots (5 μl) from each well were transferred to glass slides and examined under simultaneous untraviolet and bright-field Nomarski illumination. Cells that had one or more attached or penetrated sperm heads were scored as positive.

Figure 20:
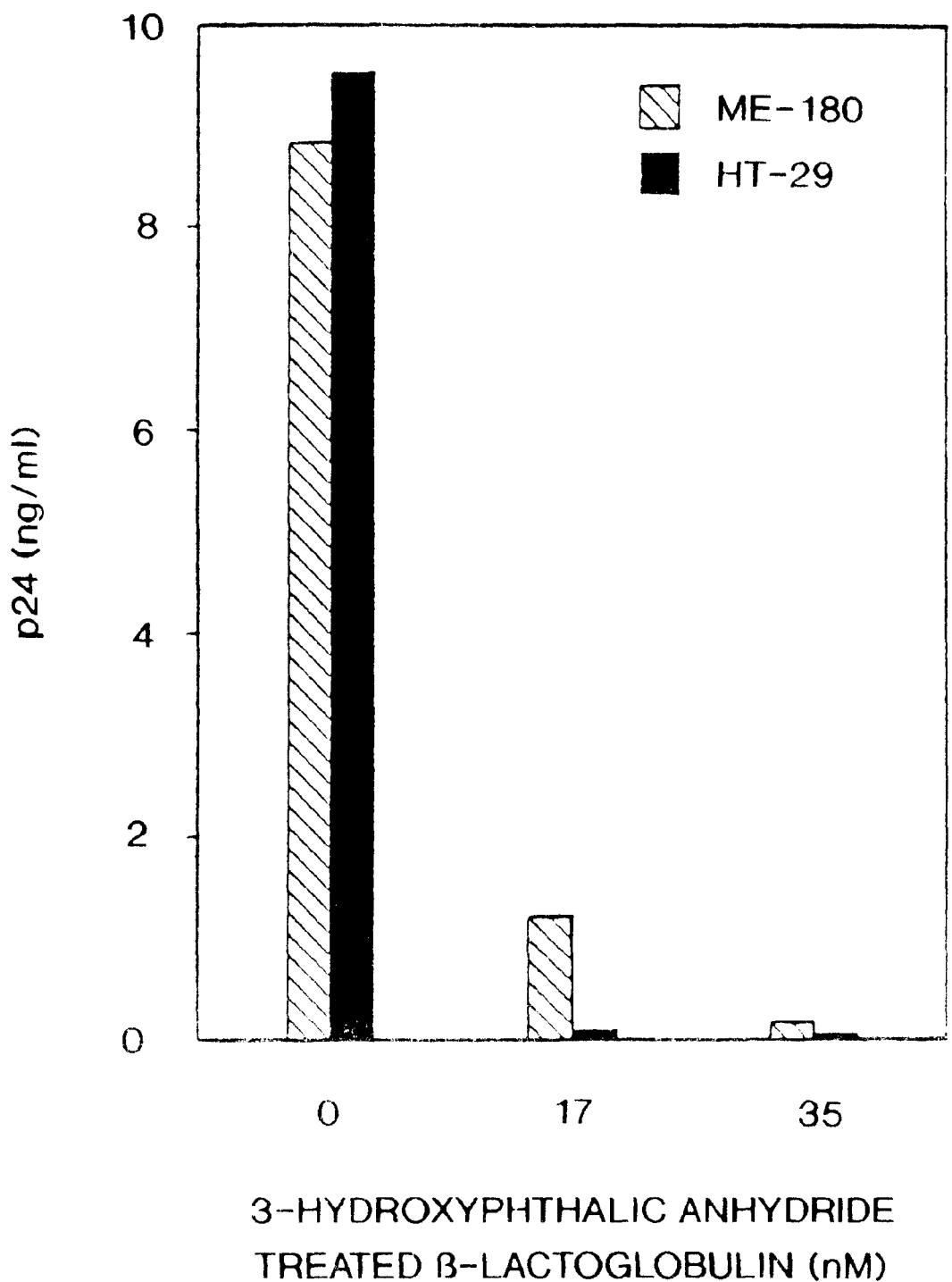
FIG. 20 is a graph showing the inhibition of HIV-1 uptake in both colonic and cervix-derived epithelial cell lines.

CD4 cells in the rectal and genital tract mucosae may play a role in HIV-1 transmission (Fantini, J., Cook, D. G., Nathanson, N., Spitalnik, S. L. and Gonzalez-Scarano, F. "Infection of Colonic Epithelial Cell Lines by Type 1 Human Immunodeficiency Virus is Associated with Cell Surface Expression of Galactosylceramide, a Potential Alternative gp120 Receptor", *Proc. Natl. Acad. Sci. U.S.A.*, 90, 2700–2704 (1993); Furuta, Y. et al., "Infection of Vaginal and Colonic Epithelial Cells by the Human Immunodeficiency Virus Type 1 is Neutralized by Antibodies Raised Against Conserved Epitopes in the Envelope Glycoprotein gp120", *Proc. Natl. Acad. Sci. U.S.A.*, 91, 12559–12563 (1994); and Phillips, D. M., Tan, X., Pearce-Pratt, R. and Zacharopoulos, V. R., "An Assay for HIV Infection of Cultured Human Cervix-derived Cells", *J. Virol. Meth.*, 52, 1–13 (1995)). Consequently, blockade of cellular CD4 might not be sufficient for anti-HIV-1 prophylaxis. 3HP-β-LG inhibited HIV-1 uptake into both colonic and cervix-derived epithelial cell lines (FIG. 20).

The uptake of HIV-1 by epithelial cell lines was determined as follows: human colonic adenocarcinoma HT-29

(Fantani et al, supra) and cervix-derived ME-180 (Phillips et al, supra) cells (4 ml; 2.5×10$^5$ cells/ml grown in McCoys 5A and RPMI 1640 medium, respectively) were placed into wells of a 6-well plate. After incubation at 37° C. for 24 hours, supernatants were removed. 3HP-β-LG at different concentrations in the respective media (2 ml) and 2 ml of HIV-1 IIIB (MOI=0.02) were added to the wells. After incubation at 37° C. for 16 hours, the cells were washed 4 times with medium without serum. Then, trypsin (4 ml; 0.25 mg/ml) was added at 37° C. for 2 minutes and the cells were mixed with 4 ml of medium containing 10% fetal bovine serum. The cells (10$^6$) were washed twice and lysed with 1 ml of 5% Triton X-100 and assayed for p24 antigen.

Results

1. Some Proteins Modified by Aromatic Acid Anhydrides Inhibit the Binding to HIV-1 gp120 of Monoclonal Antibodies Specific for the V3 Loop Bovine serum albumin (BSA) was treated with acid anhydrides listed in Table 1 and with phenylglyoxal to modify lysine (K) and arginine (R) residues, respectively (Lundblad, (1991), supra). Other commonly available and inexpensive proteins (human serum albumin (HSA), rabbit serum albumin (RSA), casein, human IgG and transferrin and gelatin) were also modified with selected acid anhydrides.

Binding of the treated proteins to the V3 loop of HIV-1 gp120 (subtypes IIIB and MN) was determined indirectly by measuring their inhibitory effect on binding to gp120 of mAbs specific for the V3 loop (Neurath, A. R., Haberfield, P., Joshi, B., Hewlett, I. K., Strick, N., and Jiang, S., (1991), "Rapid Prescreening for Antiviral Agents Against HIV-l Based on their Inhibitory Activity in Site-directed Immunoassays I. The V3 loop of gp120 as Target", Antiviral Chem. Chemother., 2, 303–312; Neurath, A. R., Strick, N., Haberfield, P., and Jiang, S., (1992), "Rapid Prescreening for Antiviral Agents Against HIV-1 Based on their Inhibitory Activity in Site-directed Immunoassays. II. Porphyrins Reacting with the V3 loop of gp120", Antiviral Chem. Chemother., 3, 55–63). BSA modified by acid anhydrides 5, 6, 7, 10, 14, 15, 18, and 23 (see Table 1 herein) inhibited the binding to gp120 of mAb 9284, recognizing residues 1–12 in the V3 loop-derived sequence NNTRKKIRIQRG-PGRAFVTIGK (SEQ ID NO: 1). Thus, with the exception of compound 18, only aromatic acid anhydride treated BSA had inhibitory activity. Representative results of these experiments are shown in FIG. 1.

BSA treated with compounds 26, 27, and 28 was also inhibitory. On the other hand, treatment with 4-carboxybenzaldehyde and phenylglyoxal, respectively, failed to convert BSA into an inhibitor of gp120-mAb 9284 binding. HSA, RSA and casein, respectively, treated with selected aromatic acid anhydrides, also became inhibitory, while modified human IgG and transferrin had only marginal activity, and treated gelatin conspicuously lacked any activity in this and other assay systems.

Binding to gp120 IIIB of mAb 9305, specific for residues 8–22 of the above sequence, was not inhibited by any of the modified proteins blocking the binding of mAb 9284 to gp120 IIIB. Similarly, the binding of mAbs 50.1 and 59.1 to gp120 MN was not inhibited. Thus, the chemically modified proteins described here behaved differently from several low molecular mass compounds with anti-HIV-1 activity which inhibited the binding to gp120 of distinct HIV-1 subtypes of all anti-V3 loop specific antibodies tested so far (Neurath et al, (1991), supra; Neurath et al, (1992), supra; Neurath, A. R., Strick, N., Lin, K., Debnath, A. K., and Jiang, S. (1994), "Tin protoporphyrin IX Used in Control of Heme Metabolism in Humans Effectively Inhibits HIV-1 Infection", Antiviral Chem. Chemother., 5, 322–330).

These results indicate that: (1) the observed inhibitory properties of the chemically modified proteins depend on the reagents used for modification and on the presence of benzene rings in their structure; and on the proteins selected for modification; (2) the inhibitory effect of the modified proteins on HIV-1 infection (see Table 2 hereinafter, columns 2–4) cannot be related to their interaction with the V3 loop since some of the compounds inhibit HIV-1 infection while they do not affect gp120 IIIB—mAb 9284 binding and (3) the observed differences between the modified proteins with respect to binding to the V3 loop cannot be explained by the extent of lysine residue modification (Table 2, column 1) and, consequently, by their net electronegative electric charge a lone.

2. Some Proteins Treated by Reagents Modifying Lysine Residues Inhibit infection by HIV-1 and CD4- gp120 Binding BSA treat ed by most of the reagents listed in Table 1, except by acid anhydrides 4, 9, 11, 12, 17, 18 and 22, by 4-carboxybenzaldehyde (25) and by phenylglyoxal (24), the latter specific for arginine (Lundblad, (1991), supra), inhibited infection by HIV-1 (Table 2, columns 2–4). Proteins other than BSA treated with selected reagents also had HIV-1 inhibitory activity (Table 2). BSA and HSA treated with the same reagents had similar antiviral activities (compare lines 2, 5, 35 with lines 24, 13, 61 in Table 2).

Other modified macromolecules (transferrin, IgG and more noticeably synthetic dendrimers, RSA and casein) had lower anti-HIV-1 activity in comparison with BSA (compare the following group of lines in Table 2: 2, 3, 45, 47, 53; 12, 15, 17, 18; 10, 32; 11, 33; 35, 54; 11, 57; and 6, 58). Modified gelatin (lines 16 and 25) was devoid of antiviral activity. Phenylglyoxal treated casein (line 20), unlike BSA modified with this reagent, inhibited infection by HIV-1. Pretreatment of BSA with trypsin reduced the anti-HIV-1 activity elicited by treatment with reagent #7 (compare lines 2 and 46 in Table 2), while reduction and alkylation prior to lysine modification had a much lesser effect (compare lines 5 and 12 in Table 2).

Figure 2:
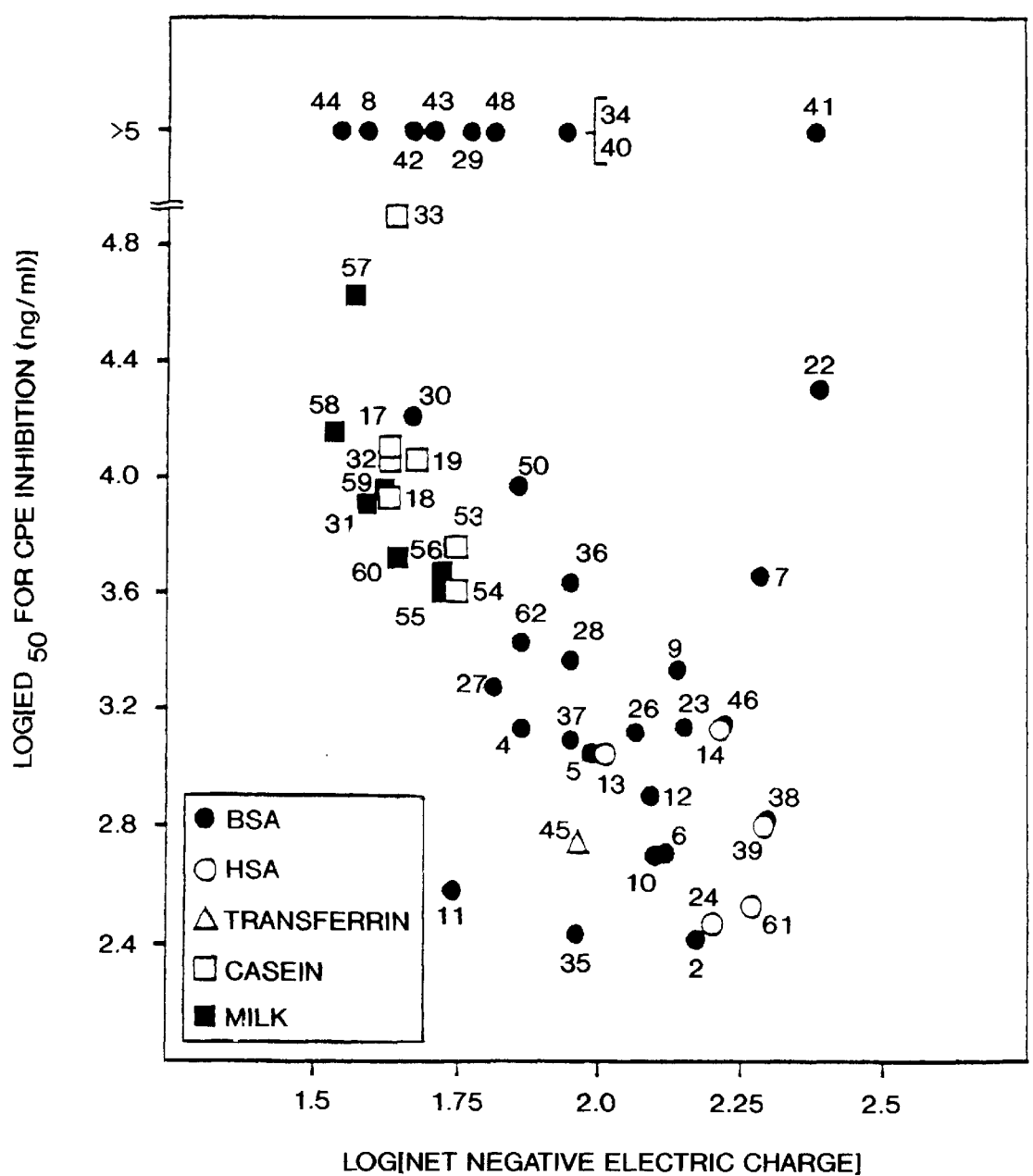
FIG. 2 is a graph showing the lack of relationship between the antiviral activities (expressed as $ED_{50}$ for inhibition of CPE) and the net negative electric charges of modified proteins listed in Table 1 herein. The corresponding numbers are indicated near each experimental point.
Figure 3:
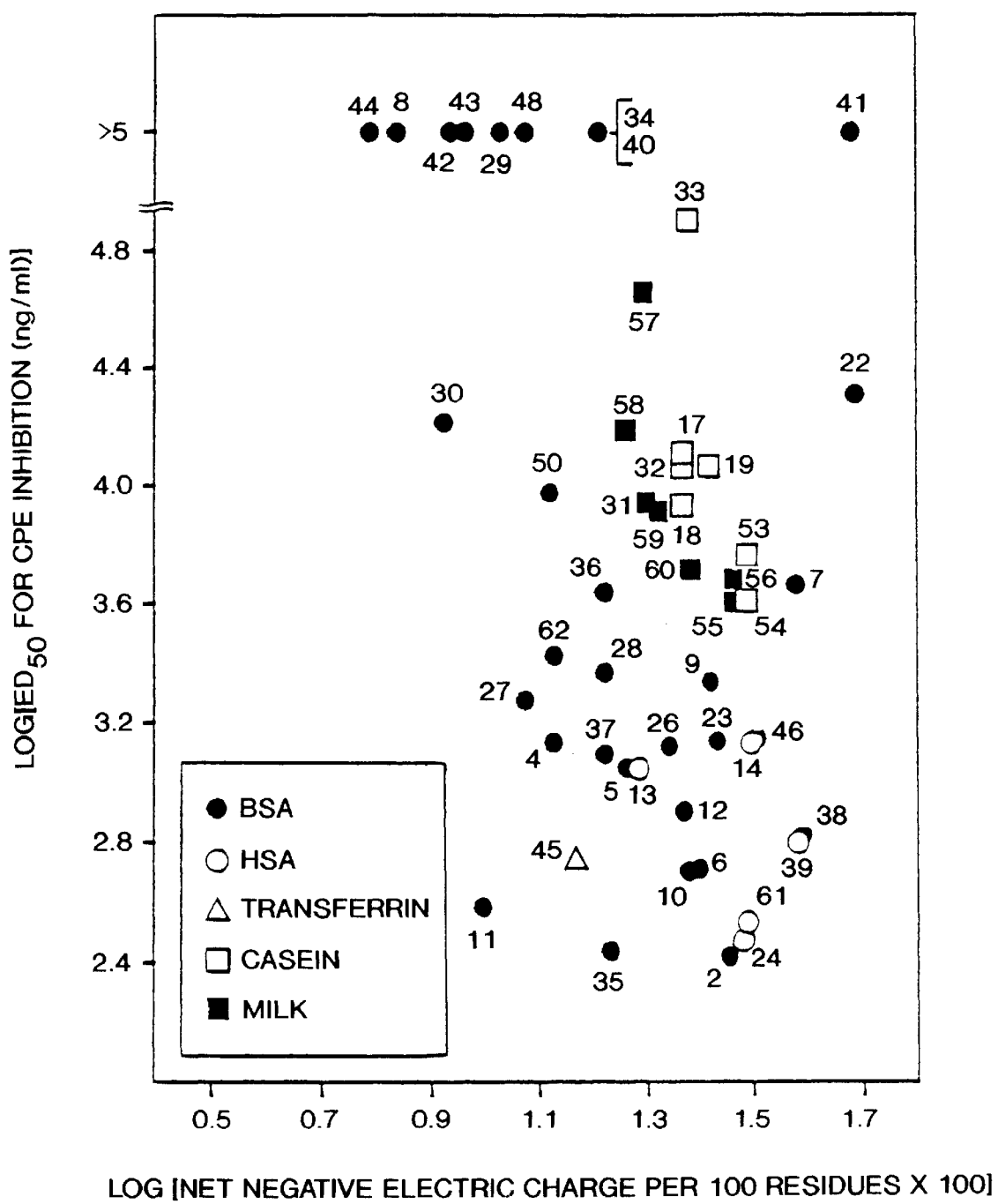
FIG. 3 is a graph showing the lack of relationship between the antiviral activities (expressed as $ED_{50}$ for inhibition of CPE) and the net negative electric charges, related to molecular masses of the compounds of the modified proteins listed in Table 1 herein.

The anti-HIV-1 activity of the modified proteins was not correlated to their net negative electric charge (FIGS. 2 and 3; the correlation coefficients for a linear relationship between values on the ordinates and abscissas were ~0.4). Most effective in the conversion of both BSA and casein (or total milk protein) into antiviral compounds were the structurally closely related aromatic acid anhydrides 5, 6, 7 and 8 (Table 1). In conclusion, there are striking differences among proteins and protein modifying reagents with respect to their effectiveness as starting materials for preparation of macromolecular anti-HIV-1 compounds.

The inhibitory effect of the chemically modified macromolecules on infection of cells by HIV-1 was measured by two assays based on suppression of the virus-induced cytopathic effect (CPE) and on the production of the HIV-1 nucleocapsid antigen P24, respectively. Similar results were obtained by the two tests [the value of the correlation coefficient for the linear regression between ED$_{50}$ values (Table 2) for the respective assays was 0.97].

The compounds also inhibited fusion between HIV-1 infected and uninfected cells (Table 2, column 4) and the corresponding ED$_{50}$ values were on average higher, by more than one order of magnitude, than ED$_{50}$ values for inhibition of CPE. This suggested that inhibition of fusion does not play a major role in the virus-inhibitory activity of the compounds tested. This is in agreement with results described above, indicating that this activity cannot be related to blocking of the gp120 V3 loop, known to be involved in the fusion process (Marcon, L. and Sodroski. J. (1994), "gp120-Independent Fusion Mediated by the Human Immunodeficiency Virus Type 1 gp41 Envelope Glycoprotein: A Reassessment", *J. Virol.*, 68, 1977–1982).

The modified proteins also failed to bind to the N-terminal region of gp41which is also involved in the fusion process (Freed, E. O., Myers, D. J., and Risser, R., (1990), "Characterization of the Fusion Domain of the Human Immunodeficiency Virus Type 1 Envelope Glycoprotein gp41", *Proc Natl Acad Sci USA*, 87, 4650–4654).

Figure 4:
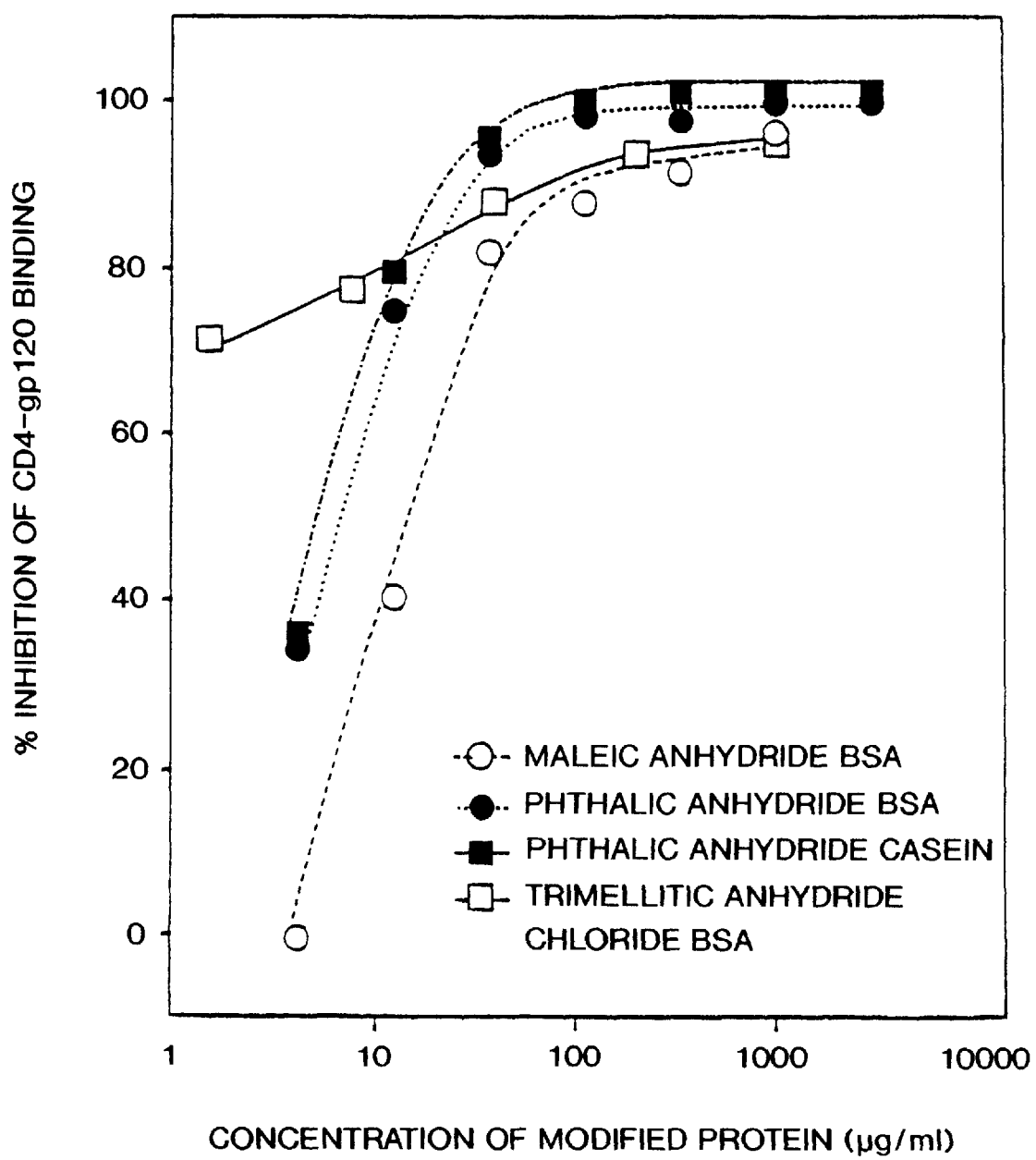
FIG. 4 is a graph showing the inhibitory effect of distinct acid anhydride treated proteins on gp120-CD4 binding as determined by the NENQUEST Drug Discovery System: HIV gp120/CD4 Receptor (DuPont NEN, Boston, MA). The quantity of gp120 used per test was 5 ng/ml. The absorbance ($OD_{450}$) corresponding to bound gp120 in the absence of inhibitors was 0.695.
Figure 5:
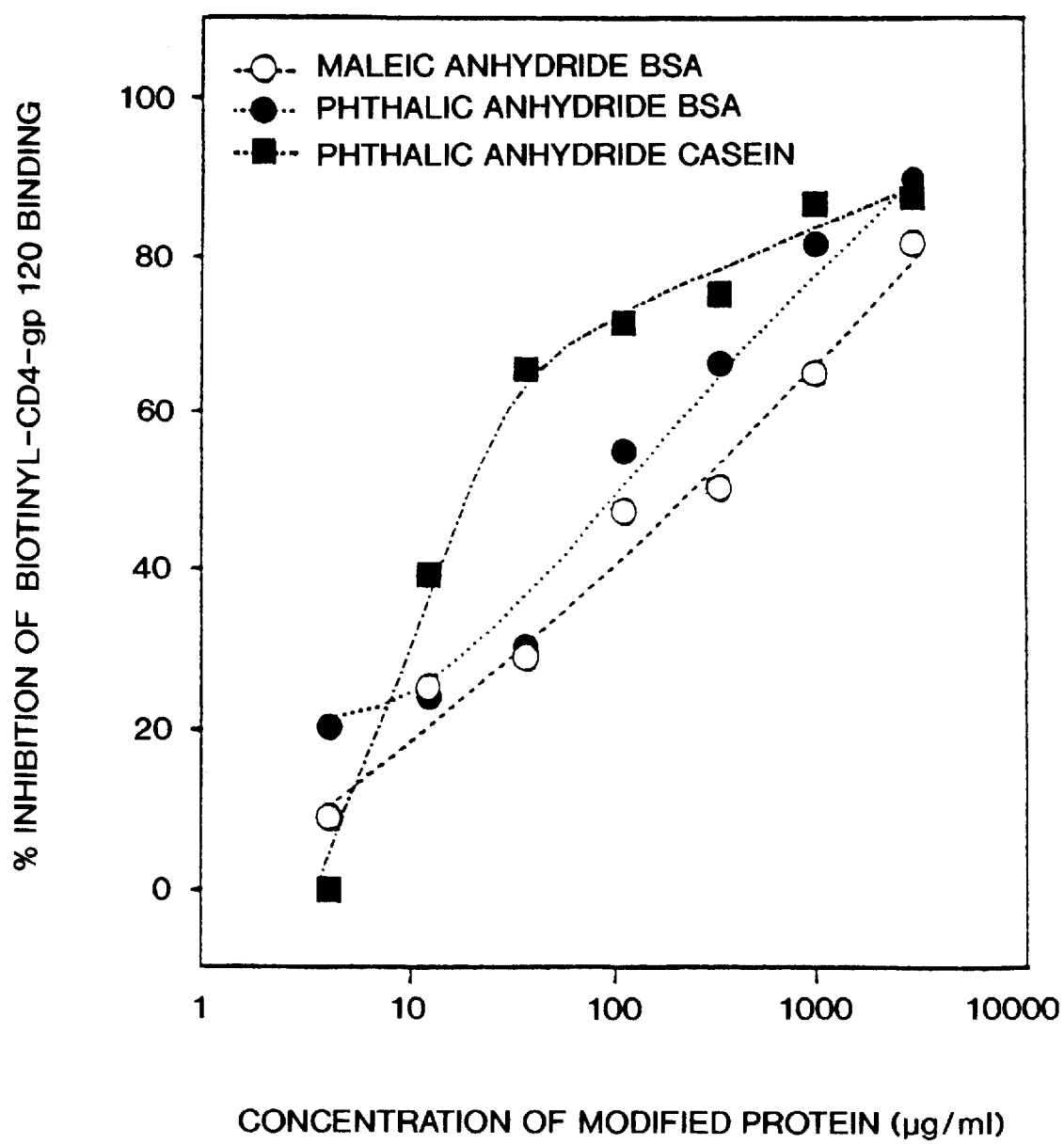
FIG. 5 is a graph showing the inhibitory effect of distinct acid anhydride treated proteins on binding of biotinylated CD4 (500 ng/ml) to gp120 coated wells. Bound biotinyl-CD4 was determined by quantitating horseradish peroxidase-labeled streptavidin subsequently bound to the wells. The absorbance ($OD_{450}$) corresponding to bound biotinyl-CD4 in the absence of inhibitors was 0.940.

To gain insight into the mechanism of anti-HIV-1 activity of the chemically modified macromolecular compounds, their effect on binding between gp120 and the soluble CD4 cell receptor for the virus was investigated. The compounds inhibited gp120-CD4 association with varied efficacies. Representative dose response curves are shown in FIGS. 4 and 5 and all data in the form of $ED_{50}$ values (obtained by assays described for FIG. 4) are compiled in column 5 of Table 2. It is notable that these $ED_{50}$ values were lower by at least two orders of magnitude than those corresponding to inhibition of mAb 9284 binding to gp120 (compare FIG. 1 with FIGS. 4 and 5).

The protein modifying reagents differed greatly with respect to effectiveness in converting the same protein into an inhibitor of gp120-CD4 binding. For example, for BSA reagents 5, 6, 8, 16, 21 and 30 (Table 1) were the most effective in this respect (=compounds 5, 10, 35, 37, 36 and 30 in Table 2). Chemicals 6, 7 and 8 appeared to be the reagents of choice to modify milk proteins (=compounds 31, 55 and 56 in Table 2). Introduction of aromatic residues by modifying arginines in proteins already pretreated with an aliphatic acid anhydride lead to further increases of both anti-HIV-1 and gp120-CD4 binding inhibitory activities (compare compounds 57 and 59 in Table 2). This effect was less noticeable with proteins pretreated with aromatic acid anhydrides (compare compounds 5 and 9; and 31 and 60).

Figure 6:
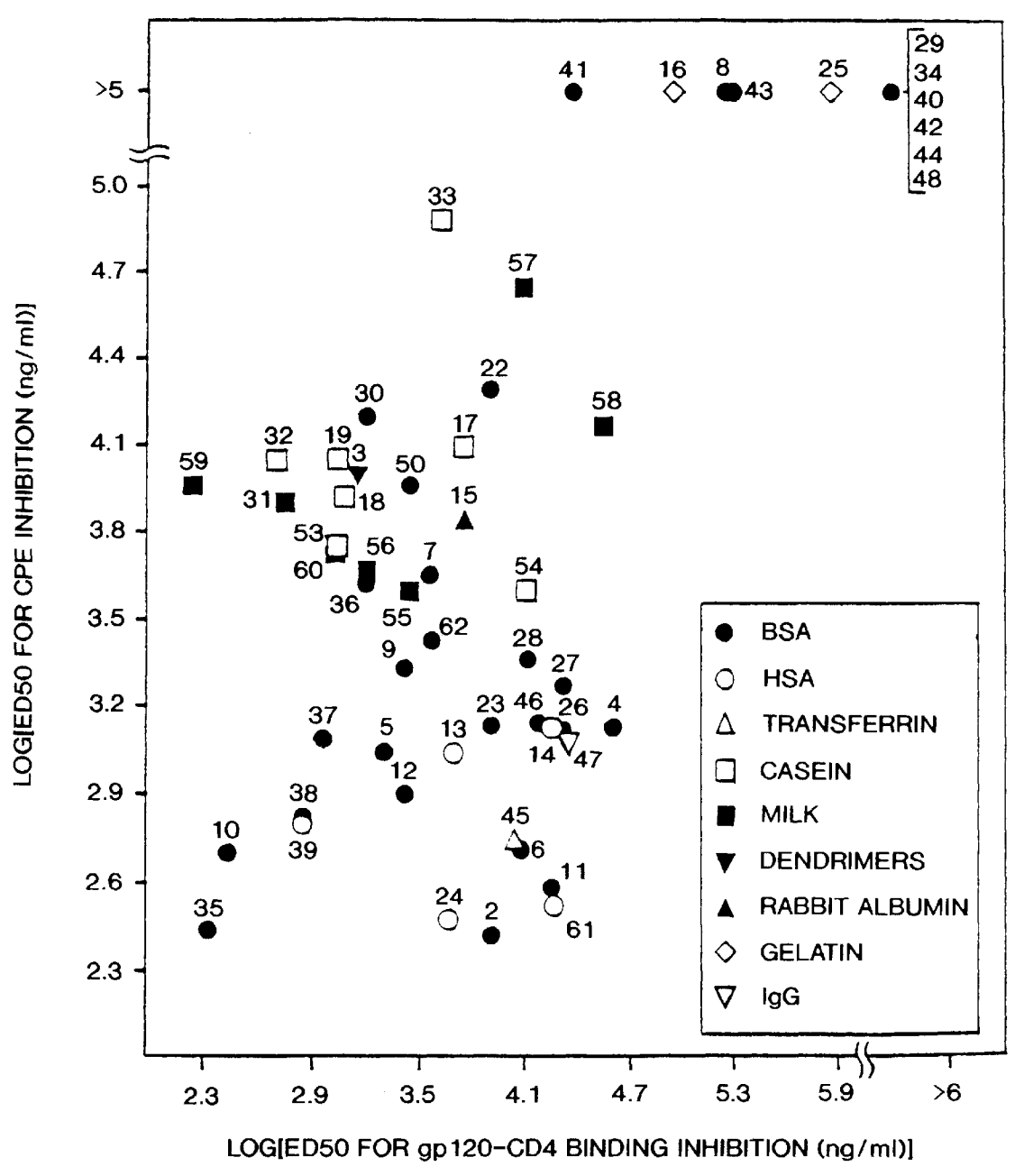

In general, the correlation between anti-HIV-1 and gp120-CD4 binding inhibitory activities of the distinct modified compounds was not good (FIG. 6; the correlation coefficient for a linear regression was 0.69), suggesting that not all compounds inhibit HIV-1 infection by the same mechanisms. However, for those compounds for which the values on the abscissa of FIG. 6 are smaller than those on the ordinate, inhibition of HIV-1 attachment to the CD4 receptor appears to be the major, if not the only, factor contributing to antiviral activity. Noticeably, modified milk proteins, rather than serum albumin, IgG and transferrin, belong to this category of inhibition (FIG. 6).

3-Hydroxyphthalic anhydride treated β-lactoglobulin was a noticeably effective inhibitor of gp120-CD4 binding ($ED_{50}$=~0.01 to 0.1 μg/ml), preventing infection of cells by both the HIV-1 laboratory strain IIIB and by HIV-1 clinical isolates (see Table 3 hereinafter).

3. Aromatic Acid Anhydride Modified Proteins Inhibiting gp120-CD4 Association Bind Preferentially to CD4

Since most chemically modified macromolecules inhibited the interaction between gp120 and CD4 (Table 2, column 5), it was of interest to determine whether or not they blocked the binding site on gp120 for CD4. Therefore, the inhibitory effect of selected modified proteins on the binding of mAb 588D to gp120 was investigated. This mAb binds to a discontinuous epitope overlapping the binding site for CD4 which does not include the V3 loop region (Neurath, A. R., Strick, N., and Jiang, S., (1993), "Synthetic Peptides and Antipeptide Antibodies as Probes to Study Interdomain Interactions in the Envelope of HIV-1", *In: Vaccines*, 93. Modern Approaches to New Vaccines Including Prevention of AIDS, H. S. Ginsberg, F. Brown, R. M. Chanock, and R. A. Lerner (eds.), pp 203–208, Cold Spring Harbor Laboratory Press, New York).

Figure 7:
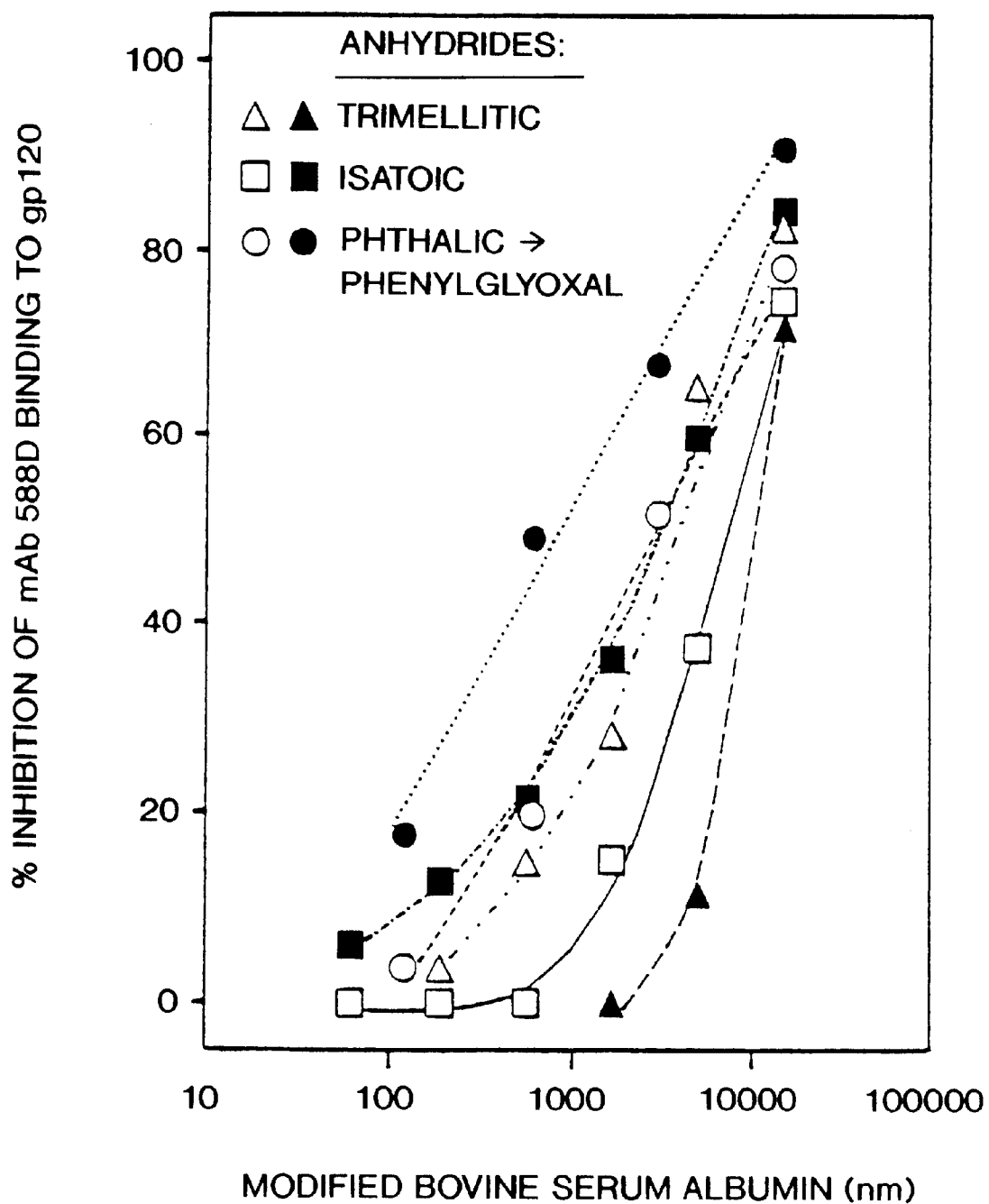
FIG. 7 is a graph showing the inhibitory effect of bovine serum albumin (BSA) treated with distinct acid anhydrides on binding to gp120 IIIB (▲, ■, ●) and MN (△, □, ○) of mAb 588D (1 μg/ml) specific for the CD4 binding site on gp120. The absorbance ($OD_{450}$) corresponding to bound mAb 588D in the absence of inhibitors was 0.520 and 1.669 for gp120 IIIB and MN, respectively.
Figure 8:
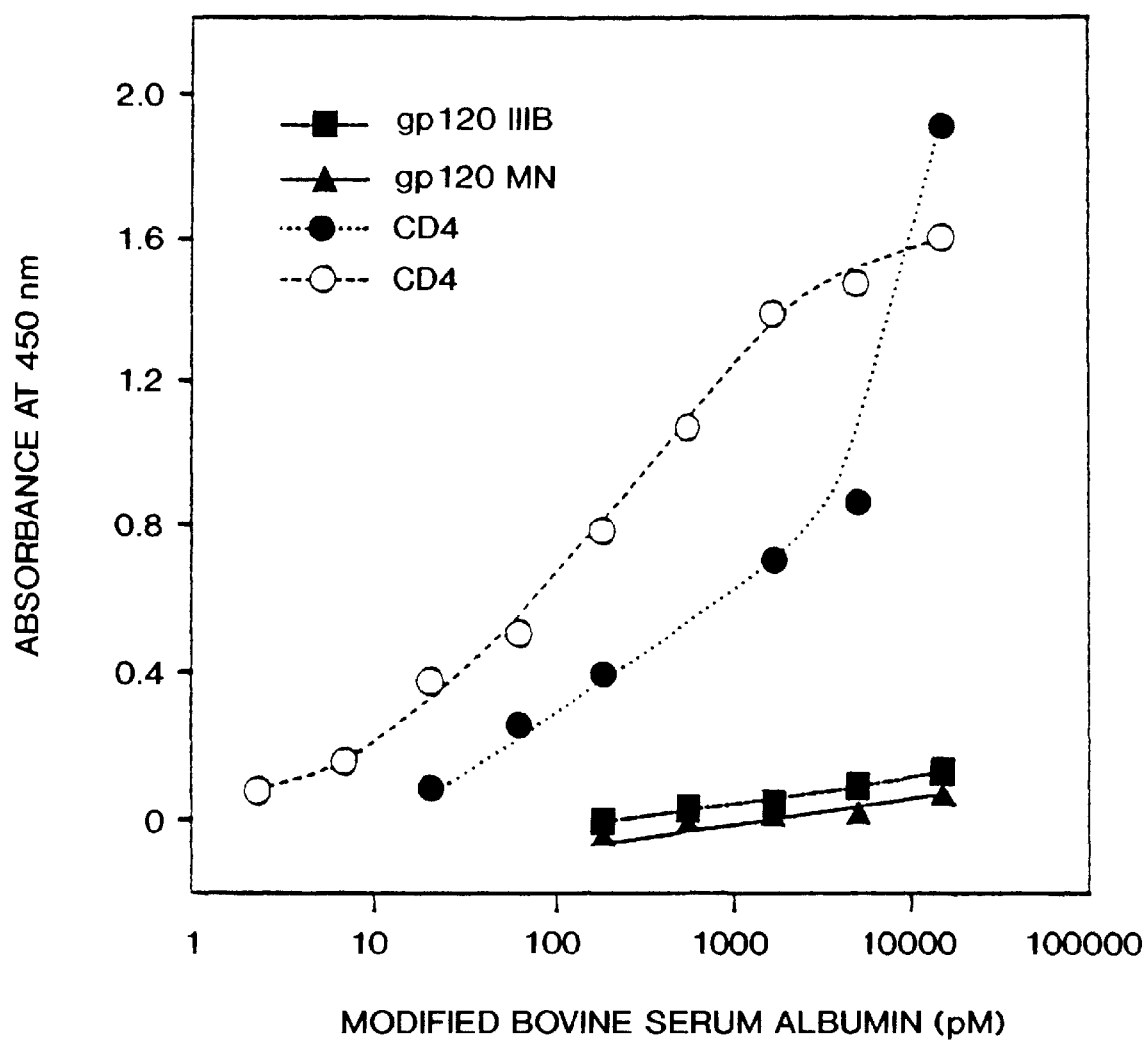
FIG. 8 is a graph showing the binding of trimellitic anhydride (▲, ■, ●) and of trimellitic anhydride chloride (○) treated BSA to gp120 IIIB and MN, respectively, and to CD4. Serial 3-fold dilutions of the chemically modified BSA in Tris-buffered saline (TS) containing 0.25% gelatin were added to wells coated with gp120 IIIB, gp120 MN and CD4, respectively, followed by undiluted goat serum. After incubation for 2 hours at 37° C. and 1 hour at 25° C., the wells were washed with TS and bound modified BSA was quantitated by ELISA using rabbit anti-BSA antiserum (diluted 1:5,000). Binding of modified BSA to control wells coated with goat serum was marginal, and the corresponding ($OD_{450}$) values (range 0–0.029) were subtracted from the $OD_{450}$ values corresponding to gp120 and CD4 coated wells, respectively. Trimellitic anhydride chloride treated BSA bound to gp120 marginally.

The inhibitory effect of selected aromatic acid anhydride treated BSA preparations on the binding of mAb 588D to gp120 IIIB and MN, respectively (FIG. 7), was overall similar to that observed for inhibition of mAb 9284 binding to gp120 IIIB (FIG. 1), and was detectable at concentrations which exceeded those required for blocking gp120-CD4 association (FIGS. 4 and 5; 10 μg/ml BSA=1.49 nM). This apparent discrepancy suggested that CD4 might bind the modified proteins more effectively than gp120. This was indeed observed using two selected BSA-derived preparations (FIG. 8).

Figure 9:
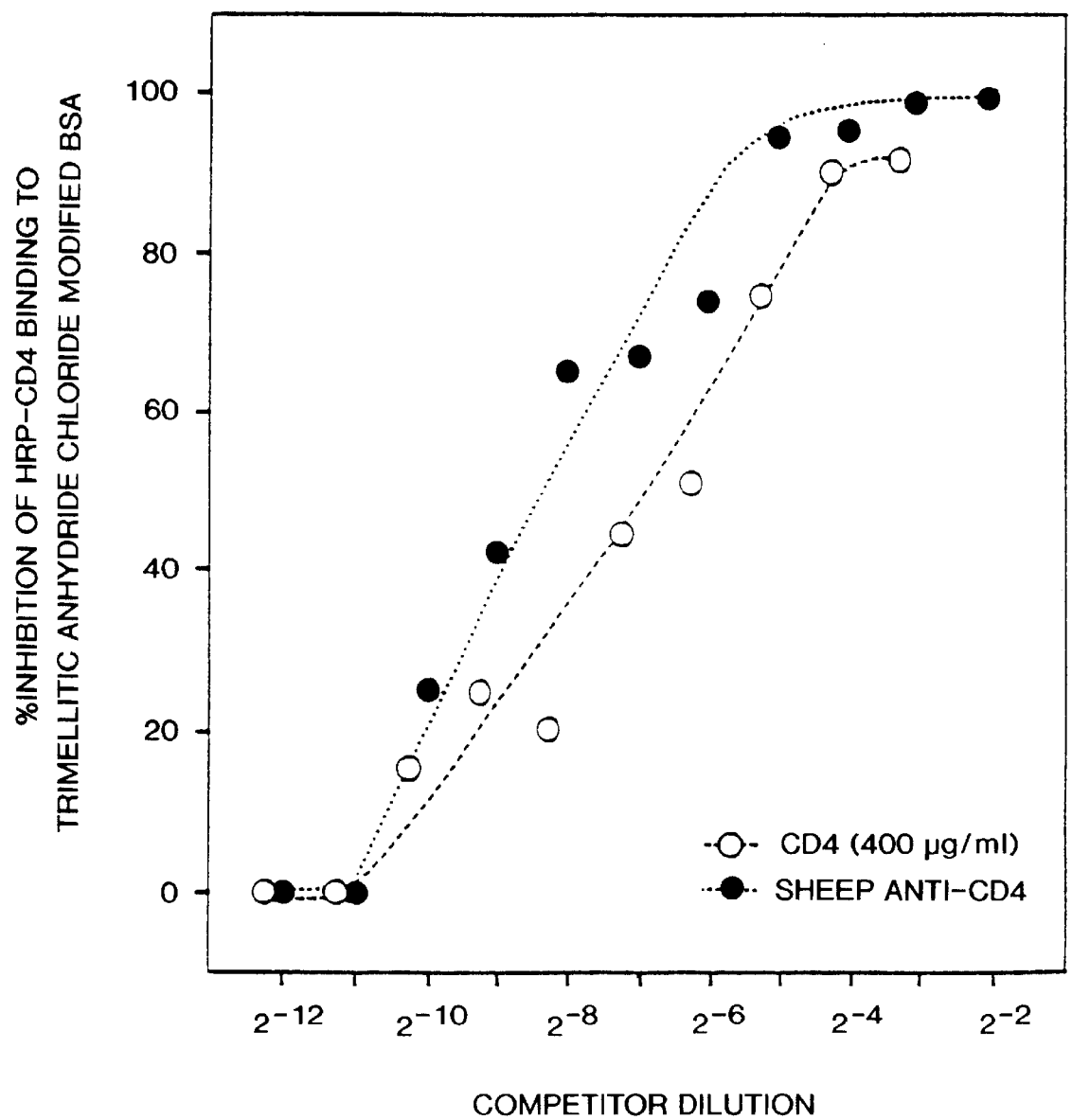
FIG. 9 is a graph showing the inhibitory effect of CD4 and of sheep anti-CD4 antiserum, respectively, on binding of horseradish peroxidase (HRP)-labeled CD4 (500 ng/ml in TS containing 2.5 mg/ml gelatin) to wells coated with trimellitic anhydride chloride modified BSA (200 ng/well). HRP-CD4 in the presence or absence of inhibitors was added to the wells overnight (25° C.). The wells were washed with TS and bound HRP was quantitated. Absorbance corresponding to bound HRP-CD4 in the absence of inhibitors was 1.315. Normal sheep serum at the dilutions used did not inhibit HRP-CD4 binding.
Figure 10:
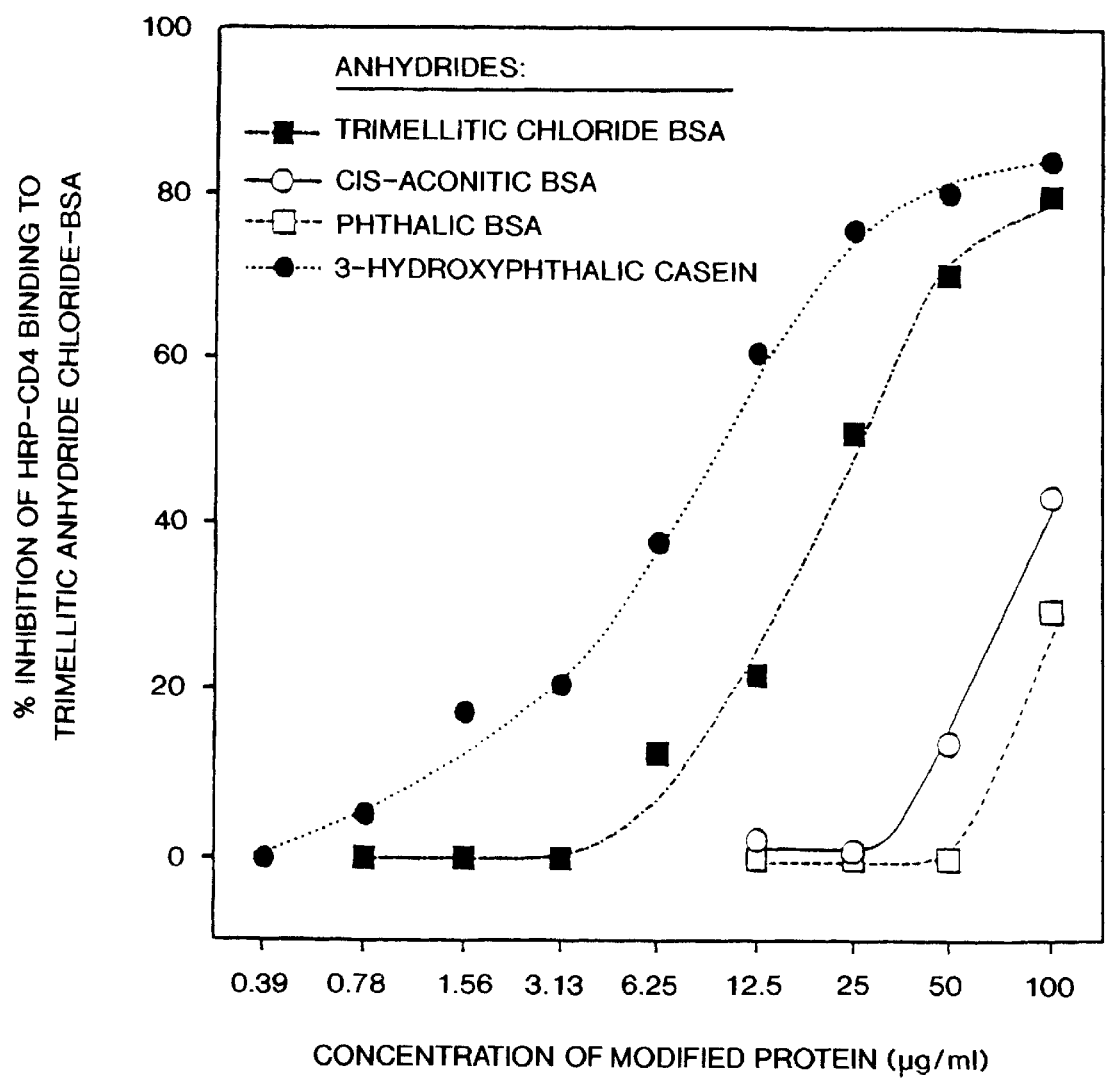
FIG. 10 is a graph showing the inhibitory effect of distinct acid anhydride treated proteins on binding of HRP-labeled CD4 to wells coated with trimellitic anhydride chloride treated BSA (TMA-Cl-BSA). Dilutions of the modified proteins were preincubated for 30 minutes at 25° C. with HRP-labeled CD4 (1 μg/ml CD4 in TS–0.25% gelatin). The mixtures were added to TMA-Cl-BSA wells overnight. The wells were washed with TS, and bound HRP was quantitated. The corresponding absorbance at 450 nm in the absence of inhibitors was 1.265.

The association between modified BSA and CD4 was demonstrated not only in assays using solid phase CD4, but also in tests using wells coated with a selected modified protein and labeled CD4, the binding of which to the wells was blocked by unlabeled CD4 and anti-CD4 antibodies, respectively (FIG. 9), confirming the specificity of binding. The advantage of the latter assay is that there is no need for antibodies against proteins which underwent modifications. Such antibodies may be either unavailable or their reactivity with the modified proteins might be altered as the result of chemical changes. Binding of labeled CD4 to immobilized trimellitic anhydride chloride treated BSA was inhibited not only by the homologous modified protein but also by BSA treated with other reagents and by another selected protein (casein) modified by 3-hydroxyphthalic anhydride (FIG. 10), one of the most effective blockers of gp120-CD4 binding (compound 32, Table 2). Cis-aconitic anhydride treated BSA, a potent anti-HIV-1 compound (11, Table 2), was by comparison a less effective inhibitor of labeled CD4 binding to the solid phase (FIG. 10). These results again indicate that different, although probably partially overlapping, mechanisms a re involved in the antiviral activity of BSA (HSA) treated by aliphatic acid anhydrides and proteins, especially casein (milk proteins), treated with aromatic acid anhydrides.

Figure 11:
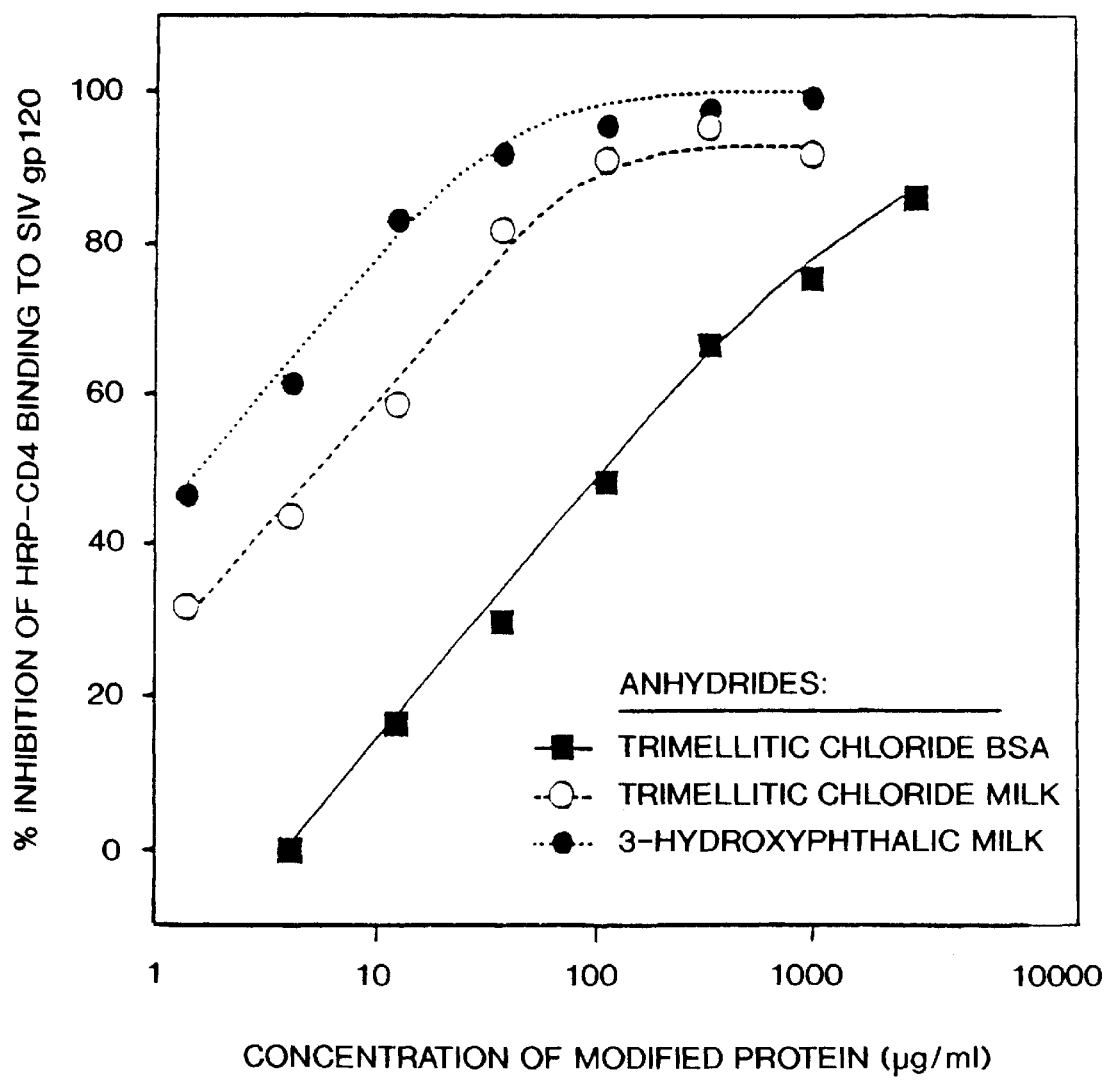
FIG. 11 is a graph showing the inhibitory effect of selected acid anhydride treated proteins on binding of HRP-labeled CD4 to wells coated with SIV gp120. The modified proteins were preincubated with HRP-CD4 (500 ng in TS containing 2.5 mg/ml gelatin) for 30 minutes at 25° C., and the mixtures were added to the wells. After overnight incubation at 25° C., the wells were washed with TS and bound HRP was measured spectrophotometrically. The absorbance at 450 nm in the absence of inhibitors was 0.958.
Figure 12:
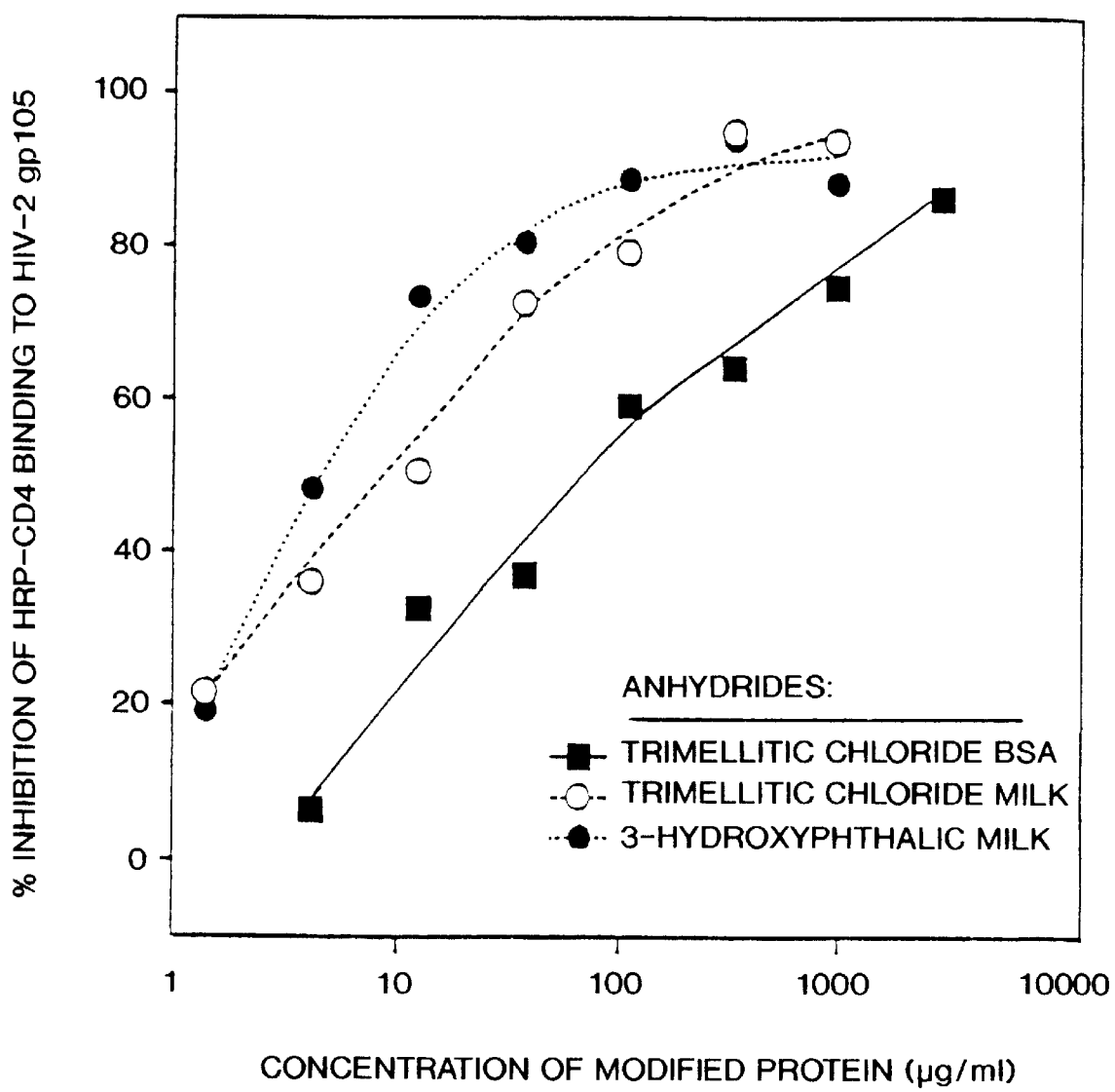
FIG. 12 is a graph showing the inhibitory effect of selected acid anhydride treated proteins on binding of HRP-labeled CD4 to wells coated with HIV-2 gp105. Experimental conditions were the same as described hereinabove for FIG. 11. The absorbance at 450 nm in the absence of inhibitors was 0.769.

4. Inhibition of CD4 Association with Surface Envelope Glycoprobyns of Primate Immunodeficiency Viruses HIV-2 and SIV by Proteins Modified with Aromatic Acid Anhydrides Since a major target for the chemically modified proteins was the CD4 molecule rather than HIV-1 gp120 (FIG. 8), it was anticipated that they would also interfere with the binding to CD4 of primate immunodeficiency viruses other than HIV-1. This expectation is supported by the finding that selected preparations of modified BSA and casein (milk proteins), respectively, inhibited the binding of labeled CD4 to recombinant SIV gpt120 (FIG. 11) and HIV-2 gp105 (FIG. 12). In both cases, casein (milk proteins) were more effective than BSA modified by the same or related reagents.

Figure 13:
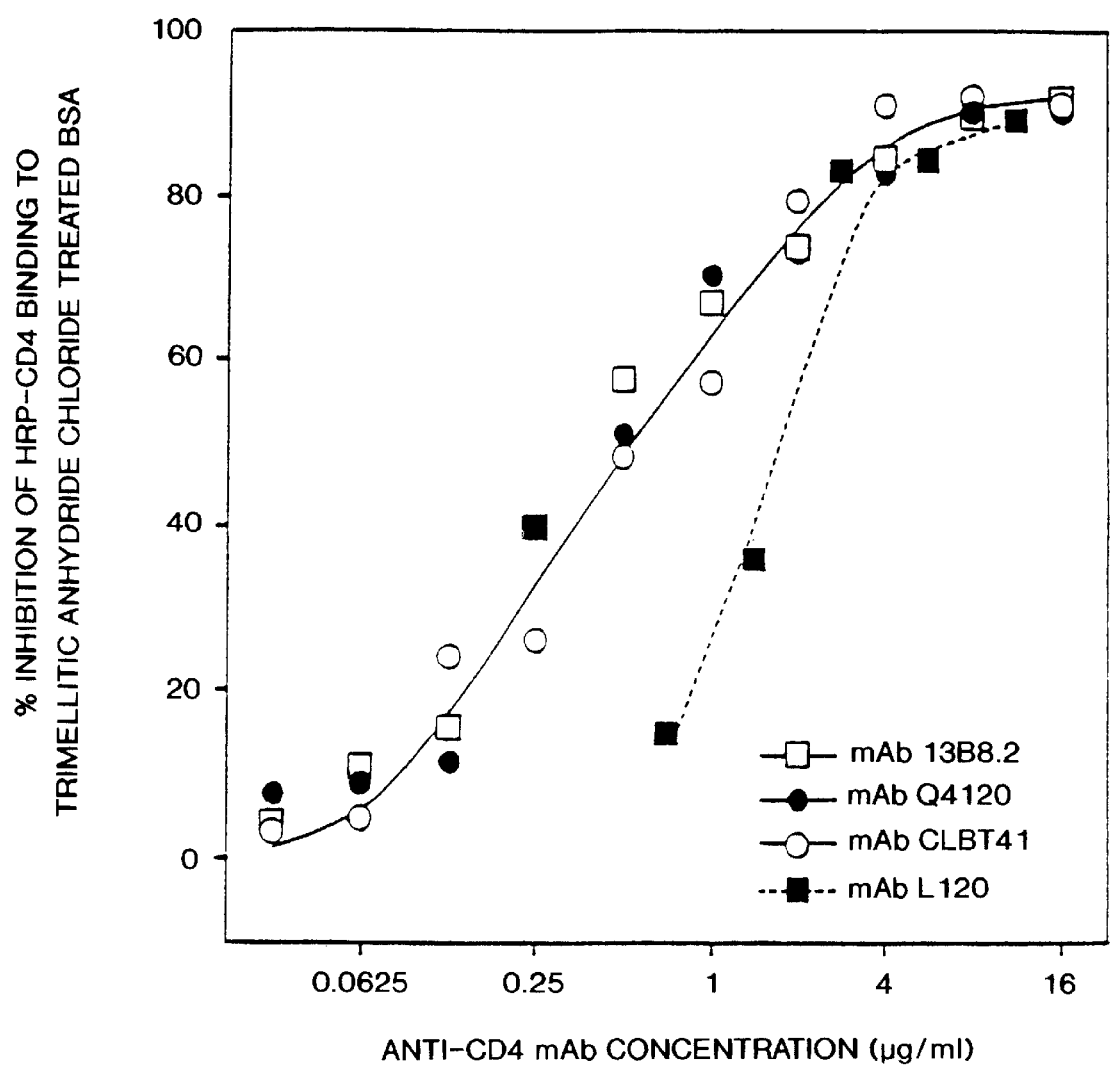
FIG. 13 is a graph showing the inhibitory effect of anti-CD4 mAbs on binding of HRP-labeled CD4 to wells coated with trimellitic anhydride chloride modified BSA. For further explanation, see the above description for FIG. 9. Isotype matched normal mouse IgG did not inhibit HRP-CD4 binding.
Figure 14:
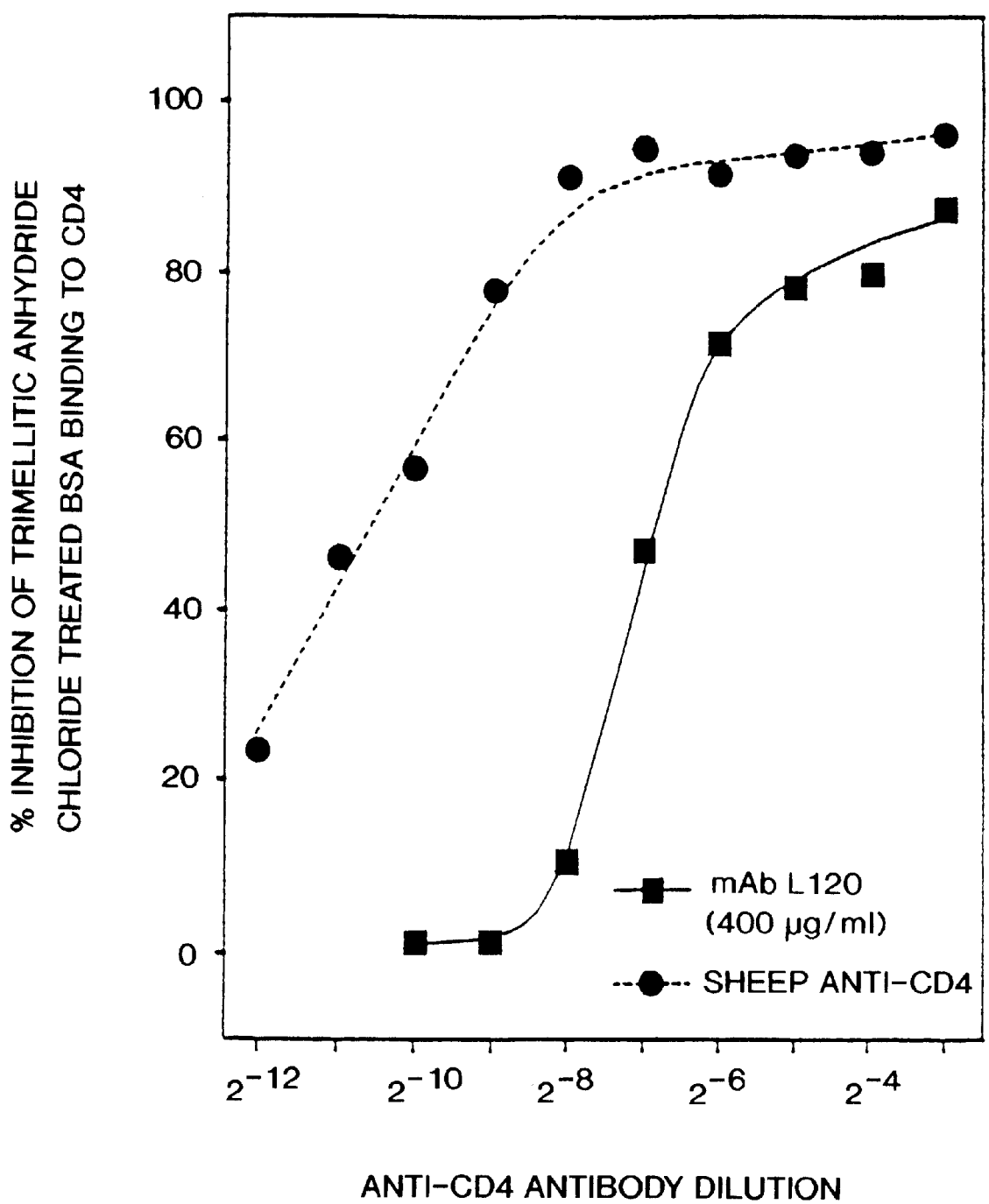
FIG. 14 is a graph showing the inhibitory effect of sheep anti-CD4 antiserum and of mouse anti-CD4 mAb L120, respectively, on binding to CD4-coated wells of BSA treated with trimellitic anhydride chloride (BSA-MAC). Bound BSA-MAC was detected by ELISA using rabbit anti-BSA. Absorbance corresponding to BSA-MAC bound to wells in the absence of anti-CD4 antibodies was 1.149. Normal sheep serum and isotype matched mouse IgG, respectively, at the concentration used did not inhibit BSA-MAC binding.
Figure 15:
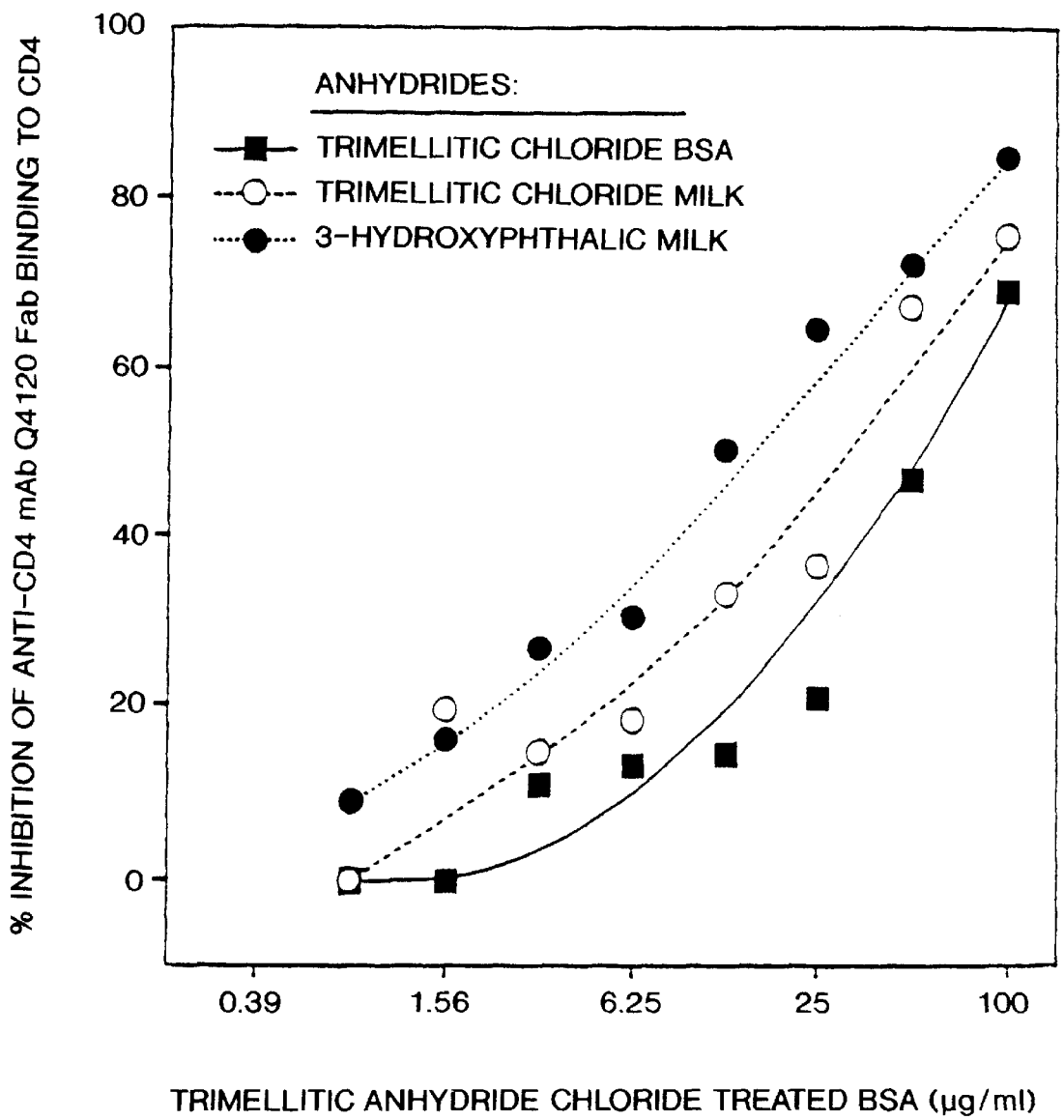
FIG. 15 is a graph showing the inhibitory effect of selected acid anhydride treated proteins on binding to CD4-coated wells of the Fab fragment of anti-CD4 mAb Q4120 (66 ng/well). The absorbance at 450 nm corresponding to bound Fab Q4120 in the absence of inhibitors was 0.612. Control isotype matched Fab from normal mouse IgG did not bind to the wells ($OD_{450}$=0 to 0.003).
Figure 16A:
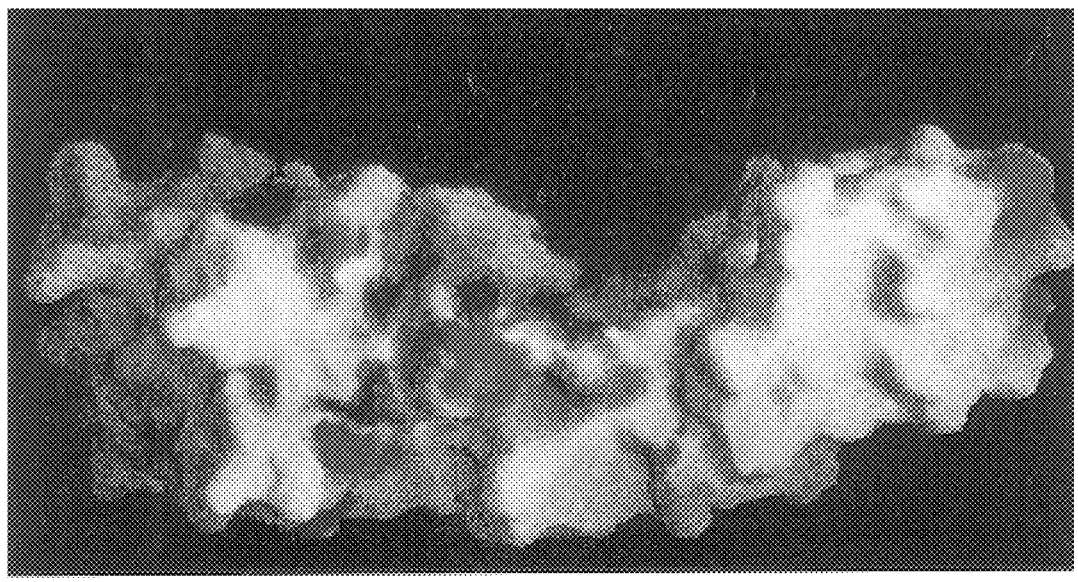
FIGS. 16(a) and (b) are photographs showing the electrostatic potential surface on two orientations, rotated by 180°, of the V1 and V2 domains of the human CD4 molecule. Red and blue areas represent negative and positive potentials, respectively.
Figure 16B:
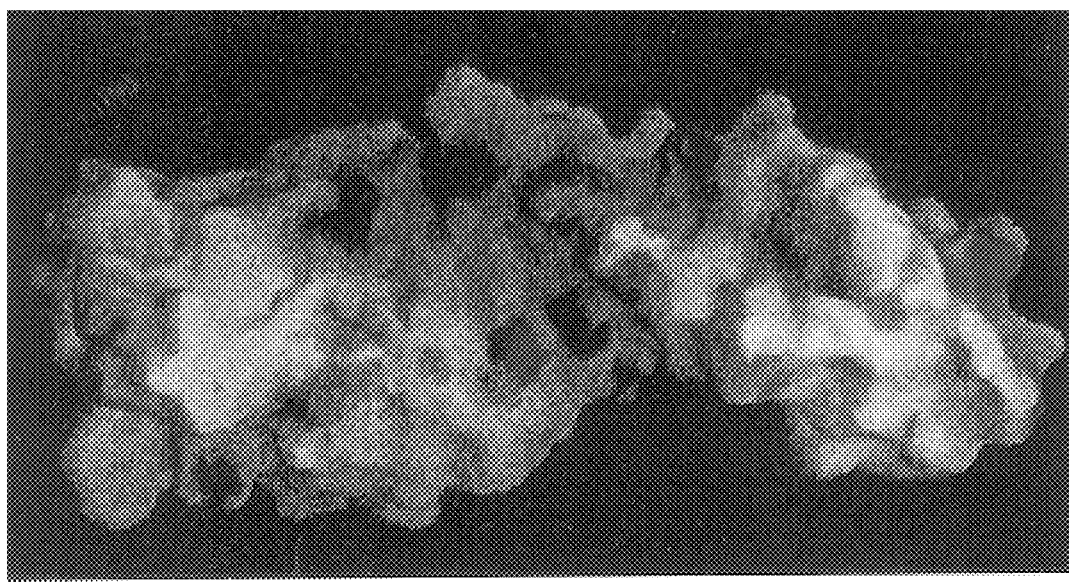
FIGS. 16(c) and (d) are photographs showing the Van der Waal's sphere representation of views corresponding to FIGS. 16(a) and (b). Violet [I34, F43, L44 in the front view constituting FIG. 16(c) and F43 in the back view constituting FIG. 16(d)] and blue [K29, K35, K46, K50, R58, R59 in FIG. 16(c) and R58 and R59 in FIG. 16(d)] spheres represent exposed hydrophobic and positively charged residues, respectively, in the gp120 binding region of CD4. Red [I76, L109, F170, I172, V175, V176 in (c) and V3, V4, V12, L61, L151, V168, F170, V175, L177 in FIG. 16(d)] and green [K7, K8, K72, K75, K142, K171 in FIG. 16(c) and K1, K2, K7, K21, K22, K72, K90, R131, R134, K166, K167, K171 in FIG. 16(d)] spheres represent exposed hydrophobic and positively charged residues, respectively, in CD4 regions other than the gp120 binding domain. CD4 coordinates (pdb code 3cd4) were obtained from the Brookhaven Protein Data Bank (Bernstein, F. C., Koetz, T. F., Williams, G. J. B., Meyer, E. F., Jr., Brice, M. D., Rodgers, J. R., Kennard, O., Shimanouchi, T., Tasumi, M., (1977), "The Protein Data Bank: A-computer-based Archival File for Macromolecular Structure", *J. Mol. Biol.*, 112, 535–542). The electrostatic potential surfaces were derived by the program GRASP (Nicholls, A., Sharp, K., and Honig, B. (1991), "Protein Folding and Association: Insights from the Interfacial and Thermodynamic Properties of Hydrocarbons," *Proteins*, 11, 281–296). The Van der Waal's sphere representations were drawn using QUANTA 4.0 (Molecular Simulations Inc., 16 New England Executive Park, Burlington, Mass. 01803, USA).
Figure 16C:
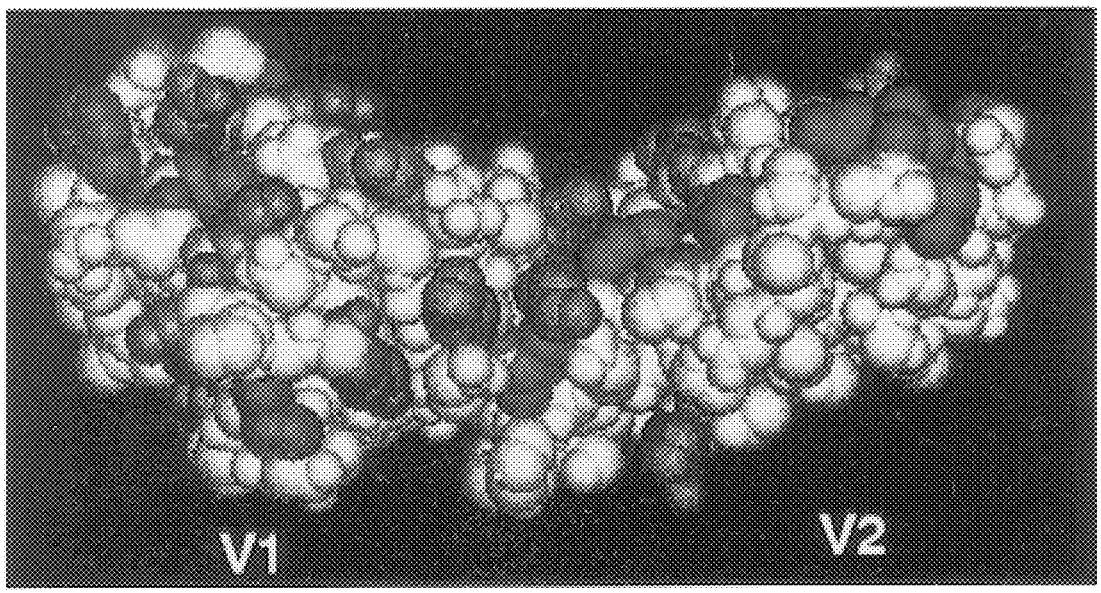
Figure 16D:
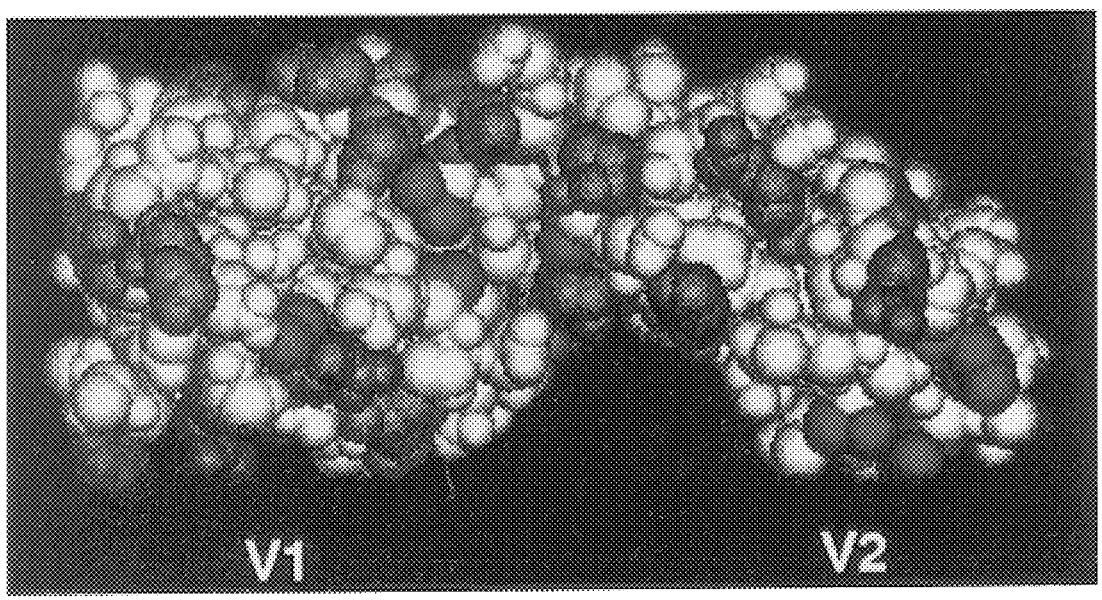

5. Attempts to Define the Binding site on CD4 for Aromatic Acid Anhydride Modified Proteins In order to define the binding site on CD4 for the chemically modified proteins, the inhibitory effect of distinct anti-CD4 mabs on binding of labeled CD4 to wells coated with trimellitic anhydride chloride treated BSA was measured. Representative examples of these assays are shown in FIG. 13. Anti-CD4 antibodies also inhibited the binding of modified BSA to CD4-coated wells (an example is shown in FIG. 14) and the latter assay was used to confirm the inhibitory effect of anti-CD4 mAbs on the association between CD4 and selected proteins modified by aromatic acid anhydrides. In reverse assays, the modified proteins at an ~500-fold molar excess over mAb concentrations failed to inhibit the binding to CD4 of any anti-CD4 mAbs used. However, the modified proteins inhibited the binding to CD4 of monovalent Fab fragments from a selected anti-CD4 mAb (FIG. 15).

Modified β-lactoglobulin inhibited the binding to CD4 of mAbs OKT4a and Q4120 specific for the gp120 binding site of CD4.

Of 17 anti-CD4 mAbs (see above) tested for inhibition of binding between CD4 and modified BSA (as shown for FIG. 13), 11 had detectable inhibitory activity. They were (the relative inhibitory activity compared with $ED_{50}$ for mAb Q4120 is given in parentheses): Q4120 (1), 13B8.2 (0.94), Q4116 (0.94), CLBT41 (0.82), ADP357=12.22.F5.C4 (0.24), ADP310=Q4084 (0.24), ADP356=12.16.42.F9 (0.16), BL4 (0.12), ADP364=D4056 (0.09), ADP359=L120 (0.09) and ADP372=D4003 (0.07). mAbs Q4120, CLBT41 and ADP357 cross-compete with mAb anti Leu3a (Sattentau, Q. J., Arthos, J., Deen, K., Hanna, N., Healey, D., Beverley, P. C. L., Sweet, R., and Truneh, A., (1989), "Structural Analysis of the Human Immunodeficiency Virusbinding Domain of CD4", *J. Exp. Med.*, 170, 1319–1334; Wilks, D., Walker, L., O'Brien, J., Habeshaw, J., and Dalgleish, A., (1990), "Differences in Affinity of Anti-CD4 Monoclonal Antibodies Predict their Effects on Syncytium Induction by Human Immunodeficiency Virus", *Immunol.*, 71, 10–15).

Residues $K_{35}$, $N_{39}$, $Q_{40}$, $T_{45}$, $K_{46}$, and $G_{47}$ in the CD4 sequence appear to be essential for anti-Leu3a mAb binding (Peterson, A. and Seed, B., (1988), "Genetic Analysis of Monoclonal Antibody and HIV Binding Sites on the Human Lymphocyte Antigen CD4", *Cell*, 54, 65–72). The corresponding CD4 segment overlaps with residues shown to be involved in gp120 binding ($K_{29}$, $K_{35}$, $F_{43}$, $L_{44}$, $K_{46}$, $G_{47}$, and $R_{59}$) (Ryu, S.-E., Truneh, A., Sweet, R. W., and Hendrickson, W. A., (1994), "Structures of an HIV and MHC Binding Fragment from Human CD4 as Refined in Two Crystal Lattices", *Structure*, 2, 59–74).

MAb 13B8.2 appears specific for the CDR-3 loop encompassing residues 85–97 (Camerini, D. and Seed, B., (1990), "A CD4 Domain Important for HIV-Mediated Syncytium Formation Lies Outside the Virus Binding Site", *Cell*, 60, 747–754) and binds to a discontinuous epitope involving residues $Q_{20}$, $E_{87}$, and $D_{88}$ (Houlgatte, R., Scarmato, P., El Marhomy, S., Martin, M., Ostankovitch, M., Lafosse, S., Vervisch, A., Auffray, C., and Platier-Tonneau, D., (1994), "HLA class II Antigens and the HIV Envelope Glycoprotein gp120 Bind to the Same Face of CD4", *J. Immunol.*, 152, 4475–4488).

MAb Q4116 crossblocks mAb Q428 reacting with the CD4 V3 domain (Healey, D., Dianda, L., Moore, J. P., McDougal, J. S., Moore, M. J., Estess, P., Buck, D., Kwong, P. D., Beverley, P. C. L., and Sattentau, Q. J., (1990), "Novel anti-CD4 Monoclonal Antibodies Separate Human Immunodeficiency Virus Infection and Fusion of CD4 Cells From Virus Binding", *J. Exp. Med.*, 172, 1233–1242.

MAb ADP356 is probably specific for the V2 domain and mAbs L120 and D4003 recognize the V4 domain of CD4. MAb D4056 binds to the CDR-1 domain encompassing residues 15–26 of CD4 (Camerini and Seed, (1990), supra).

Thus, the results of the inhibition tests suggest that the aromatic acid anhydride treated proteins with anti-HIV-1 activity bind to several sites on the CD4 molecule, and preferentially (a) to those directly involved in gp120 binding, (b) to the V1 CDR-3 and (c) the V3 domains. Antibodies against the latter two regions affect HIV-1 binding indirectly (Moore, J. P., (1993), "A Monoclonal Antibody to the CDR-3 Region of CD4 Inhibits Soluble CD4 Binding to Virions of Human Immunodeficiency Virus Type 1", *J. Virol.*, 67, 3656–3659) or inhibit steps subsequent to virus binding critical for HIV-1 infectivity (Healy et al, (1990), supra).

Regions on the CD4 molecule most likely to be involved in binding of aromatic acid anhydride modified proteins would be expected to have clustered positively charged and hydrophobic residues. Such clusters (see FIG. 16) occur in: (1) the gp120 binding site, in agreement with experimental results described above; (2) near the N-terminus and C-terminus of the V1 and V2 regions, respectively, which are in proximity within the CD4 structure; (3) N-terminally from the CDR-3 region. The CDR-3 region itself does not contain such clusters, suggesting that the inhibitory effect of mAb 13B 8.2 on CD4-modified BSA interaction is due to steric interference.

Figure 17A:
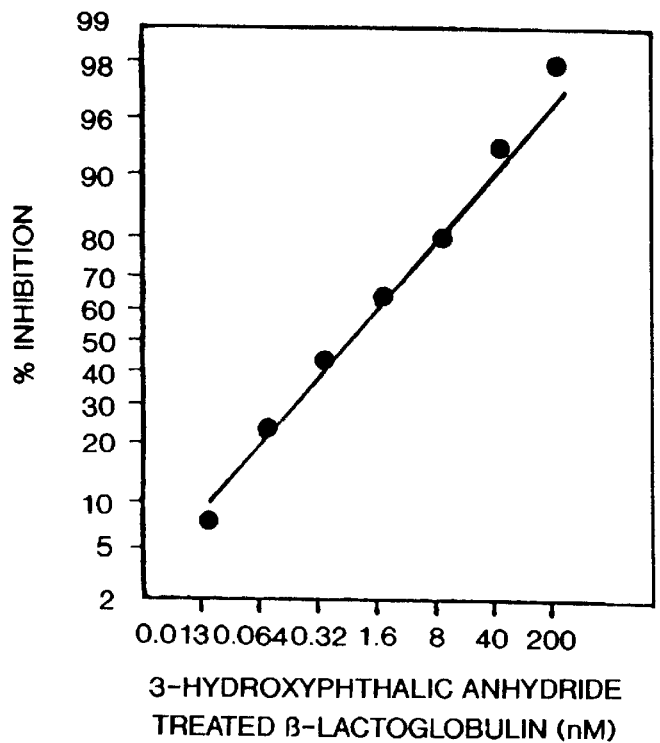
FIGS. 17a to 17d are graphs which show the inhibitory effect of 3-hydroxyphthalic anhydride treated β-lactoglobulin ("3HP-β-LG") on the association between recombinant CD4 and distinct CD4-binding proteins.
Figure 17B:
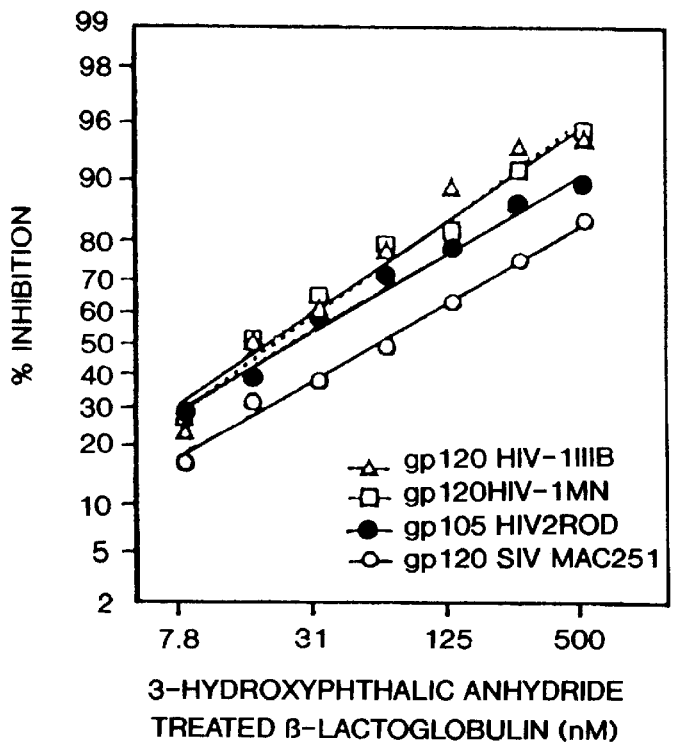
Figure 17C:
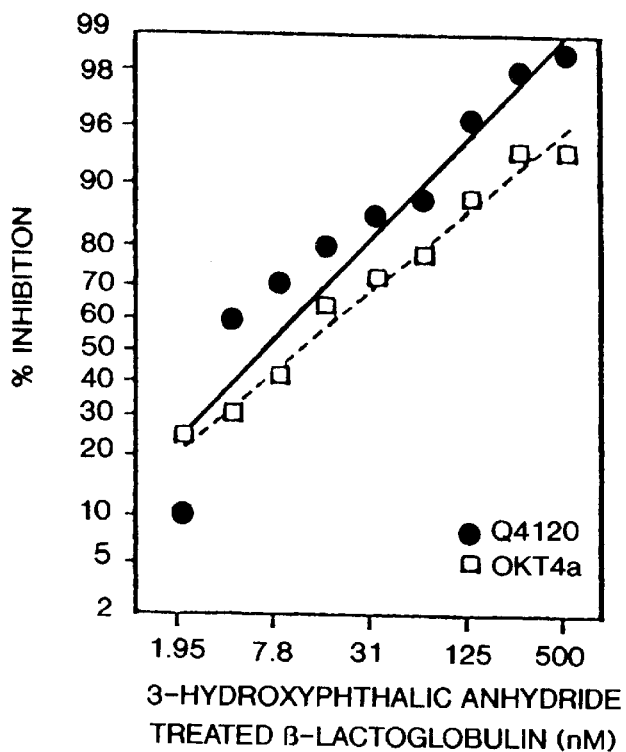

6. Bovine beta-Lactoglobulin Modified BY 3-Hydroxyphthalic Anhydride Blocks the CD4 ° Cell Receptor for HIV 3-Hydroxypthalic anhydride treated bovine β-lactoglobulin (3HP-β-LG) inhibited the binding between soluble CD4 and the SU glycoprotein gp120 from HIV-1 IIIB [FIG. 17a; $IC_{50}$ (=concentration required for 50% inhibition)=0.47 nM]. Similar results were obtained using purified HIV-1 IIIB instead of gp120 (data not shown). Inhibition ($IC_{50}$ values given in parentheses hereinbelow) was also detected in a distinct assay using enzyme-labeled CD4 and immobilized SU glycoproteins from HIV-1 IIIB (23.5 nM) and MN (20.9 nM), from HIV-2 (28.6 nM) and from the simian immunodeficiency virus (SIV) (64.7 nM) (FIG. 17b). Similar results obtained for the distinct SU glycoproteins suggested that the preferential target for 3HP-β-LG was CD4. In accordance with this, 3HP.β.LG inhibited the binding to CD4 of mAbs Q4120 and OKT4a (FIG. 17c; $IC_{50}$=7 and 12.2 nM, respectively), specific for the HIV SU glycoprotein binding site on CD4[3,4] (Healey, D. et al., "Novel anti-CD4 Monoclonal Antibodies Separate Human Immunodeficiency Virus Infection and Fusion of CD4+cells from Virus Binding", *J. Exp. Med.*, 172, 1233–1242 (1990); and Peterson, A. and Seed, B., "Genetic Analysis of Monoclonal Antibody and HIV Binding Sites on the Human Lymphocyte Antigen CD4", *Cell*, 54, 65–72 (1988)).

Figure 17D:
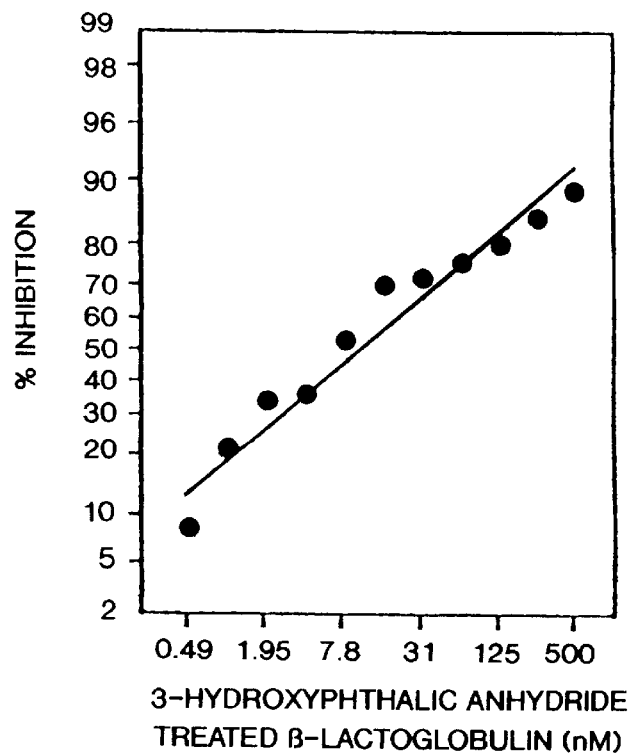

Binding to CD4 of another monoclonal antibody (mAb) anti-Leu3a interfering with CD4-gp120 association and having an epitope distinct from that for mAb OKT4a, (Peterson et al, supra; Landau, N. R., Warton, M. and Littman, D. R., "The Envelope Glycoprotein of the Human Immunodeficiency Virus Binds to The Immunoglobulin-like Domain of CD4", *Nature*, 334, 159–162 (1988); Sattentau, Q. J. et al., "Structural Analysis of the Human Immunodeficiency Virus-Binding Domain of CD4: Epitope Mapping with Site-directed and Anti-Idiotypes", *J. Immunol*, 170, 1319–1334 (1989); Brodsky, M. H., Warton, M., Myers, R. M. and Littman, D. R. "Analysis of the Site in CD4 that Binds to the HIV Envelope Glycoprotein", *J. Immunol.*, 144, 3078–3086 (1990)) was much less inhibited ($IC_{50}$=560 nM; data not shown). Similar results were obtained with CD4 captured onto polystyrene by mAb OKT4 (data not shown). 3HP-β-LG also inhibited the binding of labeled CD4 to trimellitic chloride anhydride treated bovine serum albumin, another modified protein shown to bind CD (FIG. 17d; $IC_{50}$=10 nM, i.e. ≈¼ of the $IC_{50}$ for the homologous protein).

Figure 18:
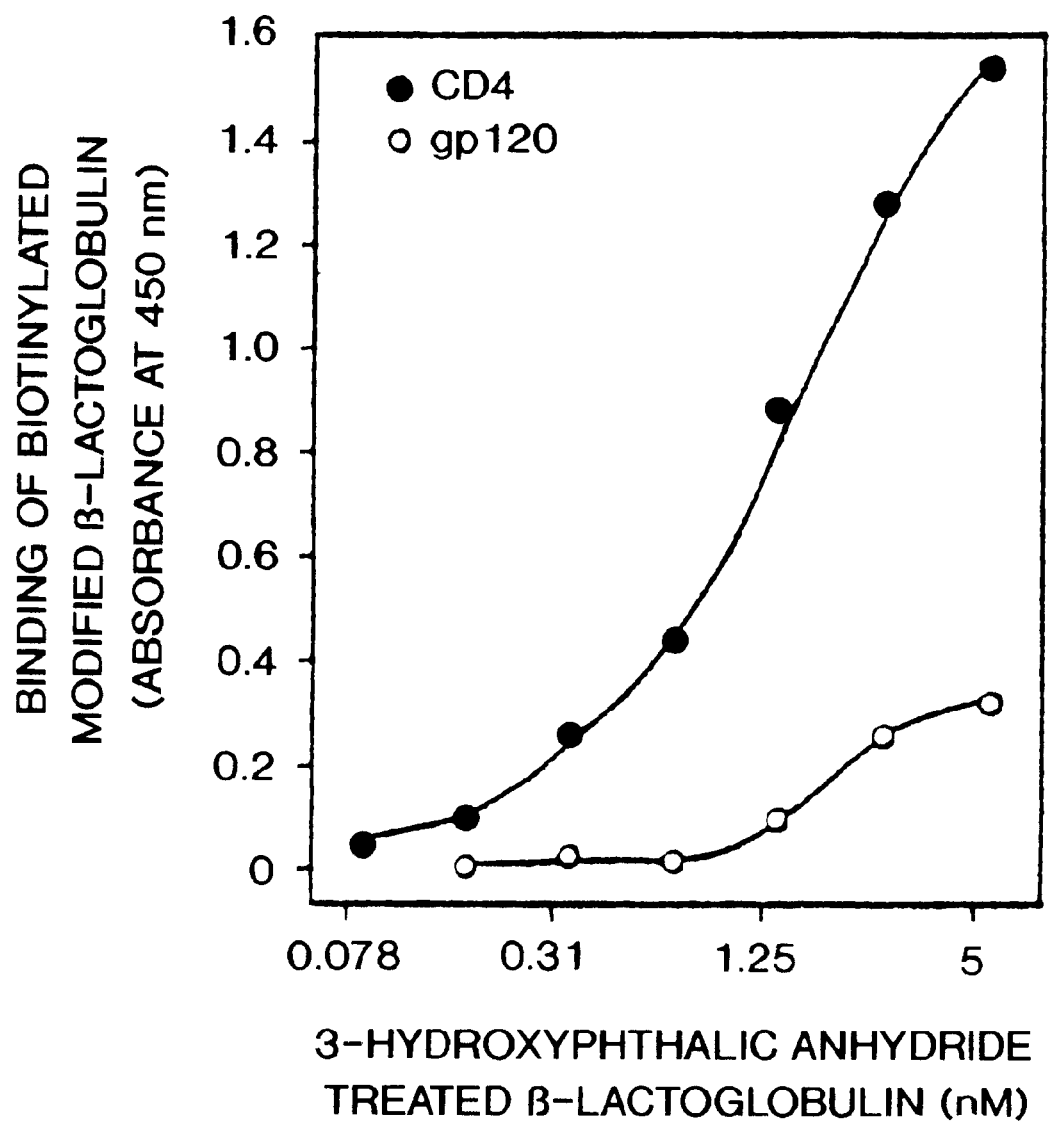
FIG. 18 is a graph showing the preferential binding of 3-hydroxyphthalic anhydride treated β-lactoglobulin (3HP-β-LG) to CD4 as compared to HIV-1 IIIB gp120. Graded quantities of biotinylated 3HP-β-LG were added to gp120 and to CD4 coated wells, respectively. After overnight incubation at 25° C., the wells were washed and bound biotinyl-3HP-β-LG was determined from subsequent binding to the wells of HRP-labeled streptavidin. $OD_{450}$ values corresponding to biotinyl-3HP-β-LG bound to gelatin coated control wells (range 0.107–0.126) were subtracted from values corresponding to gp120- or CD4-bound 3HP-β-LG and the differences were plotted. Unlabeled 3HP-β-LG (556 nM) suppressed the binding of biotinyl-3HP-β-LG (111 nM) to CD4 and to gp120 by 94% and 89%, respectively. Biotinylated untreated β-LG bound neither to gp120 nor to CD4 ($OD_{450} \leq 0.024$). Similar results were obtained using unlabeled 3HP-β-LG, the binding of which to the wells was detected by anti-β-LG antibodies (data not shown).

Binding of 3HP-β-LG to CD4 was also demonstrated directly (FIG. 18). The association constant ($K_a$) for CD4-3HP-β-LG binding, as determined from the inhibitory effect of graded quantities of unlabeled 3HP-β-LG on binding to CD4 of biotinyl-3HP-β-LG (Muller, R. in "Determination of Affinity and Specificity of anti-hapten Antibodies by Competitive Radioimmunoassay", In: *Method in Enzmology. Immunochemical Techniques. Part E. Monoclonal Antibodies and General Immunoassay Methods* (eds. Langone, J. J. & Van Vunakis, H.) 589–601 (Academic Press, 1983)) was $1.54\pm0.14\times10^8$ M$^{-1}$. In comparison, 3HP-β-LG bound to HIV-1 IIIB gp120 to a much lesser extent (FIG. 18). The positively charged V3 loop was the target for 3HP-β-LG on gp120 (data not shown).

Figure 19:
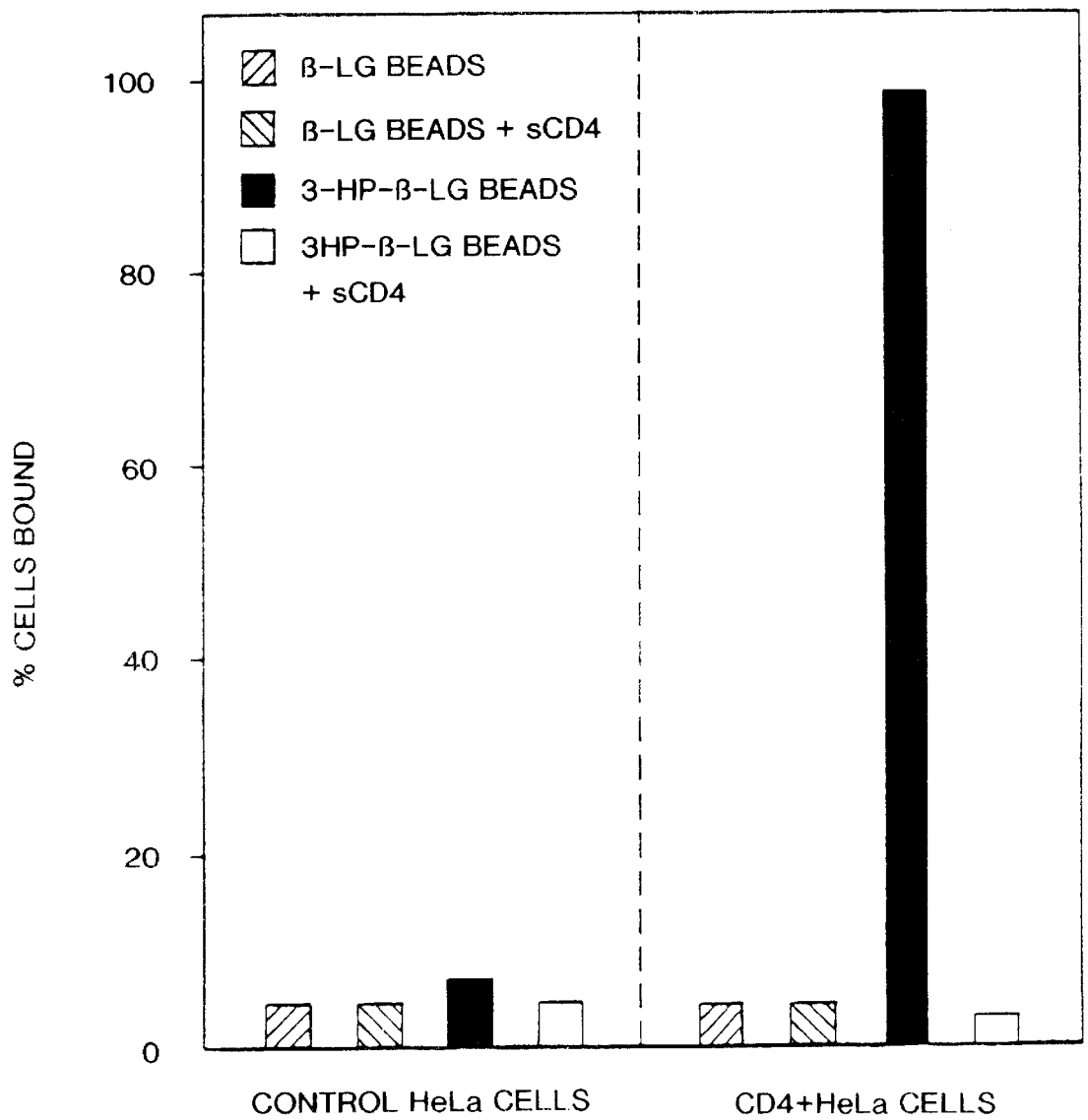
FIG. 19 is a graph showing the binding of CD4-positive and control HeLa cells, respectively, to magnetic beads coated with β-lactoglobulin (β-LG) or with 3-hydroxyphthalic treated β-lactoglobulin (3-HP-β-LG) and binding inhibition by soluble CD4 (25 μg). Bound and unbound cells were quantitated (Neurath, A. R., Strick, N. and Sproul, P., "Search for Hepatitis B Virus Cell Receptors Reveals Binding Sites for Interleukin 6 on the Virus Envelope Protein", *J. Exp. Med.*, 175, 461–469 (1992)).

For 3HP-β-LG to serve as an effective barrier against HIV infection, it ought to bind primarily not only to soluble CD4, but also to cellular CD4. Results shown in FIG. 19 indicate that 3HP-β-LG reacted with CD$^{4+}$ HeLa cells, but not with control HeLa cells. The binding was inhibited by soluble CD4 and was not detected when 3HP-β-LG was replaced by unmodified β-LG.

3HP-β-LG has anti-HIV-1 activity not only against laboratory strains of HIV, but also against clinical isolates of the virus, including AZT-resistant isolates. The ED$_{50}$ for these isolates is in the range of 14–20 μg/ml.

3HP-β-LG prevents not only infection of CD4-positive cells, but also that of epithelial CD4-negative cell lines which may play a role in sexual transmission of HIV-1 and utilize an alternate receptor for HIV-1 instead of CD4 (FIG. 20). This receptor corresponds to galactosylceramide (Cook, D. G., Fantini, J., Spitalnik, S. L. and Gonzalez-Scarano, F., "Binding of Human Immunodeficiency Virus Type 1 (HIV-1) gp120 to Galactosylceramide (GalCer): Relationship to the V3 Loop", *Virology*, 201, 206–214 (1994); Fantini, J., Cook, D. G., Nathanson, N., Spitalnik, S. L. and Gonzalez-Scarano, F., "Infection of Colonic Epithelial Cell Lines by Type 1 Human Immunodeficiency Virus is Associated with Cell Surface Expression of Galactosylceramide, a Potential Alternative gp120 Receptor", *Proc. Natl. Aca. Sci. U.S.A.*, 90, 2700–2704 (1993); Furuta, Y. et al., "Infection of Vaginal and Colonic Epithelial Cells by the Human Immunodeficiency Virus Type 1 is Neutralized by Antibodies Raised Against Conserved Epitopes in the Envelope Glycoprotein gp120"., *Proc. Natl. Acad. Sci U.S.A.*, 91, 12559–12563 (1994); Long, D., Berson, J. F., Cook, D. G. and Doms, R. W., "Characterization of Human Immunodeficiency Virus Type 1 gp120 Binding to Liposomes Containing Galactosylceramide", *J. Virol.*, 68, 5890–5898 (1994); Yahi, N. et al., "Suramin Inhibits Binding of the V3 Region of HIV-1 Envelope Glycoprotein gp120 to Galactosylceramide, the Receptor for HIV-1 gp120 on Human Colon Epithelial Cells", *J. Biol. Chem.* 269, 24349–24353 (1994); Yahi, N., Baghdiguian, S., Moreau, H. and Fantini, J. "Galactosyl Ceramide (or a Closely Related Molecule) is the Receptor for Human Immunodeficiency Virus Type 1 on Human Colon Epithelial HT29 Cells"., *J. Virol.*, 66, 4848–4854 (1992); Yahi, N., Sabatier, J.-M., Baghdiguian, S., Gonzalez-Scarano, F. and Fantini, J., "Synthetic Multimeric Peptides Derived from the Principal Neutralization Domain (V3 loop) of Human Immunodeficiency Virus Type 1 (HIV-1) gp120 Bind to Galactosylceramide and Block HIV-1 Infection in a Human CD4-negative Mucosal Epithelial Cell Line", *J. Virol.*, 69, 320–325 (1995).

The results in Table 2 herein demonstrate that ovomucoid, an egg white-derived product (Products 70 and 71) had a high anti-HIV-1 activity, whereas the corresponding untreated compounds (Products 75 and 76) lacked any activity.

β-Lactoglobulin treated with lysine modifying reagent other than 3-hydroxyphthalic anhydride, namely with pyridoxal phosphate (Product 78), lacked any anti-HIV-1 activity. This indicates that it may not be sufficient only to modify lysine residues and to introduce additional negative charges (in the form of phosphates) to arrive at an anti-HIV-1 compound. Thus, the nature of the lysine modifying reagent is important for endowing the modified protein with anti-HIV-1 activity.

p-Carboxyphenylglyoxal (PCG)-treated BSA (Product 72) had anti-HIV-1 activity. PCG modifies arginines and not lysines. Therefore, modification of arginines instead of or in addition to lysines can result in the production of anti-HIV-1 compounds.

3HP-β-lactoglobulin with added polyethylene glycol chains (Product 66) retained potent anti-HIV-1 activity. PEGylation is frequently used to decrease the immunogenicity and increase the half life of proteins (other drugs) in circulation (N.V. Katre, "The Conjugation of Proteins with Polyethylene Glycol and Other Polymers", *Advanced Drug Deliverly Reviews*, 10, 91–114, (1993). PEGylated modified proteins are candidate anti-HIV-1 agents for intravenous administration. β-LG was also modified with trimellitic and trimellitic chloride anhydrides, respectively, but the resulting products had lower anti-HIV-1 activity than that of 3HP-β-LG and the results are not described herein.

The results in Table 2 indicate that 3HP-β-LG or other aromatic acid anhydride-treated derivatives of β-LG are ideally suited for the prevention of sexual transmission of HIV-1 mediated either by CD4$^+$ or CD4$^-$ cells.

7. Cell-To-Cell HIV Transmission

Results obtained in in vitro systems suggest that cell-to-cell HIV transmission, rather than infection by cell-free HIV represents a more efficient and relevant mode for initiating infection (Sato, H., Orenstein, J., Dimitrov, D. and Martin, M., "Cell-to-Cell Spread of HIV-1 Occurs Within Minutes and May Not Involve the Participation of Virus Particles", *Virology*, 186, 712–724 (1992); Li, P. and Burrell, C. J., "Synthesis of Human Immunodeficiency Virus DNA in a Cell-to-Cell Transmission Model", *AIDS Res. Hum. Retroviruses*, 8, 253–259 (1992); and Pantaleo, G. et al., "Effect of Anti-V3 Antibodies on Cell-free and Cell-to-Cell Human Immunodeficiency Virus Transmission", *Eur. J. Immunol.*, 25, 226–231 (1995)).

Therefore, expression of β-galactosidase (β-gal) in Hela-CD4-LTR-β-gal cells (Kimpton, J. and Emerman, M., "Detection of Replication-competent and Pseudotyped Human Immunodeficiency Virus With a Sensitive Cell Line on the Basis of Activation of an Integrated β-Galactosidase Gene", *J. Virol.*, 66, 2232–2239 (1992) was measured in the absence or presence of graded levels of 3HP-β-LG under conditions in which both cell-free and cell-to-cell virus infection may occur simultaneously. 3HP-β-LG inhibited infection of these cells by both HIV-1 and HIV-2 infected cells [albeit at concentrations higher than those required for inhibition of infection with cell-free virus (Table 3)], as indicated by decreased production of the reporter gene product, β-gal (Table 6). This suggests the following: (1) 3HP-β-LG may prevent infection by biological fluids containing both cell-free and cell-associated HIV and (2) the potency of anti-HIV-1 drugs should be in general evaluated in systems measuring infection by cell-free virus and by infected cells, the latter being more rapid and efficient.

TABLE 1
List of Chemical Formulas of Reagents Used for Protein Modification
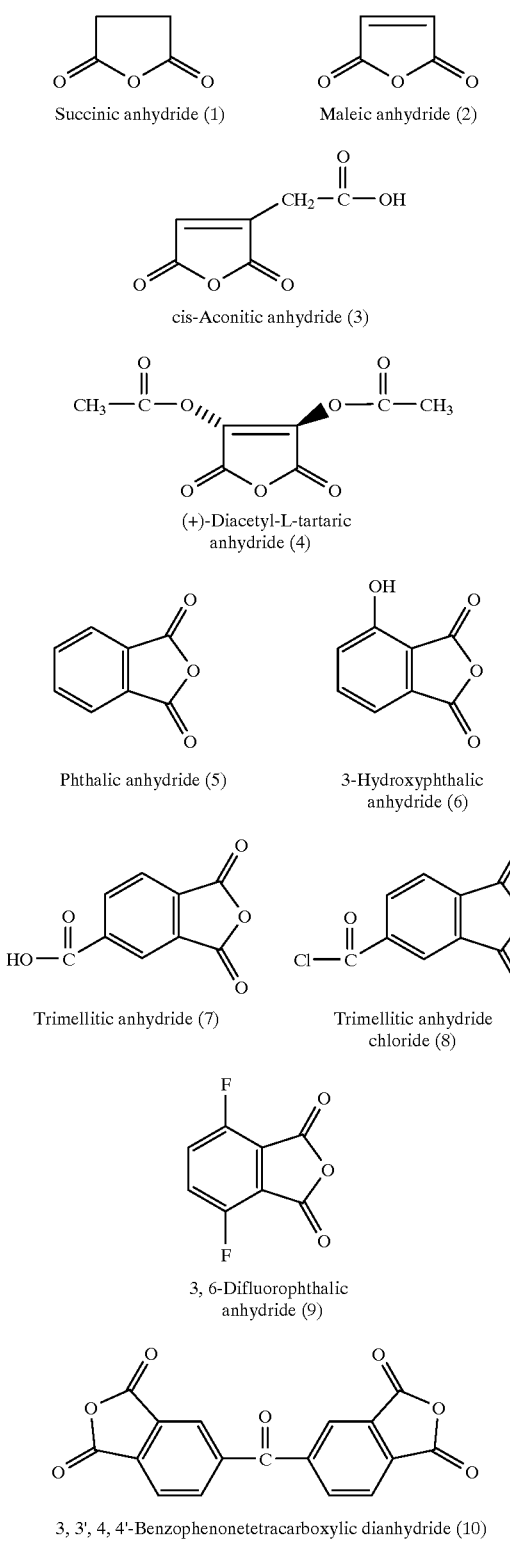
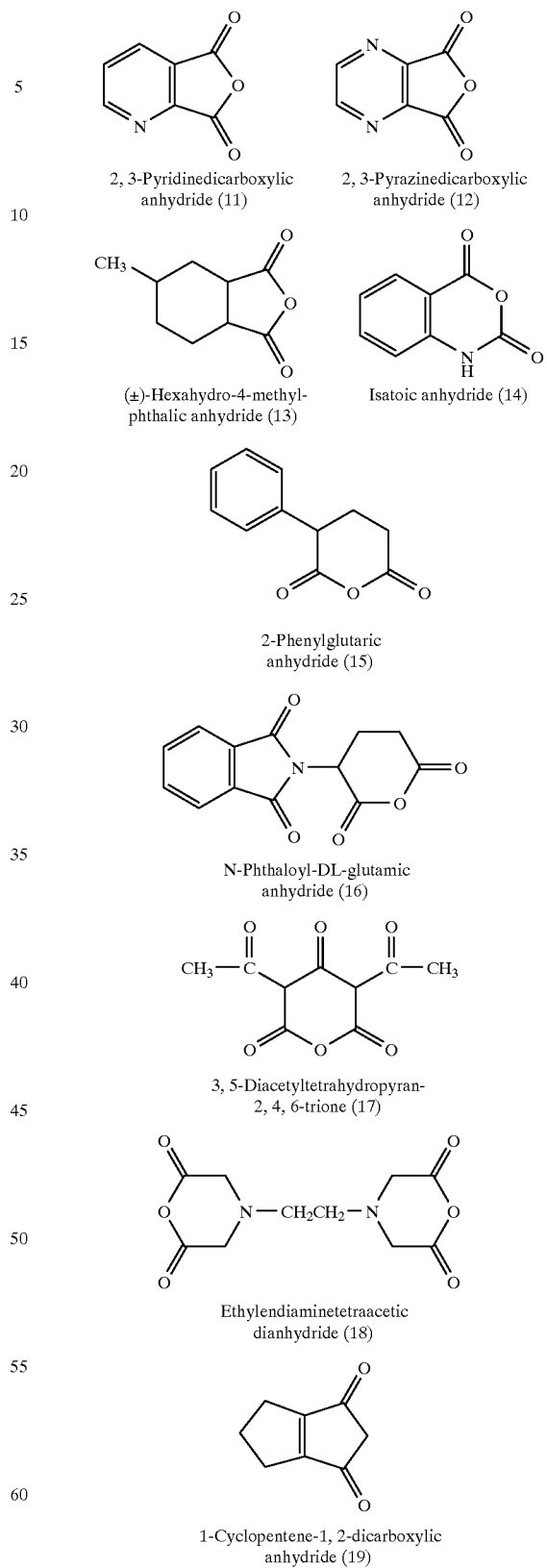

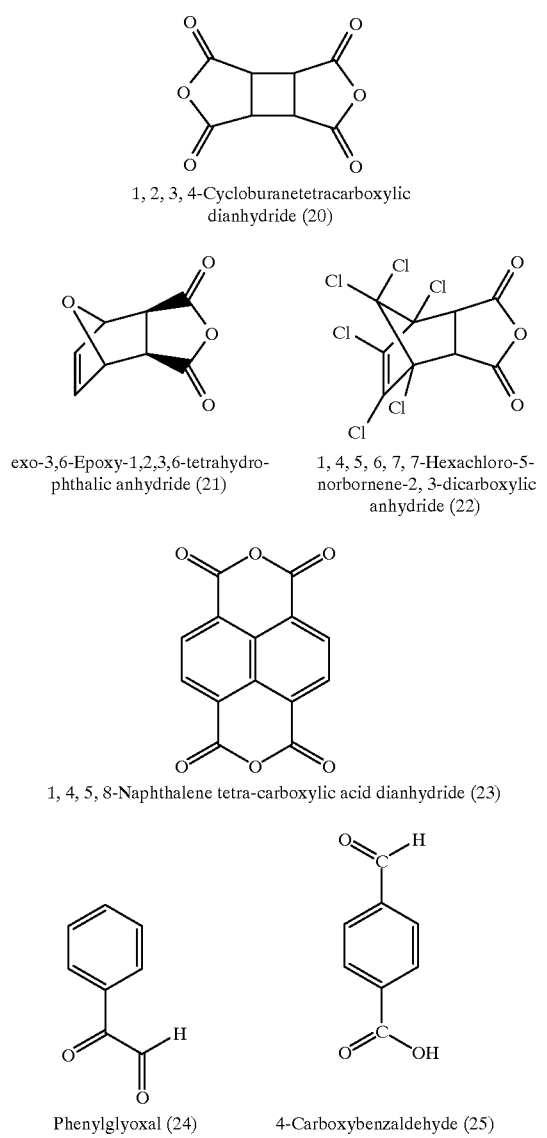
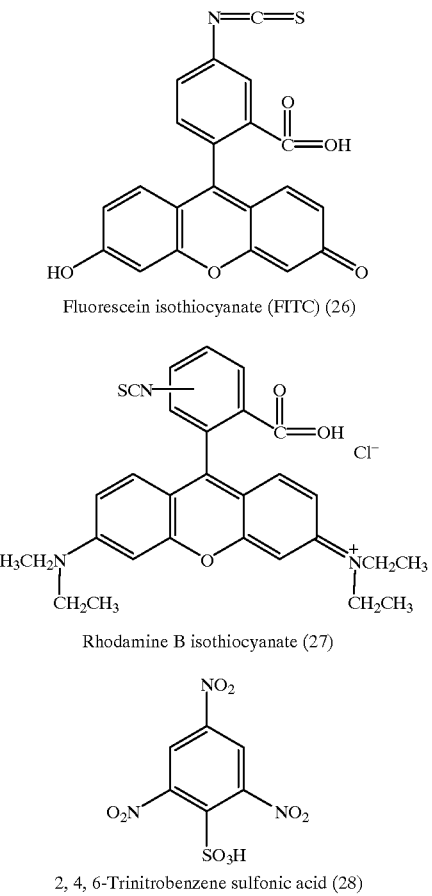

TABLE 2

Anti-HIV-1 Activitites of Chemically Modified Proteins

| Product | 1 Modified Lysines (%) | 2 $ED_{50} \pm SD$ (CPE)[1] | 3 $ED_{50} \pm SD$ (p24)[1] | 4 $ED_{50} \pm SD$ (CF)[1] | 5 $ED_{50}$ for CD4-gp120 Inhibition |
|---|---|---|---|---|---|
| | | | μg/ml | | |
| 2. Trimellitic anhydride-BSA | 77.3 | 0.26 ± 0.005 | 0.20 ± 0.03 | 3.6 ± 0.5 | 8 |
| 3. Trimellitic anhydride-dendrimers | 99.7 | 9.66 ± 1.67 | 6.07 ± 0.95 | >100 | 1.4 |
| 4. Succinic anhydride-BSA | 51.2 | 1.35 ± 0.04 | 0.56 ± 0.11 | 19.4 ± 1.9 | 40 |
| 5. Phthalic anhydride-BSA | 71.2 | 1.11 ± 0.56 | 0.63 ± 0.12 | 11.9 ± 1.3 | 2 |
| 6. Maleic anhydride-BSA | 99.7 | 0.52 ± 0.57 | 0.32 ± 0.03 | 6.5 ± 0.97 | 12 |
| 7. 1,4,5,8-Naphthalenetetracarboxylic dianhydride-BSA | 76.5 | 4.62 ± 0.28 | 4.32 ± 0.48 | 38.0 ± 5.1 | 3.6 |
| 8. Phenylglyoxal-BSA | 2.0 | >100 | >100 | >100 | 179 |
| 9. Phthalic anhydride-phenylglyoxal-BSA | 82.3 | 2.18 ± 0.104 | 1.86 ± 0.10 | 18.1 ± 2.8 | 2.6 |
| 10. 3-Hydroxphthalic anhydride-BSA | 95.5 | 0.62 ± 0.081 | 0.51 ± 0.04 | 23.4 ± 2.3 | 0.27 |
| 11. cis-Aconitic anhydride-BSA | 23.9 | 0.38 ± 0.076 | 0.21 ± 0.06 | 6.0 ± 0.6 | 18 |
| 12. Phthalic anhydride-Reduced and Alkylated BSA | 92.5 | 0.80 ± 0.14 | 0.68 ± 0.05 | 12.1 ± 3.6 | 2.6 |
| 13. Phthalic anhydride-HSA | 77.0 | 1.11 ± 0.075 | 0.55 ± 0.09 | 9.5 ± 0.14 | 4.9 |

TABLE 2-continued

Anti-HIV-1 Activitites of Chemically Modified Proteins

| Product | 1 Modified Lysines (%) | 2 ED$_{50}$ ± SD (CPE)[1] μg/ml | 3 ED$_{50}$ ± SD (p24)[1] μg/ml | 4 ED$_{50}$ ± SD (CF)[1] μg/ml | 5 ED$_{50}$ for CD4-gp120 Inhibition |
|---|---|---|---|---|---|
| 14. 1,4,5,8-Naphthalenetetracarboxylic dianhydride-HSA | 62.5 | 1.35 ± 0.14 | 1.06 ± 0.02 | 14.7 ± 4.7 | 18 |
| 15. Phthalic anhydride Rabbit Serum Albumin | 95.6 | 6.47 ± 0.55 | 5.17 ± 0.17 | 69.4 ± 5.8 | 5.8 |
| 16. Phthalic anhydride-Gelatin | 98.1 | >100 | >100 | >100 | 90 |
| 17. Phthalic anhydride-Casein I | 99.6 | 12.86 ± 2.88 | 9.92 ± 1.10 | 49.8 ± 2.6 | 5.6 |
| 18. Phthalic anhydride-Casein II | 99.6 | 8.55 ± 3.01 | 5.56 ± 0.27 | 38.9 ± 1.1 | 1.2 |
| 19. Phthalic anhydride-phenylglyoxal-Casein | 99.5 | 11.62 ± 1.15 | 5.56 ± 0.32 | 40.6 ± 1.01 | 1.1 |
| 20. Phenylglyoxal-Casein | 48.6 | 13.69 ± 2.08 | 7.13 ± 0.27 | >100 | >1,000 |
| 22. 3,3',4,4'-Benzophenonetetracarboxylic dianhydride-BSA | 98.8 | 20.40 ± 0.78 | 6.58 ± 1.15 | >100 | 8 |
| 23. 1,2,3,4-Cyclobutanetetracarboxylic dianhydride-BSA | 54.9 | 1.37 ± 0.09 | 0.67 ± 0.07 | 20.6 ± 0.8 | 8 |
| 24. Trimellitic anhydride-HSA | 81.1 | 0.30 ± 0.02 | 0.17 ± 0.03 | 4.6 ± 0.15 | 4.6 |
| 25. 1,4,5,8-Naphthalenetetracarboxylic dianhydride-Gelatin | 78.6 | >100 | >100 | >100 | 730 |
| 26. 1-Cyclopentene-1,2-dicarboxylic anhydride-BSA | 85.3 | 1.32 ± 0.05 | 1.03 ± 0.02 | 10.5 ± 0.30 | 21 |
| 27. Hexahydro-4-methylphthalic anhydride-BSA | 44 | 1.89 ± 0.22 | 1.07 ± 0.12 | 17.6 ± 3.1 | 21 |
| 28. 2-Phenylglutaric anhydride-BSA | 64.5 | 2.34 ± 0.08 | 1.57 ± 0.14 | 12.3 ± 1.15 | 13 |
| 29. 2,3-Pyrazinedicarboxylic anhydride-BSA | 38.5 | >100 | >100 | >100 | >1,000 |
| 30. Isatoic anhydride-BSA | 29.3 | 16.39 ± 3.40 | 5.63 ± 0.75 | 57.6 ± 8.4 | 1.6 |
| 31. 3-Hydroxyphthalic anhydride-milk | 87.1 | 8.15 ± 0.48 | 4.58 ± 0.65 | 10.5 ± 0.37 | 0.56 |
| 32. 3-Hydroxyphthalic anhydride-Casein | 99.3 | 11.51 ± 0.37 | 8.65 ± 1.42 | 12.4 ± 0.79 | 0.50 |
| 33. cis-Aconitic anhydride-Casein | 67.0 | 79.85 ± 3.97 | 36.20 ± 9.74 | >100 | 4.2 |
| 34. (4)-Diacetyl-4-tartaric anhydride-BSA | 62.7 | >100 | >100 | >100 | >1,000 |
| 35. Trimellitic anhydride chloride-BSA | 43.4 | 0.27 ± 0.01 | 0.12 ± 0.01 | 1.7 ± 0.08 | 0.21 |
| 36. exo-3,6-Epoxy-1,2,3,6-tetrahydrophthalic anhydride-BSA | 64.6 | 4.35 ± 0.82 | 2.10 ± 0.29 | 89.0 ± 2.4 | |
| 37. N-Phthaloyl-DL-glutamic anhydride-BSA | 64.0 | 1.24 ± 0.23 | 1.06 ± 0.074 | 9.2 ± 0.94 | 0.9 |
| 38. Trimellitic anhydride-phenylglyoxal-BSA | 90.4 | 0.67 ± 0.05 | 0.49 ± 0.03 | 4.4 ± 0.13 | 0.7 |
| 39. Trimellitic anhydride phenylglyoxal-HSA | 88.2 | 0.63 ± 0.08 | 0.48 ± 0.02 | 3.6 ± 0.29 | 0.7 |
| 40. 2,3-Pyridinedicarboxylic anhydride-BSA | 62.7 | >100 | >100 | >100 | 1,000 |
| 41. Ethylenediaminetetraacetic dianhydride-BSA | 96.1 | >100 | >100 | >100 | 25 |
| 42. 3,6-Difluorophthalic anhydride-BSA | 28.6 | >100 | >100 | >100 | >1,000 |
| 43. 1,4,5,6,7,7-Hexachloro-5-norbornene-2,3-dicarboxylic anhydride-BSA | 32.2 | >100 | >100 | >100 | 200 |
| 44. 3,5-Diacetyltetrahydropyran-2,4,6-trione-BSA | 17.8 | >100 | >100 | >100 | >1,000 |
| 45. Trimellitic anhydride-transferrin | 51.9 | 0.56 ± 0.09 | 0.33 ± 0.03 | 24.3 ± 2.02 | 11 |
| 46. Trimellitic anhydride-trypsin-treated-BSA | 86.9 | 1.40 ± 0.16 | 0.74 ± 0.17 | 35.7 ± 1.6 | 15 |
| 47. Trimellitic anhydride-IgG | 88 | 1.22 ± 0.08 | 0.56 ± 0.08 | 20.9 ± 0.78 | 25 |
| 48. 4-Carboxybenzaldehyde-BSA | 87.7 | >100 | >100 | >100 | >1,000 |
| 49. Trimellitic anhydride-poly-D-Lysine | 9.6 | >100 | >100 | >100 | >1,000 |
| 50. 2,4,6-Trinitrobenzene sulfonic acid-BSA | 100 | 9.44 ± 0.76 | 8.50 ± 2.58 | 60.3 ± 5.8 | 2.8 |
| 51. FITC[1]-BSA | 18.6 | *[2] | *[2] | 58.4 ± 7.9 | 28 |
| 52. Rhodamine B isothiocyanate-BSA | 54.2 | *[2] | *[2] | 54.8 ± 6.9 | 26 |
| 53. Trimellitic anhydride-Casein | 98.8 | 5.80 ± 0.37 | 6.69 ± 1.18 | >100 | 11 |
| 54. Trimellitic anhydride chloride-Casein | 98.4 | 4.06 ± 0.20 | 5.56 ± 0.39 | >100 | 37 |
| 55. Trimellitic anhydride-milk | 95.4 | 4.09 ± 0.37 | 1.88 ± 0.003 | >35 | 2.78 |
| 56. Trimellitic anhydride chloride-milk | 92.3 | 4.75 ± 0.98 | 2.36 ± 0.66 | >35 | 1.6 |
| 57. cis-Aconitic anhydride-milk | 72.8 | 43.80 ± 2.10 | 31.80 ± 1.80 | >100 | 11.8 |
| 58. Maleic anhydride-milk | 93.3 | 15.40 ± 2.10 | 9.50 ± 2.40 | >100 | 36.5 |
| 59. cis-Aconitic anhydride-phenylglycoxal-milk | 93.3 | 9.00 ± 1.02 | 3.71 ± 1.05 | 30.9 ± 2.9 | 0.17 |
| 60. 3-Hydroxyphthalic anhydride-phenylglyoxal-milk | 87.1 | 5.10 ± 1.31 | 2.03 ± 0.45 | 26.7 ± 0.4 | 1.04 |
| 61. Trimellitic anhydride chloride-HSA | 97.5 | 0.33 ± 0.03 | 0.11 ± 0.006 | 5.5 ± 0.81 | 19 |
| 62. FITC[1]-BSA II | 21.8 | 2.66 ± 0.57 | 1.28 ± 0.30 | 95.6 ± 8.9 | 3.6 |
| 63. 3-Hydroxyphthalic anhydride-β-Lactoglobulin | 73.2 | 2.7 ± 0.3 | 1.2 ± 0.2 | 17.7 ± 0.4 | 0.085 |
| 64. 3-Hydroxyphthalic anhydride (1:1 mg/ml)-β-Lactoglobulin | 99.1 | 2.4 ± 0.03 | 1.4 ± 0.1 | 16.3 ± 1.5 | 0.064 |
| 65. 3-Hydroxyphthalic anhydride (5:1 mg/ml)-β-Lactoglobulin | 87.7 | 2.4 ± 0.1 | 1.8 ± 0.3 | 16.4 ± 1.5 | 0.088 |
| 66. PEGylated 3-Hydroxyphthalic anhydride-β-Lactoglobulin | 73.2 | 2.3 ± 0.1 | 2.3 ± 0.1 | 17.5 ± 1.0 | 3.6 |
| 67. 3-Hydroxyphthalic anhydride-Whey | 50.6 | 15.1 ± 2.3 | 7.7 ± 0.8 | 50.1 ± 3.4 | 1.9 |
| 68. 3-Hydroxyphthalic anhydride-Egg Albumin grade IV | 91.7 | 7.9 ± 0.6 | 5.9 ± 1.3 | 39.4 ± 2.0 | 1.6 |
| 69. 3-Hydroxyphthalic anhydride-Egg White | 92.0 | 10.5 ± 0.7 | 9.3 ± 0.5 | 55.4 ± 6.2 | 0.029 |
| 70. 3-Hydroxyphthalic anhydride-purified Ovomucoid | 88.2 | 10.6 ± 0.2 | 8.5 ± 0.7 | 152.0 ± 12.7 | 9.4 |
| 71. 3-Hydroxyphthalic anhydride-partially purified Ovomucoid | 90.7 | 6.5 ± 0.5 | 5.1 ± 0.4 | 93.7 ± 4.0 | 14.1 |
| 72. p-Carboxyphenylglyoxal-BSA | 0** | 15.9 ± 3.2 | 8.6 ± 1.9 | 673.0 ± 51.9 | 8.0 |

TABLE 2-continued

Anti-HIV-1 Activitites of Chemically Modified Proteins

| Product | 1 Modified Lysines (%) | 2 $ED_{50} \pm SD$ (CPE)[1] | 3 $ED_{50} \pm SD$ (p24)[1] µg/ml | 4 $ED_{50} \pm SD$ (CF)[1] | 5 $ED_{50}$ for CD4-gp120 Inhibition |
|---|---|---|---|---|---|
| 73. 1,2,4-Benzenetricarboxylic anhydride-β-Lactoglobulin | 66.5 | 0.83 ± 0.3 | 0.24 ± 0.05 | 10.6 ± 2.2 | 0.32 |
| 74. Trimellitic anhydride chloride-β-Lactoglobulin | 59.3 | 1.4 ± 0.2 | 0.28 ± 0.06 | 15.9 ± 3.8 | 0.38 |
| 75. Purified Ovomucoid | 0 | >100 | >100 | >800 | >1000 |
| 76. Partially purified Ovomucoid | 0 | >100 | >100 | >800 | >1000 |
| 77. 1,2,4-Benzenetricarboxylic anhydride-Hemoglobin | N.D.*** | 5.9 ± 1.0 | 5.3 ± 0.8 | 45.0 ± 4.8 | 3.6 |
| 78. Pyridoxal Phosphate-β-Lactoglobulin | 57.1 | >100 | >100 | >800 | >1000 |

Abbreviations
[1]$ED_{50}$: concentrations at which cytopathic effect (CPE), production of the HIV-1 nucleocapsin antigen p24, and cell fusion (CF) and gp120 binding to CD4, respectively, were one half of those detected in the absence of inhibitors.
[2]$ED_{50}$ could not be determined since the compound was cytotoxic
** Reagent specific for arginine.
*** Not done (method not suitable for hemoglobin).

TABLE 3

Antiviral activity of 3-hydroxyphthalic anhydride treated bovine β-lactoglobulin (3HP-β-LG) again st primate immunodeficiency viruses

| | $IC_{50} \pm SD$* (nM) as measured by inhibition of nucleocapsid | |
|---|---|---|
| Virus | antigen production | CPE |
| A. Laboratory HIV-1 strains | | |
| IIIB | 4.3 ± 1.0 | 6.8 ± 0.2 |
| MN | 13.1 ± 4.4 | 7.8 ± 0.1 |
| RF | 2.6 ± 0.3 | 7.3 ± 0.7 |
| SF2 | 20.7 ± 3.2 | 18.2 ± 3.3 |
| $V_{32}$ | 20.1 ± 2.7 | 21.6 ± 5.3 |
| B. AZT-resistant HIV-1 panel | | |
| Pre-drug isolate 629 | 88.0 ± 4.8 | 110.6 ± 2.9 |
| Post-drug isolate 1075. intermediate resistant | 87.7 ± 6.8 | 95.3 ± 5.1 |
| Post-drug isolate 629, resistant | 112.4 ± 12.4 | 75.6 ± 9.1 |
| C. Primary HIV-1 isolates | | |
| 301593 | 168 ± 25 | —** |
| 301660 | 94 ± 34 | —** |
| 302054 | 255 ± 99 | —** |
| 302056 | 124 ± 33 | —** |
| D. Crimeric HIV-1/SIV | | |
| SHIV-1 | 3.2 ± 0.7 | 8.1 ±0.9 |
| E. HIV-2 ROD | 45.8 ± 5.0 | 192 ± 33 |
| F. SIVmac251 | 35.8 ± 6.4 | —** |

*Abbreviations: $IC_{50}$, concentrations at which the cytoparmic effect (CPE) and nucleocapsid antigen production, respectively, were 50% of those detected in the absence of 3HP-β-LG: SD, standard deviation.
—**CPE not measurable by spectrophotometry.

TABLE 4

Detergents for Treating Soy Proteins

| CHEMICAL NAME OR TRADE NAME | CHEMICAL SYNONYMS |
|---|---|
| Big CHAP | N,N,bis(3-D-gluconamidopropyl)cholamide |
| BRIJ 35 | LAURETH-23 |
| | Polyoxyethylene (23) lauryl ether $C_{12}E_{23}$ |
| $C_{12}E_8$ | Octaethylene glycol monododecyl ether |
| | Octaethylene glycol monolauryl ether |
| | Polyoxyethylene (8) lauryl ether |
| $C_{12}E_9$ | Nonaethylene glycol monododecyl ether |
| | Nonoctaethylene glycol monolauryl ether |

TABLE 4-continued

Detergents for Treating Soy Proteins

| CHEMICAL NAME OR TRADE NAME | CHEMICAL SYNONYMS |
|---|---|
| | Polyoxyethylene (9) lauryl ether |
| Cetyltrimethylammonium bromide | CTAB |
| | Cetrimmonium bromide |
| | Cetrimide |
| CHAPS | 3-[(3-Cholamidopropyl)dimethylammonio]-1-propanesulfonate |
| CHAPSO | 3-[(3-Cholamidopropyl)dimethylammonio]-2-hydroxypropane-1-sulfonate |
| Cholate, sodium | Cholic acid monosodium salt |
| | Sodium cholic acid |
| Decyl-β-D-glucopyranoside | Decyl glucoside |
| Decyl-β-D-maltopyranoside | Decyl maltoside |
| Deoxy Big CHAP | N,N-bis(3-D-gluconamidopropyl)deoxycholamide |
| Deoxycholate, sodium | Deoxycholic acid, sodium salt |
| | Sodium deoxycholic acid |
| Digitonin | Digitin |
| Dodecyl-β-D-maltopyranoside | Dodecyl maltoside; |
| | Lauryl maltoside |
| Dodecyl sulfate, sodium | lauryl sulfate, sodium |
| EMPIGEN BB | N-Dodecyl-N,N-dimethylglycine |
| | N-Lauryl-N,N-dimethylglycine |
| bis(2-Ethylhexyl)sodium sulfosuccinate | Dioctyl sodium sulfosuccinate: docusate sodium |
| GENAMINOX KC | Lauryldimethylamine oxide |
| | Dodecyldimethylamine oxide |
| | LDAO |
| GENAPOL C-100 | Polyoxyethylene (10) monolauryl ether |
| | Decaoxyethylene monolauryl ether |
| | Decaoxyethylene dodecyl ether |
| GENAPOL X-080 | Octaethylene glycol isotridecyl ether |
| | Polyoxyethylene (8) isotridecyl ether |
| GENAPOL X-100 | Polyoxyethylene (10) isotridecyl ether |
| | PEG (10) tridecyl ether |
| GENAPOL X-150 | Polyoxyethylene (15) isotridecyl ether |
| | PEG (15) isotridecyl ether |
| Glycocholate, sodium | Glycocholic acid, sodium salt |
| | Monosodium glycocholic acid |
| Glycodeoxycholate, sodium | Glycodeoxycholic acid, sodium salt |
| Heptyl-β-D-glucopyranoside | Heptyl glucoside |
| Heptyl-β-D-thioglucopyranoside | Heptyl thioglucoside |
| Hexyl-β-D-glucopyranoside | Hexyl glucoside |
| Lauryldimethylamine oxide | Dodecyldimethylamine oxide |
| | Dimethyllaurylamine oxide |
| | N,N-Dimethyl-N-dodecylamine oxide |
| | LDAO |
| Lauryl sulfate, sodium | Sodium lauryl sulfate |
| | Sodium dodecyl sulfate |
| | SDS |
| | SLS |
| LUBROL PX | Polyoxyethylene (9) lauryl ether |
| | PEG (9) dodecyl ether |
| | Polidocanol |
| MEGA-8 | OMEGA |
| | Octanoyl-N-methylglucamide |
| MEGA-9 | Nonanoyl-N-methylglucamide |
| MEGA-10 | Decanoyl-N-methylglucamide |
| Nonyl-β-D-glucopyranoside | Nonyl glucoside |
| NP-40 | NONIDET P-40 |
| | Nonaethylene glycol octylphenyl ether |
| | PEG (9) octylphenyl ether |
| Octyl-β-D-glucopyranoside | Octyl glucoside |
| | OG |
| Octyl-β-D-thioglucopyranoside | Octyl thioglucoside |
| | OSG |
| PLURONIC F-127 | Polyoxyethylene polyoxypropylene block copolymer |
| | Polyethylene polypropylene glycol |
| Taurocholate, sodium | Taurocholic acid, sodium salt |
| | Monosodium taurocholic acid |
| Taurodeoxycholate, sodium | Taurodeoxycholic acid, sodium salt |
| | Sodium taurodesoxycholate |
| THESIT | $C_{12}E_9$ |
| | Nonaethylene glycol mono-dodecyl ether |
| TRITON X-100 | Nonaethylene glycol octylphenol ether |
| | PEG (9) octylphenyl ether |

TABLE 4-continued

Detergents for Treating Soy Proteins

| CHEMICAL NAME OR TRADE NAME | CHEMICAL SYNONYMS |
|---|---|
| TRITON X-100, Hydrogenated | RTX-100 |
| TRITON X-114 | Heptaethylene glycol octylphenyl ether |
|  | PEG (7) octylphenyl ether |
| TWEEN 20 | Polyoxyethylene sorbitan monolaurate |
|  | PEG (20) sorbitan monolaurate |
|  | POLYSORBATE 20 |
| TWEEN 80 | Polyoxyethylene sorbitan monoleate |
|  | PEG (20) sorbitan monoleate |
|  | POLYSORBATE 80 |
| ZWITTERGENT 3-08 | N-octylsulfobetaine |
|  | 3-(Octyldimethylammonio)propane-1-sulfonate |
|  | SB 3-08 |
|  | SB08 |
| ZWITTERGENT 3-10 | N-Decylsulfobetaine |
|  | 3-(Decyldimethylammonio)propane-1-sulfonate |
|  | SB3-10 |
|  | SB10 |
| ZWITTERGENT 3-12 | N-Dodecylsulfobetaine |
|  | 3-(Dodecyldimethylammonio)propane-1-sulfonate |
|  | SB 3-12 |
|  | SB10 |
| ZWITTERGENT 3-14 | N-Tetradecylsulfobetaine |
|  | 3-(Dodecyldimethylammonio)propane-1-sulfonate |
|  | SB 3-14 |
|  | SB14 |
| ZWITTERGENT 3-16 | N-Hexadecylsulfobetaine |
|  | 3-(Hexadecyldimethylammonio)propane-1-sulfonate |
|  | SB 3-16 |
|  | SB16 |
| n-Dodecanoylsucrose |  |
| octandoyl sucrose |  |
| tetradecyl-beta-D-maltoside |  |
| dimethyldioctadelyl ammonium bromide |  |

TABLE 5

Anti-HIV-1 Activity of Soy Proteins Treated by Detergents

| Detergent | IC$_{50}$ (µg/ml) |
|---|---|
| SDS | 13.62 ± 1.44 |
| Dimethyldioctadelyl ammonium bromide | 26.58 ± 8.19 |
| Cholic acid | 20.16 ± 1.76 |
| CHAPS | 17.45 ± 3.90 |

Table 6. Inhibition by 3-Hydroxyphthalic Anhydride Treated Bovine β-Lactoglobulin (3-HP-β-LG) of β-Galactosidase Induction in Hela-CD4-LTR-8-gal Cells Cocultivated With HIV-1 and HIV-2 Infected Cells

| Cell line used for infection | IC$_{50}$ ± SD* (nM) | IC$_{90}$ ± SD* (nM) |
|---|---|---|
| H9-HIV-1-IIIB | 75 ± 14 | 590 ± 107 |
| U937-HIV-2-ROD | 118 ± 24 | 2,786 ± 561 |

*IC$_{50}$ and IC$_{90}$, concentrations at which the production of β-gal was inhibited by 50% and 90%, respectively, as compared with control cultures to which 3HP-β-LG was not added (=22.4 and 11.6 mg/ml of β-gal for cocultures containing HIV-1 and HIV-2 infected cells, respectively); SD, standard deviation. Hela-CD4-LTR-β-gal cells produced −0.5 to 1 ng/ml of β-gal in the absence of infected cells.

The inhibitory effect of 3HP-β-LG on induction of β-gal in cells containing an integrated β-gal gene that is under the control of a truncated HIV-1 long terminal repeat (LTR), cocultivated with infected cells was measured. Hela-CD4-LTR-α-gal cells (2×10$^5$ in 100 µl) in 96-well flat bottom Corning tissue culture plates were mixed with 50 µl of 0 to 13.5 µM 3HP-β-LG. After 1 hour at 25° C., H9 and U937 cells chronically infected with HIV-IIIB and HIV-2-ROD, respectively (5×10$^4$ cells in 50 µl; prewashed to remove cell-free virus) were added. The cells were suspended in RPMI 1640 medium and 10% fetal bovine serum. After 48 Furs at 37° C., the cells were lysed with 50 µl of 5% TRITON X-100 containing protease inhibitors (phenylmethyl-sulfonyl fluoride, leupeptin and pepstatin, all at 10 µg/ml). β-gal protein in 1:10 diluted lysates was quantitated using an ELISA kit from 5 Prime→3 Prime Inc. (Boulder, Colo.).

It will be appreciated that the instant specification is set forth by way of illustration and not limitation, and that various modifications and changes may be made without departure from the spirit and scope of the present invention.

We claim:

1. A composition comprising beta-lactoglobulin wherein at least one lysine or N-terminal amino acid group thereof is modified by an aromatic anhydride compound selected from the group consisting of trimellitic anhydride, trimellitic anhydride chloride and 3-hydroxyphthalic anhydride to make said composition capable of binding to a CD4 cell receptor, wherein the aromatic anhydride compound used for modification of the beta-lactoglobulin is in an amount of 0.1 to 100 grams per gram of the beta-lactoglobulin.

2. The composition of claim 1, wherein the aromatic anhydride compound is 3-hydroxyphthalic anhydride.

3. The composition of claim 1, wherein the aromatic anhydride compound is trimellitic anhydride.

4. The composition of claim 1, wherein the aromatic anhydride compound is trimellitic anhydride chloride.

5. The composition of claim 1, wherein the aromatic anhydride compound used for modification of the beta-lactoglobulin is in an amount of 1 to 100 grams per gram of the beta-lactoglobulin.

6. The composition of claim 1, wherein said binding is to the HIV-1 or HIV-2 binding site on said CD4 cell receptor.

7. A method of modifying a beta-lactoglobulin comprising contacting the beta-lactoglobulin with an aromatic anhydride compound selected from the group consisting of trimellitic anhydride, trimellitic anhydride chloride and 3-hydroxyphthalic anhydride to modify at least one lysine or the N-terminal amino acid group of the beta-lactoglobulin to make the beta-lactoglobulin capable of binding to a CD4 cell receptor, wherein the aromatic anhydride compound is in an amount of 0.1 to 100 grams per gram of the beta-lactoglobulin and the contacting is carried out at a temperature of 0 to 50° C. for 15 to 720 minutes at a pH of 6 to 11.

8. The method of claim 7, wherein the aromatic anhydride compound is 3-hydroxyphthalic anhydride.

9. The method of claim 7, wherein the aromatic anhydride compound is trimellitic anhydride.

10. The method of claim 7, wherein the aromatic anhydride compound is trimellitic anhydride chloride.

11. The method of claim 7, wherein the aromatic anhydride compound is in an amount of 1 to 10 grams per gram of the beta-lactoglobulin and the contacting is carried out at a temperature of 15° C. to 30° C. for 30 to 180 minutes at a pH of 6 to 9.

12. The method of claim 7, wherein said binding is to the HIV-1 or HIV-2 binding site on said CD4 cell receptor.

13. A method of preventing HIV-1 or HIV-2 infection in a human comprising locally administering to a human a pharmaceutically effective amount of the composition of claim 1, either alone or in combination with a pharmaceutically acceptable carrier.

14. The method of claim 13, wherein the composition is topically administered.

15. The method of claim 13, wherein the aromatic anhydride compound is 3-hydroxyphthalic anhydride.

16. The method of claim 13, wherein the aromatic anhydride compound is trimellitic anhydride.

17. The method of claim 13, wherein the aromatic anhydride compound is trimellitic anhydride chloride.

* * * * *